United States Patent
Luedtke et al.

(10) Patent No.: US 12,398,105 B2
(45) Date of Patent: Aug. 26, 2025

(54) ANALOGUES OF PENTAMIDINE AND USES THEREFOR

(71) Applicant: Auransa Inc., Palo Alto, CA (US)

(72) Inventors: Gregory R. Luedtke, Salinas, CA (US); Andrew Asher Protter, Palo Alto, CA (US); Anna Halberg, Palo Alto, CA (US); Pek Yee Lum, Palo Alto, CA (US); Rajaa Sukhun, Palo Alto, CA (US); Sidney Paul Elmer, Palo Alto, CA (US); Hak Jin Chang, Harvard, MA (US)

(*) Notice: Subject to any disclaimer, the term of this patent is extended or adjusted under 35 U.S.C. 154(b) by 997 days.

(21) Appl. No.: 17/415,681

(22) PCT Filed: Dec. 20, 2019

(86) PCT No.: PCT/US2019/068156
§ 371 (c)(1),
(2) Date: Jun. 17, 2021

(87) PCT Pub. No.: WO2020/132636
PCT Pub. Date: Jun. 25, 2020

(65) Prior Publication Data
US 2022/0144776 A1    May 12, 2022

Related U.S. Application Data

(60) Provisional application No. 62/782,351, filed on Dec. 20, 2018.

(51) Int. Cl.
*C07D 213/81* (2006.01)
*A61P 35/00* (2006.01)
*C07C 251/24* (2006.01)

(52) U.S. Cl.
CPC ........... *C07D 213/81* (2013.01); *A61P 35/00* (2018.01); *C07C 251/24* (2013.01)

(58) Field of Classification Search
CPC .............................. C07D 213/81; A61P 35/00
See application file for complete search history.

(56) References Cited

U.S. PATENT DOCUMENTS

| | | |
|---|---|---|
| 2,277,861 A | 3/1942 | James et al. |
| 2,410,796 A | 11/1946 | George et al. |
| 4,683,202 A | 7/1987 | Mullis et al. |
| 5,084,480 A | 1/1992 | Pai et al. |
| 5,800,992 A | 9/1998 | Fodor et al. |
| 5,854,033 A | 12/1998 | Lizardi |
| 6,020,135 A | 2/2000 | Levine et al. |
| 6,033,860 A | 3/2000 | Lockhart et al. |
| 6,040,138 A | 3/2000 | Lockhart et al. |
| 6,344,316 B1 | 2/2002 | Lockhart et al. |
| 6,469,182 B1 | 10/2002 | Littlefield et al. |
| 6,653,341 B1 | 11/2003 | Littlefield et al. |
| 2004/0063769 A1 | 4/2004 | Borisy et al. |
| 2011/0053156 A1 | 3/2011 | Kloppel et al. |
| 2012/0128667 A1 | 5/2012 | Chow et al. |
| 2015/0111965 A1 | 4/2015 | Clement et al. |
| 2021/0378992 A1 | 12/2021 | Grahnen et al. |

FOREIGN PATENT DOCUMENTS

| | | | |
|---|---|---|---|
| EP | 1339399 B1 | 3/2006 | |
| JP | 2016079175 A | * 5/2016 | |
| WO | WO-03074476 A1 | * 9/2003 | ........... C07C 257/18 |
| WO | 2009051796 A2 | 4/2009 | |
| WO | 2017156177 A1 | 9/2017 | |
| WO | 2020082037 A1 | 4/2020 | |

OTHER PUBLICATIONS

Bakunova et al., "Synthesis and Antiprotozoal Activity of Pyridyl Analogues of Pentamidine", 2009, Journal of Medicinal Chemistry, 52, pp. 4657-4667 (Year: 2009).*
Da Silva et al., "The biological in vitro effect and selectivity of aromatic dicationic compounds on Trypanosoma cruzi", 2010, Mem Inst Oswaldo Cruz, 105, pp. 239-245 (Year: 2010).*
Adam, B. L. et al. (Jul. 1, 2002). "Serum Protein Fingerprinting Coupled With A Pattern-Matching Algorithm Distinguishes Prostate Cancer From Benign Prostate Hyperplasia And Healthy Men," Cancer Research 62(13):3609-3614.
Barany, F. (Jan. 1991). "Genetic Disease Detection And DNA Amplification Using Cloned Thermostable Ligase," Proceedings Of The National Academy of Sciences 88(1):189-193.
Cabiati, M. et al. (May 8, 2012). "Tissue-Specific Selection Of Stable Reference Genes For Real-Time PCR Normalization In An Obese Rat Model," Journal Of Molecular Endocrinology 48(3):251-260.
George, J. et al. (Aug. 6, 2015, e-pub. May 9, 2016). "Comprehensive Genomic Profiles Of Small Cell Lung Cancer," Nature 524(7563):47-53.
Guatelli, J. C. et al. (Mar. 1990). "Isothermal, In Vitro Amplification Of Nucleic Acids By A Multienzyme Reaction Modeled After Retroviral Replication," Proceedings of the National Academy of Sciences 87(5):1874-1878.

(Continued)

*Primary Examiner* — Brenda L Coleman
*Assistant Examiner* — Madeline E Braun
(74) *Attorney, Agent, or Firm* — ENTRALTA PLLC; James F. Fleming; Peter D. Weinstein

(57) ABSTRACT

The present disclosure provides a group of aromatic (e.g., pyridinyl, pyrimidinyl, pyrazinyl, or phenyl) diamidine analogs and pharmaceutically acceptable salts that are useful for treating a proliferative disease. The proliferative disease may include solid cancer or blood cancer. Compositions, methods of synthesizing the same and methods for treating various cancer using the analogs are disclosed herein. The present disclosure also provides pharmaceutical formulations comprising at least one of the compounds with a pharmaceutically acceptable carrier, diluent or excipient therefor.

25 Claims, 11 Drawing Sheets

(56) References Cited

OTHER PUBLICATIONS

International Preliminary Report on Patentability issue date of Apr. 14, 2021 for Patent Application No. PCT/US2019/57080 filed on Oct. 18, 2019, 7 pages.

International Preliminary Report on Patentability issue date of Jun. 16, 2021 for Patent Application No. PCT/US19/068156, filed Dec. 20, 2019, 7 pages.

International Search Report and Written Opinion mailed on Apr. 8, 2020, for PCT Application No. PCT/US2019/068156 filed on Dec. 20, 2019, 10 pages.

International Search Report and Written Opinion mailed on Jan. 13, 2020, for PCT Application No. PCT/US2019/57080 filed on Oct. 18, 2019, 9 pages.

Invitation to Pay Additional Fees, mailed on Feb. 14, 2020, for PCT Application No. PCT/US19/068156 filed on Dec. 20, 2019, 2 pages.

Kwoh, D. Y. et al. (Feb. 1989). "Transcription-Based Amplification System And Detection Of Amplified Human Immunodeficiency Virus Type 1 With A Bead-Based Sandwich Hybridization Format," Proceedings Of The National Academy Of Sciences 86(4):1173-1177.

Laronga, C. et al. (Jan. 1, 2003). "SELDI-TOF Serum Profiling For Prognostic And Diagnostic Classification Of Breast Cancers," Disease Markers 19(2003,2004):229-238.

Leek, J. T. et al. (Oct. 2010, e-pub. Jan. 3, 2014). "Tackling The Widespread And Critical Impact Of Batch Effects In High-Throughput Data," Nature Reviews Genetics 11(10):733-739.

Li, J. et al. (Aug. 1, 2002). "Proteomics And Bioinformatics Approaches For Identification Of Serum Biomarkers To Detect Breast Cancer," Clinical Chemistry 48(8):1296-1304.

Lizardi, P. M. et al. (Oct. 1, 1988). "Exponential Amplification Of Recombinant-RNA Hybridization Probes," Bio/technology 6(10):1197-1202.

NIH (Mar. 25, 2005). "Pentamidine," PubChem Compound Summary for CID 4735, 41 pages, retrieved on Mar. 23, 2022 from https://pubchem.ncbi.nlm.nih.gov/compound/Pentamidine.

Rudin, C. M. et al. (Oct. 2012). "Comprehensive Genomic Analysis Identifies SOX2 As A Frequently Amplified Gene In Small-Cell Lung Cancer," Nature Genetics 44(10):1111-1116.

Sperandei, S. (2014). "Understanding Logistic Regression Analysis," Biochemia Medica 24(1):12-18.

Tilli, T. M. et al. (2016). "A Strategy To Identify Housekeeping Genes Suitable For Analysis In Breast Cancer Diseases," BMC Genomics 17(639):1-11.

Tolson, J. et al. (Apr. 26, 2004). "Serum Protein Profiling By SELDI Mass Spectrometry: Detection Of Multiple Variants Of Serum Amyloid Alpha In Renal Cancer Patients," Laboratory Investigation 84(7):845-856.

Vandesompele, J. et al. (Jun. 18, 2002). "Accurate Normalization Of Real-Time Quantitative RT-PCR Data By Geometric Averaging Of Multiple Internal Control Genes," Genome Biology 3(7):1-12.

Xiao, Z. et al. (Aug. 15, 2001). "Quantitation Of Serum Prostate-Specific Membrane Antigen By A Novel Protein Biochip Immunoassay Discriminates Benign From Malignant Prostate Disease," Cancer Research 61(16):6029-6033.

Zhang, W. et al. (Feb. 2, 2018). "Small cell lung cancer tumors and preclinical models display heterogeneity of neuroendocrine phenotypes," Translational lung cancer research 7(1):32-49.

Zhu, J. et al. (Apr. 16, 2008). "How Many Human Genes Can Be Defined As Housekeeping With Current Expression Data?" BMC Genomics 9(1):1-11.

\* cited by examiner

ANALOGUES OF PENTAMIDINE AND USES THEREFOR

CROSS REFERENCE TO RELATED APPLICATIONS

This application is a national stage application under 35 U.S.C. § 371 of International Application No. PCT/US2019/068156, filed Dec. 20, 2019, which claims priority to U.S. Provisional Application Ser. No. 62/782,351, filed Dec. 20, 2018, which are hereby incorporated by reference in their entirety.

FIELD OF THE INVENTION

The present invention relates to compounds useful for therapy or prophylaxis in a mammal, and in particular to the treatment of cancer.

BACKGROUND OF THE INVENTION

Pentamidine, 1,5-bis(4-amidinophenoxy) pentane, came into medical use in 1937 and is on the World Health Organization's List of Essential Medicines as an antiprotozoal/antifungal agent for treating various infectious diseases (e.g., African trypanosomiasis, leishmaniasis, babesionsis, and *Pneumocystis carinii* pneumonia). Although the precise mode of pharmaceutical action still remains to be elucidated, pentamidine has been has been known to preferentially bind to DNA in the minor groove of AT-rich domains and proposed to exhibit anticancer activities through its inhibitory effects on PRLs (phosphatase of regenerating liver family), endo-exonuclease activity, and interaction between S100B and p53.

Despite the fact that pentamidine has been used as active therapeutic compound for decades, numerous side effects have greatly limited the use of this drug against parasitic infections, and most of therapy implementing this compound require careful monitoring on adverse events and dose responses as it may cause diabetes and adverse effects on the central nervous system. Particularly among its side effects, patients under pentamidine therapy commonly exhibit transient elevation of serum liver transaminases (e.g., ALT and AST liver injury markers), indicative of liver damage. Due to these potentially harmful consequences on vital organ(s), development of this compound as an anticancer drug which often require an increased amount of dose has been severely limited, as it is in its use for microbial infections.

Pentamidine can be administered intramuscularly (IM) or intravenously (IV). However, only the IV administration is the recommended route for treating infectious diseases. This is because the compound suffers greatly from poor oral bioavailability. Some studies have shown that the toxic side effects can be managed if the drug is given via aerosol administration. However, this specific mode of administration is limited to the treatment of pneumonia. Various approaches, such as pentamidine prodrugs, have been taken to overcome the compound's shortcomings in oral bioavailability, but there is no pentamidine analogue reported to date that provides a safe and effective exposure at therapeutic levels, particularly via oral administration with reduced toxicity.

Given the toxic side effects of pentamidine, there is a dire need for safe and effective, non-toxic pentamidine analogs that exhibit increased organ targeting that may allow for oncological clinical development designed for specific types of cancer.

BRIEF SUMMARY

Figure 1:
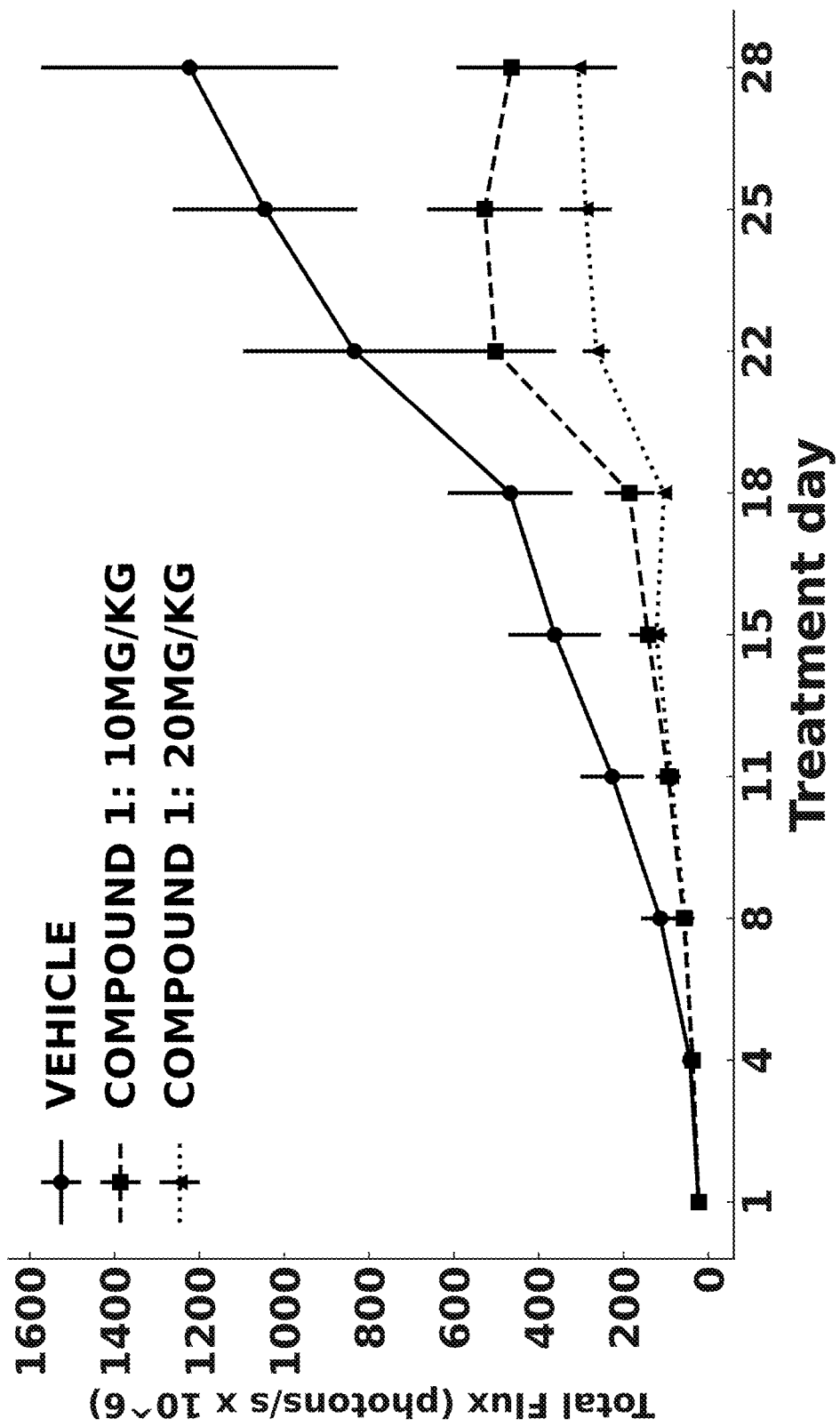
FIG. 1 depicts in vivo effects of Compound 1 on orthotopic BALB/c nude mice carrying liver cancer cell line. Mice were treated with Compound 1 at doses of 10 mg/kg and 20 mg/kg, orally (p.o.), Q3D for a week followed by QD for 3 weeks.

The present disclosure is drawn to a group of aromatic (e.g., pyridinyl, pyrimidinyl, pyrazinyl, or phenyl) diamidine analogs and pharmaceutically acceptable salts that are useful for treating a proliferative disease. The proliferative disease may include solid cancer or blood cancer. Compositions, methods of synthesizing the same and methods for treating various cancer using the analogs are disclosed herein. The present disclosure also provides pharmaceutical formulations comprising at least one of the compounds with a pharmaceutically acceptable carrier, diluent or excipient therefor.

The present invention is based on a discovery that the analogs of pentamidine are useful for treating various types of cancer, including but not limited to, liver cancer, lung cancer, colon cancer, cholangiocarcinoma, renal cancer, gastric cancer, melanoma, ovarian cancer, breast cancer, and pancreatic cancer. These aromatic diamidine compounds demonstrate similar or increased cytotoxicity against cancer cells as compared to pentamidine and also exhibit enhanced pharmacokinetics and pharmacodynamics to the liver with greatly enhanced oral bioavailability, rendering the compounds significantly safer than pentamidine or other standard-of-care molecules. In sum, these properties make the compounds of the present invention highly desirable for clinical development for cancer treatment.

In one aspect, the present invention is drawn to compositions of pentamidine analogs having Formula (A):

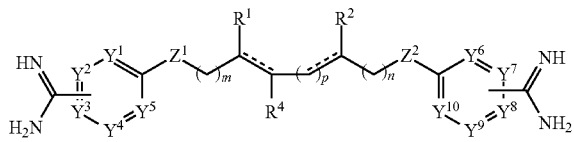

Formula (A)

or a pharmaceutically acceptable salt thereof, wherein:
===== presents a single or double bond;
m or n is independently an integer of 0, 1, 2 or 3;
p is or 1;
$Z^1$ or $Z^2$ is independently O, S, $SO_2$, $NR^3$, or $CR^5R^6$;
$Y^1$-$Y^{10}$ are each independently N or $CR^7$, wherein at least one of $Y^1$-$Y^{10}$ is N, provided that when the moiety

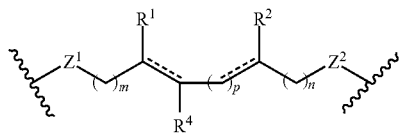

is taken together to form the moiety

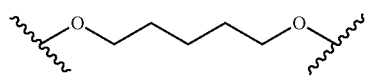 [SMILES: *OCCCCCO*]

one $Y^1$-$Y^5$ is N and one of $Y^8$-$Y^{10}$ is N and the remaining $Y^1$-$Y^{10}$ are each CH, then $Y^1$-$Y^5$ are taken together with the amidine substituent to form an amidine substituted pyridine ring that is different than the amidine substituted pyridine ring formed by $Y^8$-$Y^{10}$;
$R^1$ and $R^2$ are each independently hydrogen or halo,
or $R^1$ taken together with $R^2$ forms a saturated, unsaturated or partially unsaturated 3-9 membered cyclic group, wherein the cyclic group is optionally substituted by halo, cyano, alkyl, cycloalkyl, aryl, heteroaryl, or amino, provided that when $R^1$ is taken together with $R^2$ to form a phenyl group, both of $Z^1$ and $Z^2$ are O, and one of $Y^1$-$Y^5$ is N and one of $Y^8$-$Y^{10}$ is N and the remaining $Y^1$-$Y^{10}$ are each CH, then $Y^1$-$Y^5$ are taken together with the amidine substituent to form an amidine substituted pyridine ring that is different than the amidine substituted pyridine ring formed by $Y^8$-$Y^{10}$;
$R^3$ is hydrogen, alkyl, cycloalkyl, aryl, or heteroaryl;
$R^4$ is hydrogen, halo, cycloalkyl, aryl, or heteroaryl;
$R^5$ or $R^6$ is independently hydrogen, alkyl, cycloalkyl, aryl, heteroaryl, amino,
or $R^5$ taken together with $R^6$ forms a saturated or partially unsaturated 3-9 membered ring; and
$R^7$ is independently hydrogen, halo, or amidine (-Am)

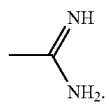

In some variations of formula (A), =====, m, n, p, $Z^1$, $Z^2$, $Y^1$-$Y^{10}$, $R^3$, $R^4$, $R^5$, $R^6$, and $R^7$ are defined as above, and $R^1$ and $R^2$ are each independently hydrogen or halo, or $R^1$ taken together with $R^2$ forms a saturated, unsaturated or partially unsaturated 3-9 membered cyclic group, wherein the cyclic group is optionally substituted by halo, cyano, alkyl, cycloalkyl, aryl, heteroaryl, or amino, provided that when $R^1$ is taken together with $R^2$ to form a saturated, unsaturated or partially unsaturated 6 membered cyclic group, both of $Z^1$ and $Z^2$ are O, and one of $Y^1$-$Y^5$ is N and one of $Y^8$-$Y^{10}$ is N and the remaining $Y^1$-$Y^{10}$ are each CH, then $Y^1$-$Y^5$ are taken together with the amidine substituent to form an amidine substituted pyridine ring that is different than the amidine substituted pyridine ring formed by $Y^8$-$Y^{10}$.

In some embodiments, at least one of $Y^1$-$Y^{10}$ is N. In some embodiments, the ring formed by $Y^1$-$Y^5$ is different than the ring formed by $Y^6$-$Y^{10}$. In some embodiments, the amidine substituted two rings of $Y^1$-$Y^{10}$ are different so that the compound is not symmetrical.

It is thus appreciated that formula (A) excludes the following compounds,
6,6'-(pentane-1,5-diylbis(oxy))dinicotinimidamide;
5,5'-(pentane-1,5-diylbis(oxy))dipicolinimidamide;
4,4'-(pentane-1,5-diylbis(oxy))dipicolinimidamide;
6,6'-(pentane-1,5-diylbis(oxy))dipicolinimidamide;
6,6'-(cyclohexane-1,3-diylbis(oxy))dinicotinimidamide; and
5,5'-(1,4-phenylenebis(oxy))dipicolinimidamide,
or a pharmaceutically acceptable salt thereof.

In some embodiments, the present invention is drawn to compositions of pentamidine analogs having Formula (I):

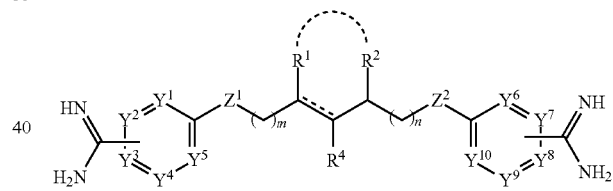

Formula (I)

wherein =====, m, n, p, $Z^1$, $Z^2$, $Y^1$-$Y^{10}$, $R^1$, $R^2$, $R^3$, $R^4$, $R^5$, $R^6$, and $R^7$ are defined in formula (A).

In some embodiments, at least one of $Y^1$-$Y^{10}$ is N. In some embodiments, the ring formed by $Y^1$-$Y^5$ is different than the ring formed by $Y^6$-$Y^{10}$. In some embodiments, the amidine substituted two rings of $Y^1$-$Y^{10}$ are different so that the compound is not symmetrical.

In one embodiment, m is 1, and n is 1. In another embodiment, m is 1, and n is 0. In another embodiment, m is 0, and n is 1. In another embodiment, m is 1, and n is 2. In another embodiment, m is 2, and n is 1. In one embodiment, m is 2, and n is 2. In another embodiment, m is 0, and n is 0.

In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring.

In one embodiment, amidine is independently attached at $Y^3$ and $Y^8$. In another embodiment, amidine is independently attached at $Y^3$ and $Y^7$. In yet another embodiment, amidine is independently attached at $Y^2$ and $Y^7$. In yet another embodiment, amidine is independently attached at $Y^2$ and $Y^7$.

In one embodiment, $Y^{1, 2, 4, 5, 6, 8}$ are $CR^7$ (e.g., —CH); $Y^2$ is N; and $Y^3$ and $Y^7$ attached to amidine. In another embodiment, $Y^{1, 4, 5, 6, \text{ and } 7}$ are —CH; $Y^2$ is N; and $Y^3$ and $Y^8$ are $CR^7$, wherein $R^7$ is amidine. In another embodiment, $Y^{1, 4, 5, 6, \text{ and } 8}$ are —CH; $Y^3$ is N; and $Y^2$ and $Y^7$ are $CR^7$, wherein $R^7$ is amidine. In another embodiment, $Y^{1, 4, 5, 6, \text{ and } 8}$ are —CH; $Y^3$ is N; and $Y^2$ and $Y^7$ are $CR^7$, wherein $R^7$ is amidine, wherein m is 1, and n is 0. In another embodiment, $Y^{1, 4, 5, \text{ and } 6}$ are —CH; $Y^3$ and $Y^8$ are N; and $Y^2$ and $Y^7$ are $CR^7$, wherein $R^7$ is amidine, and wherein m is 1, and n is 0.

In one embodiment, $R^1$ and $R^2$ are independently hydrogen. In another embodiment, $R^1$ taken together with $R^2$ forms a saturated, unsaturated or partially unsaturated 3-9 membered cyclic group (e.g., ). In one specific embodiment, $R^1$ taken together with $R^2$ forms 5 membered cycloalkyl. In another specific embodiment, $R^1$ taken together with $R^2$ forms 6 membered cycloalkyl. In yet another specific embodiment, $R^1$ taken together with $R^2$ forms 7 membered cycloalkyl.

DETAILED DESCRIPTION

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. The use of the term "including," as well as other forms of the term, such as "includes" and "included," is not limiting.

As used herein, "a" or "an" means "at least one" or "one or more."

As used herein, "or" means "and/or."

As used herein, the term "alkyl" refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tert-butyl, pentyl, isopentyl, hexyl, cyclopropylmethyl, and the like. Alkyl groups can be unsubstituted, or they can be substituted to the extent that such substitution is chemically feasible. Typical substituents include, but are not limited to, halo, =O, =N—CN, =N—$OR^a$, =$NR^a$, —$OR^a$, —$NR^a_2$, —$SR^a$, —$SO_2R^a$, —$SO_2NR^a_2$, —$NR^aSO_2R^a$, —$NR^a$-$CONR^a_2$, —$NR^aCOOR^a$, —$NR^aCOR^a$, —$NO_2$, —CN, —$COOR^a$, —$CONR^a_2$, —$OOCR^a$, —$COR^a$, and —$R^a$, wherein each $R^a$ is independently H, $C_1$-$C_8$ alkyl, $C_2$-$C_8$ heteroalkyl, $C_3$-$C_8$ heterocyclyl, $C_4$-$C_{10}$ heterocycloalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each $R^a$ is optionally substituted with halo, =O, =N—CN, =N—$OR^b$, =$NR^b$, —$OR^b$, —$NR^b_2$, —$SR^b$, —$SO_2R^b$, —$SO_2NR^b_2$, —$NR^bSO_2R^b$, —$NR^bCONR^b_2$, —$NR^bCOOR^b$, —$NR^bCOR^b$, —$NO_2$, —CN, —$COOR^b$, —$CONR^b_2$, —$OOCR^b$, —$COR^b$, and —$R^b$, wherein each $R^b$ is independently H, $C_1$-$C_8$ alkyl, $C_2$-$C_8$ heteroalkyl, $C_3$-$C_8$ heterocyclyl, $C_4$-$C_{10}$ heterocycloalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group. Where a substituent group contains two $R^a$ or $R^b$ groups on the same or adjacent atoms (e.g., —$NR^b_2$, or —$NR^b$—$C(O)R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

As used herein, the term "alkenyl" refers to hydrocarbon chain having at least two carbon atoms and at least one carbon-carbon double bond and includes straight, branched, or cyclic alkenyl groups having two to ten carbon atoms. Non-limiting examples of "alkenyl" include ethenyl, propenyl, butenyl, pentenyl, and cyclic alkenyl groups. An alkenyl can be unsubstituted or substituted with one or more suitable substituents.

As used herein, the term "alkynyl" refers to unbranched and branched hydrocarbon moieties having at least two (preferably three) carbon atoms and at least one carbon-carbon triple bond and includes ethynyl, propynyl, butynyl, cyclopropylethynyl, and the like. An alkynyl can be unsubstituted or substituted with one or more suitable substituents.

As used herein, the term "alkoxy" refers to the alkyl groups above bound through oxygen, examples of which include methoxy, ethoxy, propyloxy, isopropoxy, tert-butoxy, methoxyethoxy, benzyloxy, allyloxy, and the like. In addition, alkoxy also refers to polyethers such as —O—$(CH_2)_2$—O—$CH_3$, and the like. An alkoxy can be any hydrocarbon group connected through an oxygen atom wherein the hydrocarbon portion may have any number of carbon atoms, typically 1-10 carbon atoms, may further include a double or triple bond and may include one or two oxygen, sulfur or nitrogen atoms in the alkyl chains. An alkoxy can be unsubstituted or substituted with one or more suitable substituents, e.g., aryl, heteroaryl, cycloalkyl, and/or heterocyclyl.

As used herein, the term "cycloalkyl" refers to cyclic alkane in which a chain of carbon atoms of a hydrocarbon forms a ring, and includes a monocyclic or polycyclic hydrocarbon ring group, for example, cyclopropyl, cyclobutyl, cyclopentyl, cyclohexyl, cycloheptyl, cyclooctyl, cyclodecyl, adamantyl, norpinanyl, decalinyl, norbornyl, housanyl, and the like. Further, a cycloalkyl can also include one or two double bonds, which form the "cycloalkenyl" groups (e.g., cyclopropenyl, cyclobutenyl, cyclopentenyl, cyclohexenyl, cycloheptenyl, cyclooctenyl, norbornenyl, norbornadienyl, and the like). A cycloalkyl can also comprise one or more heteroatoms and referred to as "cycloheteroalkyl" and can include, for example, piperazinyl piperidinyl, morpholinyl, thiomorpholinyl, oxanyl, dioxanyl (e.g., 1,4-dioxanyl), thianyl, dithianyl, hexahydro-1,3,5-triazinyl, trioxanyl, trithianyl, pyrrolidinyl, imidazolidinyl, pyranyl, tetrahydropyranyl, pyrazolidinyl, oxolanyl, oxazolidinyl, thiolanyl, thiazolidinyl, pyrrolinyl, pyrazolinyl, imidazolinyl, tetrahydrofuranyl, and the like. A cycloalkyl or cycloheteroalkyl group can be unsubstituted or substituted with one or more suitable substituents.

As used herein, the term "amidine" or "Am" refers to a group of —CNH$_2$NH as shown in the following structure:

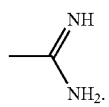

As used herein, the term "hetero" refers to an atom of any element other than carbon or hydrogen. As used herein, the term "heteroatom" means nitrogen (N), oxygen (O), or sulfur (S).

As used herein, the term "heterocycle" or "heterocyclyl" encompasses all limitations of "cycloheteroalkyl" and "heteroaryl" groups in so far as chemically feasible. The term "heterocycle" or "heterocyclyl" refers to any compound in which a plurality of atoms forms a ring via a plurality of covalent bonds, wherein the ring includes at least one atom other than a carbon atom as a ring member. A heterocycle can be saturated, unsaturated, or partially unsaturated. An unsaturated heterocycle can be aromatic aryl. Non-limiting examples of a heterocyclic ring include 3-, 4-, 5-, 6-, 7-, 8- and 9-membered monocyclic rings containing one or more N, O, or S as the non-carbon member(s) and are as follows: (1) a saturated 3 atom heterocyclic ring can be, for example, aziridinyl, diaziridinyl, oxiranyl, dioxiranyl, oxaziridinyl, thiiranyl, or the like, and an unsaturated 3 atom heterocyclic ring can be, for example, azirinyl, oxirenyl, thiirenyl, diazirinyl, or the like; (2) a saturated 4 atom heterocyclic ring can be, for example, azetidinyl, diazetidinyl, oxetanyl, dioxetanyl, thietanyl, dithietanyl, or the like, and an unsaturated 4 atom heterocyclic ring can be, for example, azetyl, diazetyl, oxetyl, dioxetyl, thietyl, dithietyl, or the like; (3) a saturated 5 atom heterocyclic ring can be, for example, pyrrolidinyl, imidazolidinyl, pyrazolidinyl, oxolanyl, oxazolidinyl, thiolanyl, thiazolidinyl, or the like, and an unsaturated and partially unsaturated 5 atom heterocyclic ring can be, for example, pyrrolyl, pyrrolinyl, pyrazolyl, pyrazolinyl, imidazolyl, imidazolinyl, triazolyl, tetrazolyl, thiophenyl, thiazolyl, dithiazolyl, thiazolinyl, isothiazolyl, thiadiazolyl, furanyl, furazanyl, oxazolyl, isoxazolyl, oxadiazolyl, or the like; (4) a saturated 6 atom heterocyclic ring can be, for example, piperidinyl, piperazinyl, morpholinyl, thiomorpholinyl, oxanyl, dioxanyl (e.g., 1,4-dioxacyclohexane), thianyl, dithianyl, hexahydro-1,3,5-triazinyl, trioxanyl, trithianyl, or the like, and an unsaturated 6 atom heterocyclic ring can be, for example, pyridinyl, diazinyl (e.g., pyrimidinyl, or pyridazinyl), pyranyl, oxazinyl (e.g., 1,2-oxazinyl; 1,3-oxazinyl, or 1,4-oxazinyl), thiazinyl, 1,4-dioxinyl, dithiinyl, triazinyl (e.g., 1,2,3-triazinyl, 1,2,4-triazinyl, or 1,3,5-triazinyl), tetrazinyl, pentazinyl, thiopyranyl, or the like; (5) a saturated 7 atom heterocyclic ring can be, for example, azepanyl, diazepanyl, oxepanyl, thiepanyl, or the like, and an unsaturated 7 atom heterocyclic ring can be, for example, azepinyl, diazepinyl, oxepinyl, thiepinyl, thiazepinyl, or the like; (6) a saturated 8 atom heterocyclic ring can be, for example, azocanyl, oxocanyl, thiocanyl, or the like, and an unsaturated 8 atom heterocyclic ring can be, for example, azocinyl, oxocinyl, thiocinyl, or the like; and (7) a saturated 9 atom heterocyclic ring can be, for example, azonanyl, oxonanyl, thionanyl, or the like, and an unsaturated 9 atom heterocyclic ring can be, for example, azoninyl, oxoninyl, thioninyl, or the like. Further contemplated heterocycles may be fused, for example, covalently bound with two atoms on the first non-heterocyclic group (e.g., phenyl) to one or two heterocycles (e.g., 1,4-dioxanyl, 1,4-dioxinyl, and tetrahydropyranyl), or covalently bound with two atoms on the first heterocyclic ring (e.g., pyrrolyl, imidazolyl, thiazolyl, pyrimidinyl, and pyridinyl) to one or two nonheterocyclic or heterocyclic group (e.g., 1,4-dioxanyl, 1,4-dioxinyl, and morpholinyl), and taken together are thus termed "fused heterocycle" or "fused heterocyclic moieties" or "heteroaryl-fused-cycloheteroalkyl" as used herein. The fused heterocycle can be, for example, a saturated or unsaturated (e.g., aromatic) bicyclic or tricyclic compound. Non-limiting examples of fused heterocycle include dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, indolyl, purinyl, isoindolyl, quinolinyl, isoquinolinyl, quinoxalinyl, quinazolinyl, quinolizinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, acridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzoxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, fluorenyl, and the like. Where the heterocyclic ring is aromatic, it can be also referred to herein as "heteroaryl" or "heteroaromatic" as described further below. A heterocyclic ring that is not aromatic can be substituted with any group suitable for alkyl group substituents described above.

As used herein, the term "aryl" refers to unsubstituted or substituted aromatic monocyclic or polycyclic groups, which may further include one or more non-carbon atoms. The term "aryl" also includes aromatic rings fused to non-aromatic carbocyclic ring, or to a heterocyclyl group having 1-7 heteroatoms. The term "aryl" may be interchangeably used with "aryl ring," "aromatic group," and "aromatic ring." An aryl group may contain 1-9 heteroatom(s) that are generally referred to as "heteroaryl." Heteroaryl groups typically have 4 to 14 atoms, 1 to 9 of which are independently selected from the group consisting of N, O, and S. In a 5-8 membered aromatic group, for example, a heteroaryl group can contain 1-4 heteroatoms. An aryl or heteroaryl can be unsubstituted or substituted with one or more suitable substituents.

An aryl or heteroaryl can be a mono- or polycyclic (e.g., bicyclic) aromatic group. Typical aryl groups include, for example, phenyl and naphthalenyl and the like. Typical heteroaryl groups include, for example, quinolinyl, pyrrolyl, pyrazolyl, imidazolyl, triazolyl, tetrazolyl, thiophenyl, thiazolyl, dithiazolyl, thiazolinyl, isothiazolyl, thiadiazolyl, furanyl, furazanyl, oxazolyl, isoxazolyl, oxadiazolyl, pyridinyl, diazinyl (e.g., pyrazinyl, pyrimidinyl, or pyridazinyl), triazinyl (e.g., 1,2,3-triazinyl, 1,2,4-triazinyl, or 1,3,5-triazinyl), pyranyl, oxazinyl (e.g., 1,2-oxazinyl; 1,3-oxazinyl, or 1,4-oxazinyl), thiazinyl, dioxinyl, dithiinyl, triazinyl, tetrazinyl, pentazinyl, thiopyranyl, azepinyl, diazepinyl, oxepinyl, thiepinyl, thiazepinyl, azocinyl, oxocinyl, thiocinyl, azoninyl, oxoninyl, thioninyl, indolyl, indazolyl, purinyl, isoindolyl, quinolinyl, isoquinolinyl, quinoxalinyl, acridinyl, quinazolinyl, cinnolinyl, phthalazinyl, benzimidazolyl, benzofuranyl, isobenzofuranyl, benzoxazolyl, benzisoxazolyl, benzothiazolyl, or the like. Polycyclic aryl or polycyclic heteroaryl groups can be formed by fusing (i.e., covalently bonding) 2 atoms on the first aryl or heteroaryl ring with at least one carbocyclic or heterocyclic group, and are thus termed "fused aryl" or "heteroaryl-fused-cycloheteroalkyl."

As used herein, the term "heteroaryl-fused-cycloheteroalkyl" refers to a heterocyclyl moiety consisting of a monocyclic heteroaryl group, such as pyridinyl or furanyl, fused to a cycloheteroalkyl group, in which the heteroaryl and cycloheteroalkyl parts are as defined herein. Exemplary heteroaryl-fused-heterocycloalkyl groups include dihydrodioxinopyridinyl, dihydrodioxinopyridazinyl, dihydrodioxinopyrimidinyl, dihydrodioxinopyrazinyl, dihydrodioxinotriazinyl, dihydropyrrolopyridinyl, dihydrofuranopyridinyl and dioxolopyridinyl. The heteroaryl-fused-heterocycloalkyl group may be attached to the remainder of the molecule by any available carbon or nitrogen atom.

Typical heteroaryl groups include 5 or 6 membered monocyclic aromatic groups such as pyridinyl, pyrimidyl, pyrazinyl, pyridazinyl, thienyl, furanyl, pyrrolyl, pyrazolyl, thiazolyl, oxazolyl, isothiazolyl, isoxazolyl, thiophenyl, triazolyl (1,2,4-triazolyl and 1,2,3-triazolyl), tetrazolyl, furazanyl, oxadiazolyl (1,2,5-oxadiazolyl and 1,2,3-oxadiazolyl), and imidazolyl and the fused bicyclic moieties formed by fusing one of heterocyclic groups with a phenyl ring or with any of the heteroaromatic monocyclic groups include indolyl, benzimidazolyl, indazolyl, benzotriazolyl, isoquinolyl, quinolyl, benzothiazolyl, benzofuranyl, pyrazolopyridinyl, pyrazolopyrimidyl, quinazolinyl, quinoxalinyl, cinnolinyl, imidazopyrimidinyl, and the like.

As used herein, the term "monocyclic" refers to an unsubstituted or substituted single ring structure. As used herein, the terms "polycyclic" and "bicyclic" refer to an unsubstituted or substituted poly-ring structure that comprises at least two ring structures fused by any two adjacent atoms. A bicyclic ring can be an aryl or heteroaryl ring fused to an aromatic ring or a non-aromatic carbocyclic ring such as cycloalkyl or cycloheteroalkyl. A bicyclic ring can be also non-aromatic carbocyclic ring fused to another non-aromatic carbocyclic ring such as cycloalkyl or cycloheteroalkyl. Non-limiting examples of bicyclic rings include dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, decalinyl, purinyl, indolyl, isoindolyl, quinolyl, quinazolinyl, benzimidazolyl, imidazopyridinyl, cinnolinyl, phthalazinyl, imidazopyrimidinyl, and the like. Any monocyclic or fused bicyclic system which has the characteristics of aromaticity in terms of electron distribution throughout the ring system is included in this definition. It also includes bicyclic groups where at least the ring which is directly attached to the remainder of the molecule has the characteristics of aromaticity.

Aryl and heteroaryl groups can be substituted where permitted. Suitable substituents include, but are not limited to, halo, $R^a$, —$OR^a$, —$NR^a_2$, —$SR^a$, —$SO_2R^a$, —$SO_2NR^a_2$, —$NR^aSO_2R^a$, —$NR^aCONR^a_2$, —$NR^a\text{-}COOR^a$, —$NR^aCOR^a$, —CN, —$COOR^a$, —$CONR^a_2$, —$OOCR^a$, —$COR^a$, and —$NO_2$, wherein each $R^a$ is independently H, $C_1$-$C_8$ alkyl, $C_2$-$C_8$ heteroalkyl, $C_3$-$C_8$ heterocyclyl, $C_4$-$C_{10}$ heterocycloalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each $R^a$ is optionally substituted with halo, =O, =N—CN, =N—$OR^b$, =$NR^b$, —$OR^b$, —$NR^b_2$, —$SR^b$, —$SO_2R^b$, —$SO_2NR^b_2$, —$NR^bSO_2R^b$, —$NR^bCONR^b_2$, —$NR^bCO$-$OR^b$, —$NR^bCOR^b$, —CN, —$COOR^b$, —$CONR^b_2$, —$OOCR^b$, —$COR^b$, and —$NO_2$, wherein each $R^b$ is independently H, $C_1$-$C_8$ alkyl, $C_2$-$C_8$ heteroalkyl, $C_3$-$C_8$ heterocyclyl, $C_4$-$C_{10}$ heterocycloalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group. Where a substituent group contains two $R^a$ or $R^b$ groups on the same or adjacent atoms (e.g., —$NR^b_2$, or —$NR^b$—$C(O)R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein each alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

As used herein, the term "acyl" when used without the "substituted" modifier refers to the group —C(O)R, in which R is a hydrogen, alkyl, aryl, halides, aralkyl or heteroaryl, as those terms are defined herein.

As used herein, the term "acyloxy" refers a straight-chain or branched alkanoyl group having 1 to 6 carbon atoms, such as formyl, acetyl, propanoyl, butyryl, valeryl, pivaloyl and hexanoyl, and arylcarbonyl group described below, or a heteroarylcarbonyl group described below. The aryl moiety of the arylcarbonyl group means a group having 6 to 16 carbon atoms such as phenyl, biphenyl, naphthyl, or pyrenyl. The heteroaryl moiety of the heteroarylcarbonyl group contains at least one hetero atom from O, N, and S, such as pyridinyl, pyrimidyl, pyrroleyl, furyl, benzofuryl, thienyl, benzothienyl, imidazolyl, triazolyl, quinolyl, iso-quinolyl, benzoimidazolyl, thiazolyl, benzothiazolyl, oxazolyl, and indolyl.

As used herein, the term "carboxylic acid" refers to a group —C(O)OH.

As used herein, the term "ester," as used herein, refers to a group —C(O)O—.

As used herein, the term "nitro" means —$NO_2$.

As used herein, the term "cyano" means —CN.

As used herein, the term "azido" means relating to a monovalent group containing —$N_3$.

As used herein, the term "sulfhydryl" means thiol, —SH.

As used herein, the term "amine" means primary, secondary and tertiary amines, —R—$NH_2$, —R—NH—R', and —R—N—(R")R', respectively.

As used herein, the term "amide" means primary, secondary and tertiary amides, —R—C(O)$NH_2$, —R—C(O)NH—R', and —R—C(O)NR'R", respectively.

As used herein, the term "carbonate" means ester of carbonic acid, a group containing C(=O)(O—)$_2$.

As used herein, the term "carbamate" means a group containing $NH_2COOH$.

As used herein, the term "hydroxyl" means —OH.

As used herein, the terms "halo," "halogen," and "halide" mean fluoro (—F), chloro (—Cl), bromo (—Br), and iodo (—I).

As used herein, the term "haloalkyl" refers to any alkyl having one or more hydrogen atoms replaced by one or more halogen atoms. Non-limiting examples of haloalkyl include —CF$_3$, —CFH$_2$, —CF$_2$H, and the like.

As used herein, the term "arylalkyl" refers to any alkyl in which one or more hydrogen atoms are replaced by an aryl or heteroaryl group. Examples of arylalkyl include benzyl (C$_6$H$_5$CH$_2$—) and the like.

As used herein, the term "hydroxyalkyl" refers to any hydroxy derivative of alkyl and includes any alkyl having one or more hydrogen atoms replaced by a —OH group.

The term "haloalkyl" refers to an alkyl group as described above with one or more hydrogen atoms on the alkyl group substituted with a halo group. Examples of such groups include, without limitation, fluoroalkyl groups, such as fluoroethyl, difluoromethyl, trifluoromethyl, trifluoroethyl and the like.

The term "haloalkoxy" refers to the group alkyl-O— with one or more hydrogen atoms on the alkyl group substituted with a halo group (e.g., —F, —Cl, —Br, and —I) and include, for example, groups such as trifluoromethoxy and the like.

The term "substituted" as used herein refers to a replacement of a hydrogen atom of the unsubstituted group with a functional group, and particularly contemplated functional groups include nucleophilic groups (e.g., —NH$_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —NH$_3^+$), and halogens (e.g., —F, —Cl), NHCOR, NHCONH$_2$, OCH$_2$COOH, OCH$_2$CONH$_2$, OCH$_2$CONHR, NHCH$_2$COOH, NHCH$_2$CONH$_2$, NHSO$_2$R, OCH$_2$-heterocycles, PO$_3$H, SO$_3$H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

Unless indicated otherwise, the nomenclature of substituents that are not explicitly defined herein are arrived at by naming the terminal portion of the functionality followed by the adjacent functionality toward the point of attachment. For example, the substituent "alkylaryloxycarbonyl" refers to the group (alkyl)-(aryl)-O—C(O)—.

As to any of the groups disclosed herein which contain one or more substituents, it is understood that such groups do not contain any substitution or substitution patterns which are sterically impractical and/or synthetically non-feasible. In addition, the subject compounds include all stereochemical isomers arising from the substitution of these compounds.

In addition to the disclosure herein, in a certain embodiment, a group that is substituted has 1 substituent, 1 or 2 substituents, 1, 2, or 3 substituents, or 1, 2, 3, or 4 substituents.

As used herein, the term "administration" or "administering" of the subject compound refers to providing a compound of the invention to a subject in need of treatment.

As used herein, the term "acceptable" with respect to a formulation, composition or ingredient, as used herein, means having no persistent detrimental effect on the general health of the subject being treated.

The term "about" when referring to a number or a numerical range means that the number or numerical range referred to is an approximation within experimental variability (or within statistical experimental error), and thus the number or numerical range may vary from, for example, between 1% and 10% of the stated number or numerical range.

As used herein, the term "carrier" refers to chemical compounds or agents that facilitate the incorporation of a compound described herein into cells or tissues.

As used herein, the terms "comprise," "have," and "include" are open-ended linking verbs. Any forms or tenses of one or more of these verbs, such as "comprises," "comprising," "has," "having," "includes," and "including" are open-ended. For example, any method that "comprises," "has," or "includes" one or more moieties is not limited to possessing only those one or more moieties and also covers other unlisted moieties.

A "pharmaceutically acceptable salt" is a salt formed from an acid and a basic group of pentamidine analogs. Examples of such salts include acid addition salts and base addition salts, such as inorganic acid salts or organic acid salts (e.g., hydrochloric acid salt, dihydrochloric acid salt, sulfuric acid salt, citrate, hydrobromic acid salt, hydroiodic acid salt, nitric acid salt, bisulfate, phosphoric acid salt, super phosphoric acid salt, isonicotinic acid salt, acetic acid salt, lactic acid salt, salicylic acid salt, tartaric acid salt, pantothenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate)), as well as salts of aluminum, calcium, lithium, magnesium, calcium, sodium, zinc, and diethanolamine. It is to be understood that reference to a pentamidine analog or a pharmaceutically acceptable salt thereof, includes pharmaceutically acceptable salts of compound disclosed herein. Examples of such pharmaceutically acceptable salts include, but are not limited to, isethionate, gluconate, and mesylate.

As used herein, the term "hydrogen" refers to a hydrogen atom (—H) and deuterium (heavy hydrogen, non-radioactive isotope of hydrogen, D or $^2$H). It is to be understood that the present invention contemplates deuterated compound versions of all molecules of the present disclosure which can be synthesized by converting a hydrogen atom to $^2$H at a place where a hydrogen atom is present.

Pentamidine Analogs

In one aspect, provided is a compound of formula (A):

Formula (A)

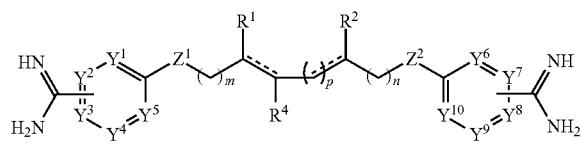

or a pharmaceutically acceptable salt thereof, wherein:
===== represents a single or double bond;
m or n is independently an integer of 0, 1, 2 or 3;
p is 0 or 1;
Z$^1$ or Z$^2$ is independently O, S, SO$_2$, NR$^3$, or CR$^5$R$^6$;
Y$^1$-Y$^{10}$ are each independently N or CR$^7$, wherein at least one of Y$^1$-Y$^{10}$ is N, provided that when the moiety is taken together to form the moiety

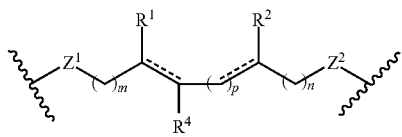

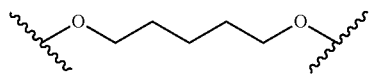 [SMILES: *OCCCCCO*]

one $Y^1$-$Y^5$ is N and one of $Y^8$-$Y^{10}$ is N and the remaining $Y^1$-$Y^{10}$ are each CH, then $Y^1$-$Y^5$ are taken together with the amidine substituent to form an amidine substituted pyridine ring that is different than the amidine substituted pyridine ring formed by $Y^8$-$Y^{10}$;

$R^1$ and $R^2$ are each independently hydrogen or halo, or $R^1$ taken together with $R^2$ forms a saturated, unsaturated or partially unsaturated 3-9 membered cyclic group, wherein the cyclic group is optionally substituted by halo, cyano, alkyl, cycloalkyl, aryl, heteroaryl, or amino, provided that when $R^1$ is taken together with $R^2$ to form a phenyl group, both of $Z^1$ and $Z^2$ are O, and one of $Y^1$-$Y^5$ is N and one of $Y^8$-$Y^{10}$ is N and the remaining $Y^1$-$Y^{10}$ are each CH, then $Y^1$-$Y^5$ are taken together with the amidine substituent to form an amidine substituted pyridine ring that is different than the amidine substituted pyridine ring formed by $Y^8$-$Y^{10}$;

$R^3$ is hydrogen, alkyl, cycloalkyl, aryl, or heteroaryl;

$R^4$ is hydrogen, halo, cycloalkyl, aryl, or heteroaryl;

$R^5$ or $R^6$ is independently hydrogen, alkyl, cycloalkyl, aryl, heteroaryl, amino, or $R^5$ taken together with $R^6$ forms a saturated or partially unsaturated 3-9 membered ring; and $R^7$ is independently hydrogen, halo, or amidine (-Am)

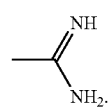

In some variations of formula (A), ═══, m, n, p, $Z^1$, $Z^2$, $Y^1$-$Y^{10}$, $R^3$, $R^4$, $R^5$, $R^6$, and $R^7$ are defined as above, and $R^1$ and $R^2$ are each independently hydrogen or halo, or $R^1$ taken together with $R^2$ forms a saturated, unsaturated or partially unsaturated 3-9 membered cyclic group, wherein the cyclic group is optionally substituted by halo, cyano, alkyl, cycloalkyl, aryl, heteroaryl, or amino, provided that when $R^1$ is taken together with $R^2$ to form a saturated, unsaturated or partially unsaturated 6 membered cyclic group, both of $Z^1$ and $Z^2$ are O, and one of $Y^1$-$Y^5$ is N and one of $Y^8$-$Y^{10}$ is N and the remaining $Y^1$-$Y^{10}$ are each CH, then $Y^1$-$Y^5$ are taken together with the amidine substituent to form an amidine substituted pyridine ring that is different than the amidine substituted pyridine ring formed by $Y^8$-$Y^{10}$.

In some embodiments, at least one of $Y^1$-$Y^{10}$ is N. In some embodiments, the ring formed by $Y^1$-$Y^5$ is different than the ring formed by $Y^6$-$Y^{10}$. In some embodiments, the amidine substituted two rings of $Y^1$-$Y^{10}$ are different so that the compound is not symmetrical.

In some embodiments, the moiety

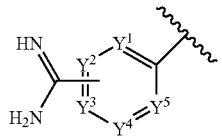

is selected from the group consisting of

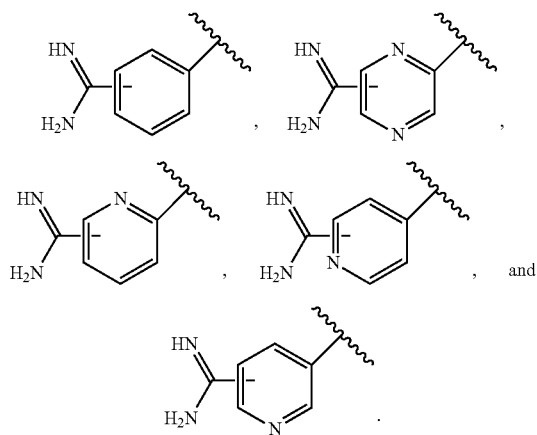

, and

In some embodiments, the moiety

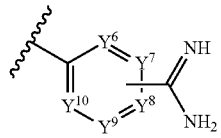

is selected from the group consisting of

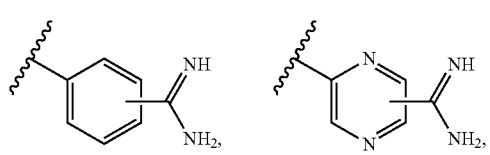

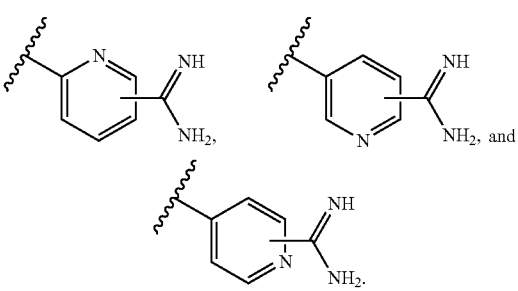

In some embodiments, the moiety

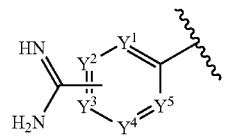

is selected from the group consisting of

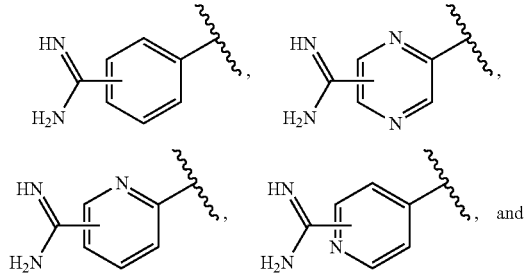

and the moiety

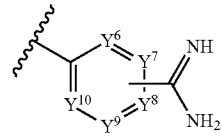

is selected from the group consisting of

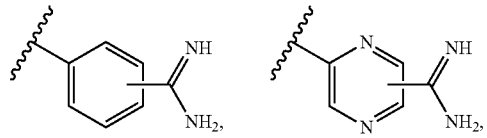

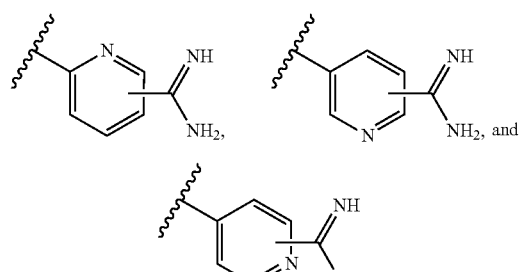

In some embodiments,

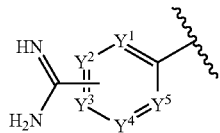

is selected from the group consisting of

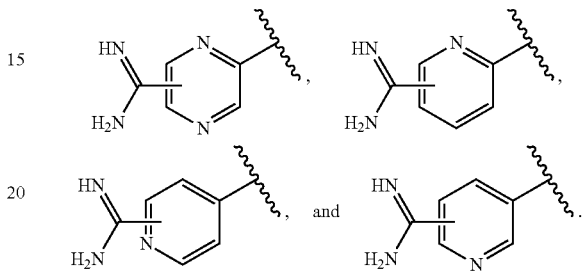

In some embodiments,

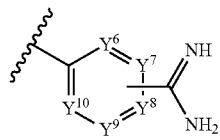

is selected from the group consisting of

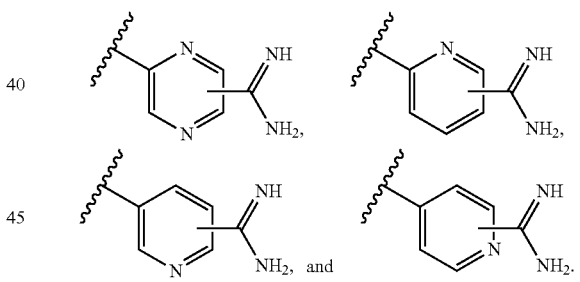

In some embodiments, the amidine substituted two rings of $Y^1$-$Y^{10}$ are different.

In some embodiments, the moiety

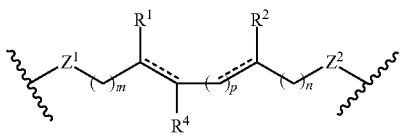

is selected from the group consisting of

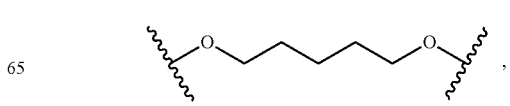

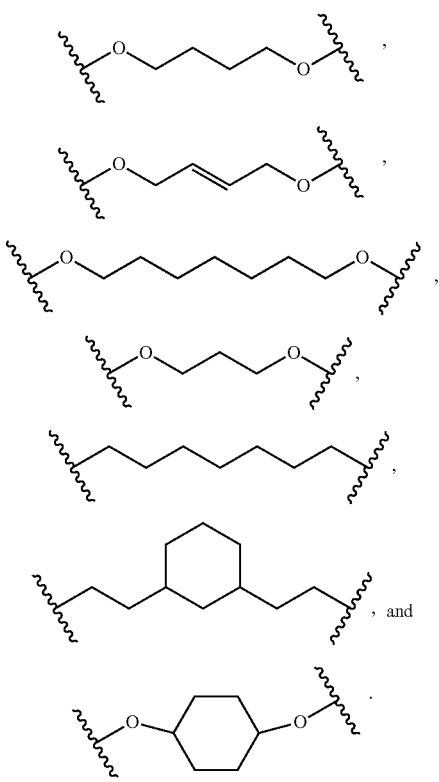
In some embodiments, the moiety
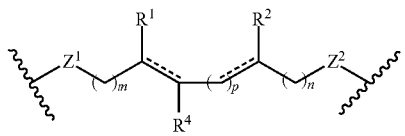
is selected from the group consisting of
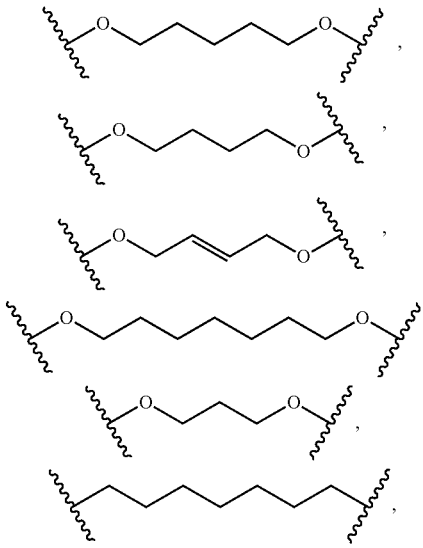
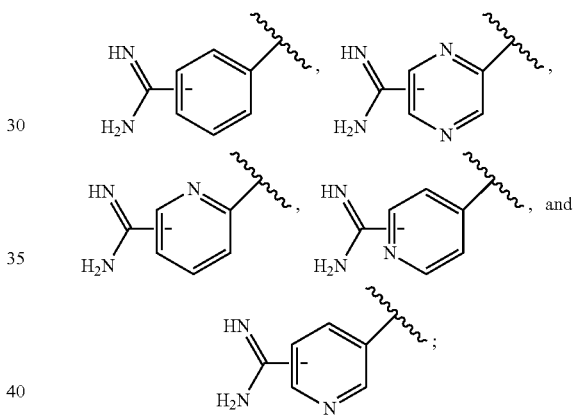
the moiety
is selected from the group consisting of
and the moiety
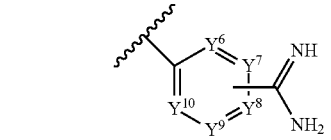
is selected from the group consisting of
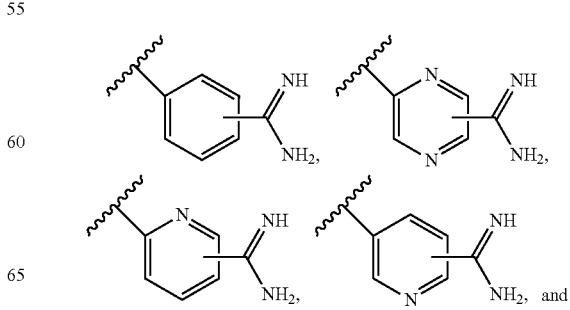

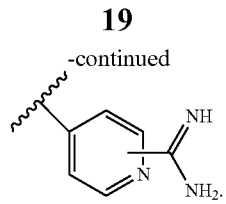

In some embodiments, the amidine substituted two rings of $Y^1$-$Y^{10}$ are different so the compound is not symmetrical.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to R of formula (A) or (I)-(VIII) may be combined with every description, variation, embodiment or aspect of Y, X, n, m, and/or p the same as if each and every combination were specifically and individually listed. It is also understood that all descriptions, variations, embodiments or aspects of formula (A) or (I)-(VIII), where applicable, apply equally to other formulae detailed herein, and are equally described, the same as if each and every description, variation, embodiment or aspect were separately and individually listed for all formulae. For example, all descriptions, variations, embodiments or aspects of formula (A), where applicable, apply equally to any applicable formulae herein, such as formulae (I)-(VIII), as detailed herein, and are equally described, the same as if each and every description, variation, embodiment or aspect were separately and individually listed for all formulae.

In some embodiments, provided are heteroaryl diamidine compounds of Formula (I) or pharmaceutically acceptable salts thereof:

Formula (I)

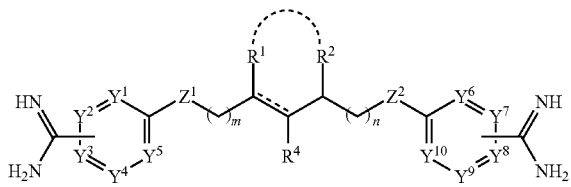

wherein ====, m, n, $Z^1$, $Z^2$, $Y^1$-$Y^{10}$, $R^1$, $R^2$, $R^3$, $R^4$, $R^5$, $R^6$, and $R^7$ are defined in formula (A).

In some embodiments, at least one of $Y^1$-$Y^{10}$ is N. In some embodiments, the ring formed by $Y^1$-$Y^5$ is different than the ring formed by $Y^6$-$Y^{10}$. In some embodiments, the amidine substituted two rings of $Y^1$-$Y^{10}$ are different so that the compound is not symmetrical.

In one embodiment, m is 1, and n is 1. In another embodiment, m is 1, and n is 0. In another embodiment, m is 0, and n is 1. In another embodiment, m is 1, and n is 2. In another embodiment, m is 2, and n is 1. In one embodiment, m is 2, and n is 2. In another embodiment, m is 0, and n is 0.

In one embodiment, $Z^1$ or $Z^2$ is independently selected from the group consisting of O, N, and S, each of which can be optionally substituted. In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring.

In one embodiment, amidine is independently attached at $Y^3$ and $Y^8$. In another embodiment, amidine is independently attached at $Y^3$ and $Y^7$. In yet another embodiment, amidine is independently attached at $Y^2$ and $Y^7$. In yet another embodiment, amidine is independently attached at $Y^2$ and $Y^7$.

In one embodiment, $Y^{1, 2, 4, 5, 6, 8}$ are $CR^7$ (e.g., —CH); $Y^2$ is N; and $Y^3$ and $Y^7$ attached to amidine. In another embodiment, $Y^{1, 4, 5, 6, and 7}$ are —CH; $Y^2$ is N; and $Y^3$ and $Y^8$ are $CR^7$, wherein $R^7$ is amidine. In another embodiment, $Y^{1, 4, 5, 6, and 8}$ are —CH; $Y^3$ is N; and $Y^2$ and $Y^7$ are $CR^7$, wherein $R^7$ is amidine. In another embodiment, $Y^{1, 4, 5, 6, and 8}$ are —CH; $Y^3$ is N; and $Y^2$ and $Y^7$ are $CR^7$, wherein $R^7$ is amidine, wherein m is 1, and n is 0. In another embodiment, $Y^{1, 4, 5, and 6}$ are —CH; $Y^3$ and $Y^8$ are N; and $Y^2$ and $Y^7$ are $CR^7$, wherein $R^7$ is amidine, and wherein m is 1, and n is 0.

In one embodiment, $R^1$ and $R^2$ are independently hydrogen. In another embodiment, $R^1$ taken together with $R^2$ forms a saturated, unsaturated or partially unsaturated 3-9 membered cyclic group (e.g., ⌒). In one specific embodiment, $R^1$ taken together with $R^2$ forms 5 membered cycloalkyl. In another specific embodiment, $R^1$ taken together with $R^2$ forms 6 membered cycloalkyl. In yet another specific embodiment, $R^1$ taken together with $R^2$ forms 7 membered cycloalkyl.

In one embodiment, $R^3$ is hydrogen. In another embodiment, $R^3$ is alkyl. For example, $R^3$ can be methyl or ethyl. In another embodiment, $R^3$ is cycloalkyl. In another embodiment, $R^3$ is aryl. In yet another embodiment, $R^3$ is heteroaryl.

In one embodiment, $R^4$ is hydrogen. In another embodiment, $R^4$ is halo. In yet another embodiment, $R^4$ is cycloalkyl. In yet another embodiment, $R^4$ is aryl. In yet another embodiment, $R^4$ is heteroaryl. In one specific embodiment, $R^4$ is phenyl. In one embodiment, $R^5$ or $R^6$ is independently hydrogen, alkyl, cycloalkyl, aryl, heteroaryl, amino, or $R^5$ taken together with $R^6$ forms a saturated or partially unsaturated 3-9 membered ring. For example, $R^5$ and $R^6$ can be hydrogen. In one embodiment, $R^7$ is independently hydrogen or halo.

In some embodiments, the present invention is drawn to compounds having Formula (II) or pharmaceutically acceptable salts thereof:

Formula (II)

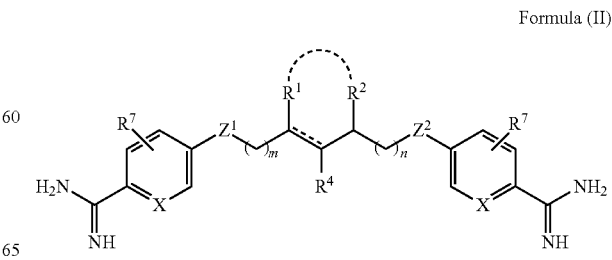

wherein ≡, m, n, $Z^1$, $Z^2$, $R^1$, $R^2$, $R^3$, $R^4$, $R^5$, and $R^6$, are defined in formula (A), X is independently N or $CR^7$; and $R^7$ is independently hydrogen or halo.

In some embodiments, at least one X is N. In some embodiments, the amidine substituted two rings are different so that the compound is not symmetrical.

In one embodiment, m is 1, and n is 1. In another embodiment, m is 1, and n is 0. In another embodiment, m is 0, and n is 1. In another embodiment, m is 1, and n is 2. In another embodiment, m is 2, and n is 1. In one embodiment, m is 2, and n is 2. In another embodiment, m is 0, and n is 0.

In one embodiment, both Xs are N. In another embodiment, only X is N or the other X is $CR_7$.

In one embodiment, $Z^1$ or $Z^2$ is independently selected from the group consisting of O, N, and S, each of which can be optionally substituted. In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring.

In one embodiment, $R^1$ and $R^2$ are independently hydrogen. In another embodiment, $R^1$ taken together with $R^2$ forms a saturated, unsaturated or partially unsaturated 3-9 membered cyclic group (e.g., ⌒). In one specific embodiment, $R^1$ taken together with $R^2$ forms 5 membered cycloalkyl. In another specific embodiment, $R^1$ taken together with $R^2$ forms 6 membered cycloalkyl. In yet another specific embodiment, $R^1$ taken together with $R^2$ forms 7 membered cycloalkyl. In one embodiment, $R^3$ is hydrogen. In another embodiment, $R^3$ is alkyl. For example, $R^3$ can be methyl or ethyl. In another embodiment, $R^3$ is cycloalkyl. In another embodiment, $R^3$ is aryl. In yet another embodiment, $R^3$ is heteroaryl. In one embodiment, $R^4$ is hydrogen. In another embodiment, $R^4$ is halo. In yet another embodiment, $R^4$ is cycloalkyl. In yet another embodiment, $R^4$ is aryl. In yet another embodiment, $R^4$ is heteroaryl. In one specific embodiment, $R^4$ is phenyl. In one embodiment, $R^5$ or $R^6$ is independently hydrogen, alkyl, cycloalkyl, aryl, heteroaryl, amino, or $R^5$ taken together with $R^6$ forms a saturated or partially unsaturated 3-9 membered ring. For example, $R^5$ and $R^6$ can be hydrogen. In one embodiment, $R^7$ is independently hydrogen or halo.

In some embodiments, the present invention is drawn to compounds having Formula (III) or pharmaceutically acceptable salts thereof:

Formula (III)

In some embodiments, the present invention is drawn to compounds having Formula (IV) or pharmaceutically acceptable salts thereof:

Formula (IV)

wherein =====, m, n, $Z^1$, $Z^2$, $R^1$, $R^2$, $R^3$, $R^4$, $R^5$, and $R^6$, are defined in formula (A), X is independently N or $CR^7$; and $R^7$ is independently hydrogen or halo.

In some embodiments, the amidine substituted two rings are different so that the compound is not symmetrical.

In one embodiment, m is 1, and n is 1. In another embodiment, m is 1, and n is 0. In another embodiment, m is 0, and n is 1. In another embodiment, m is 1, and n is 2. In another embodiment, m is 2, and n is 1. In one embodiment, m is 2, and n is 2. In another embodiment, m is 0, and n is 0.

In one embodiment, both Xs are N. In another embodiment, only X is N or the other X is $CR_7$.

In one embodiment, $Z^1$ or $Z^2$ is independently selected from the group consisting of O, N, and S, each of which can be optionally substituted. In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring.

In one embodiment, $R^1$ and $R^2$ are independently hydrogen. In another embodiment, $R^1$ taken together with $R^2$ forms a saturated, unsaturated or partially unsaturated 3-9 membered cyclic group (e.g., 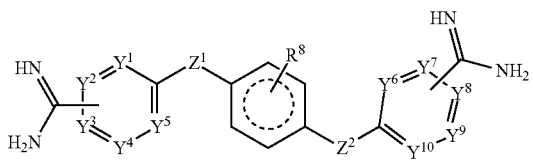). In one specific embodiment, $R^1$ taken together with $R^2$ forms 5 membered cycloalkyl. In another specific embodiment, $R^1$ taken together with $R^2$ forms 6 membered cycloalkyl. In yet another specific embodiment, $R^1$ taken together with $R^2$ forms 7 membered cycloalkyl. In one embodiment, $R^3$ is hydrogen. In another embodiment, $R^3$ is alkyl. For example, $R^3$ can be methyl or ethyl. In another embodiment, $R^3$ is cycloalkyl. In another embodiment, $R^3$ is aryl. In yet another embodiment, $R^3$ is heteroaryl. In one embodiment, $R^4$ is hydrogen. In another embodiment, $R^4$ is halo. In yet another embodiment, $R^4$ is cycloalkyl. In yet another embodiment, $R^4$ is aryl. In yet another embodiment, $R^4$ is heteroaryl. In one specific embodiment, $R^4$ is phenyl. In one embodiment, $R^5$ or $R^6$ is independently hydrogen, alkyl, cycloalkyl, aryl, heteroaryl, amino, or $R^5$ taken together with $R^6$ forms a saturated or partially unsaturated 3-9 membered ring. For example, $R^5$ and $R^6$ can be hydrogen. In one embodiment, $R^7$ is independently hydrogen or halo.

In some embodiments, the present invention is drawn to compounds having Formula (V) or pharmaceutically acceptable salts thereof:

Formula (V)

wherein $Z^1$, $Z^2$, $Y^1$-$Y^{10}$, $R^1$, $R^2$, $R^3$, $R^4$, $R^5$, $R^6$, and $R^7$ are defined in formula (A), $R^8$ is independently hydrogen, halo, cyano, alkyl, cycloalkyl, aryl, heteroaryl, or amino.

In some embodiments, at least one of $Y^1$-$Y^{10}$ is N. In some embodiments, the ring formed by $Y^1$-$Y^5$ is different than the ring formed by $Y^6$-$Y^{10}$. In some embodiments, the amidine substituted two rings of $Y^1$-$Y^{10}$ are different so that the compound is not symmetrical.

In one embodiment, $Z^1$ or $Z^2$ is independently selected from the group consisting of O, N, and S, optionally substituted. In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring. In another embodiment, $Z^1$ and $Z^2$ are $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring.

In one embodiment, amidine is independently attached at $Y^3$ and $Y^8$. In another embodiment, amidine is independently attached at $Y^3$ and $Y^7$. In yet another embodiment, amidine is independently attached at $Y^2$ and $Y^7$. In yet another embodiment, amidine is independently attached at $Y^2$ and $Y^7$.

In one embodiment, $Y^{1, 2, 4, 5, 6, 8}$ are $CR^7$ (e.g., —CH); $Y^2$ is N; and $Y^3$ and $Y^7$ attached to amidine. In another embodiment, $Y^{4, 5, 6, and 7}$ are —CH; $Y^2$ is N; and $Y^3$ and $Y^8$ are $CR^7$, wherein $R^7$ is amidine. In another embodiment, $Y^{1, 4, 5, 6, and 8}$ are —CH; $Y^3$ is N; and $Y^2$ and $Y^7$ are $CR^7$, wherein $R^7$ is amidine. In another embodiment, $Y^{1, 4, 5, 6, and 8}$ are —CH; $Y^3$ is N; and $Y^2$ and $Y^7$ are $CR^7$, wherein $R^7$ is amidine. In another embodiment, $Y^{1, 4, 5, and 6}$ are —CH; $Y^3$ and $Y^8$ are N; and $Y^2$ and $Y^7$ are $CR^7$, wherein $R^7$ is amidine.

In one embodiment, $R^3$ is hydrogen. In another embodiment, $R^3$ is alkyl. For example, $R^3$ can be methyl or ethyl. In another embodiment, $R^3$ is cycloalkyl. In another embodiment, $R^3$ is aryl. In yet another embodiment, $R^3$ is heteroaryl. In one embodiment, $R^5$ or $R^6$ is independently hydrogen, alkyl, cycloalkyl, aryl, heteroaryl, amino, or $R^5$ taken together with $R^6$ forms a saturated or partially unsaturated 3-9 membered ring. For example, $R^5$ and $R^6$ can be hydrogen. In one embodiment, $R^7$ is independently hydrogen or halo. In one embodiment, $R^8$ is independently hydrogen, halo, cyano, alkyl, cycloalkyl, aryl, heteroaryl, or amino. In one embodiment, $R^8$ is hydrogen.

In some embodiments, the present invention is drawn to compounds having Formula (VI) or pharmaceutically acceptable salts thereof:

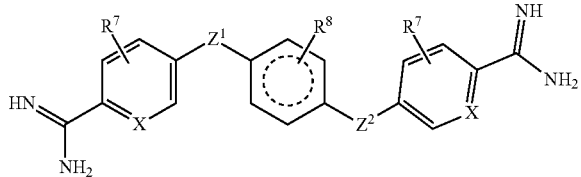

Formula (VI)

wherein $Z^1$, $Z^2$, $Y^1$-$Y^{10}$, $R^1$, $R^2$, $R^3$, $R^4$, $R^5$, $R^6$, and $R^7$ are defined in formula (A), $R^8$ is independently hydrogen, halo, cyano, alkyl, cycloalkyl, aryl, heteroaryl, or amino.

In some embodiments, at least one X is N. In some embodiments, the amidine substituted two rings are different so that the compound is not symmetrical.

In one embodiment, $Z^1$ or $Z^2$ is independently selected from the group consisting of O, N, and S, optionally substituted. In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring. In another embodiment, $Z^1$ and $Z^2$ are $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring.

In one embodiment, $R^3$ is hydrogen. In another embodiment, $R^3$ is alkyl, e.g., $R^3$ can be methyl or ethyl. In another embodiment, $R^3$ is cycloalkyl. In another embodiment, $R^3$ is aryl. In yet another embodiment, $R^3$ is heteroaryl. In one embodiment, $R^5$ or $R^6$ is independently hydrogen, alkyl, cycloalkyl, aryl, heteroaryl, amino, or $R^5$ taken together with $R^6$ forms a saturated or partially unsaturated 3-9 membered ring. For example, $R^5$ and $R^6$ can be hydrogen. In one embodiment, $R^7$ is independently hydrogen or halo. In one embodiment, $R^8$ is independently hydrogen, halo, cyano, alkyl, cycloalkyl, aryl, heteroaryl, or amino. In one embodiment, $R^8$ is hydrogen.

In some embodiments, the present invention is drawn to compounds having Formula (VII) or pharmaceutically acceptable salts thereof:

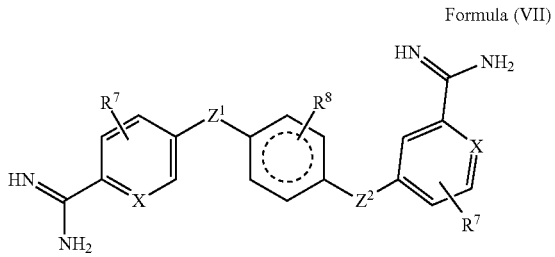

Formula (VII)

wherein $Z^1$, $Z^2$, $Y^1$-$Y^{10}$, $R^1$, $R^2$, $R^3$, $R^4$, $R^5$, $R^6$, and $R^7$ are defined in formula (A), $R^8$ is independently hydrogen, halo, cyano, alkyl, cycloalkyl, aryl, heteroaryl, or amino.

In some embodiments, at least one X is N. In some embodiments, the amidine substituted two rings are different so that the compound is not symmetrical.

In one embodiment, $Z^1$ or $Z^2$ is independently selected from the group consisting of O, N, and S, optionally substituted. In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring. In one embodiment, $R^3$ is hydrogen. In another embodiment, $R^3$ is alkyl, e.g., $R^3$ can be methyl or ethyl. In another embodiment, $R^3$ is cycloalkyl. In another embodiment, $R^3$ is aryl. In yet another embodiment, $R^3$ is heteroaryl. In one embodiment, $R^5$ or $R^6$ is independently hydrogen, alkyl, cycloalkyl, aryl, heteroaryl, amino, or $R^5$ taken together with $R^6$ forms a saturated or partially unsaturated 3-9 membered ring. For example, $R^5$ and $R^6$ can be hydrogen. In one embodiment, $R^7$ is independently hydrogen or halo. In one embodiment, $R^8$ is independently hydrogen, halo, cyano, alkyl, cycloalkyl, aryl, heteroaryl, or amino. In one embodiment, $R^8$ is hydrogen.

In some embodiments, the present invention is drawn to compounds having Formula (VIII) or pharmaceutically acceptable salts thereof:

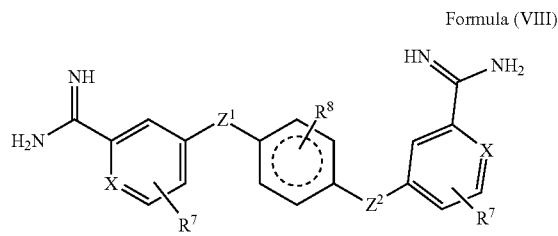

Formula (VIII)

wherein $Z^1$, $Z^2$, $Y^1$-$Y^{10}$, $R^1$, $R^2$, $R^3$, $R^4$, $R^5$, $R^6$, and $R^7$ are defined in formula (A), $R^8$ is independently hydrogen, halo, cyano, alkyl, cycloalkyl, aryl, heteroaryl, or amino.

In some embodiments, at least one X is N. In some embodiments, the amidine substituted two rings are different so that the compound is not symmetrical.

In one embodiment, $Z^1$ or $Z^2$ is independently selected from the group consisting of O, N, and S, optionally substituted. In one embodiment, $Z^1$ or $Z^2$ is independently O, optionally substituted. In another embodiment, $Z^1$ or $Z^2$ is independently S, optionally substituted. In yet another embodiment, $Z^1$ or $Z^2$ is independently $NR^3$, wherein $R^3$ is hydrogen. In one embodiment, $Z^1$ or $Z^2$ is independently $NR^3$, wherein $R^3$ is alkyl, cycloalkyl, aryl, or heteroaryl. In another embodiment, $Z^1$ or $Z^2$ is independently $NR^3$ or $CR^5R^6$. In another embodiment, $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring. In one embodiment, $R^3$ is hydrogen. In another embodiment, $R^3$ is alkyl, e.g., $R^3$ can be methyl or ethyl. In another embodiment, $R^3$ is cycloalkyl. In another embodiment, $R^3$ is aryl. In yet another embodiment, $R^3$ is heteroaryl. In one embodiment, $R^5$ or $R^6$ is independently hydrogen, alkyl, cycloalkyl, aryl, heteroaryl, amino, or $R^5$ taken together with $R^6$ forms a saturated or partially unsaturated 3-9 membered ring. For example, $R^5$ and $R^6$ can be hydrogen. In one embodiment, $R^7$ is independently hydrogen or halo. In one embodiment, $R^8$ is independently hydrogen, halo, cyano, alkyl, cycloalkyl, aryl, heteroaryl, or amino. In one embodiment, $R^8$ is hydrogen.

Exemplary compounds include compounds of the following structures, or a pharmaceutically acceptable salt thereof:

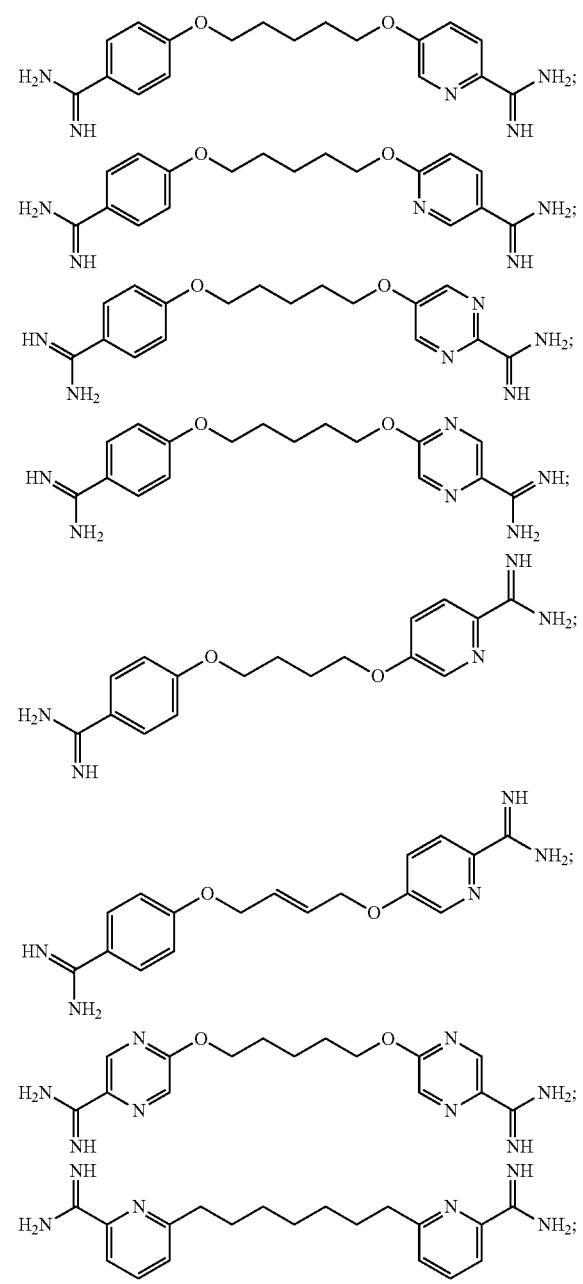

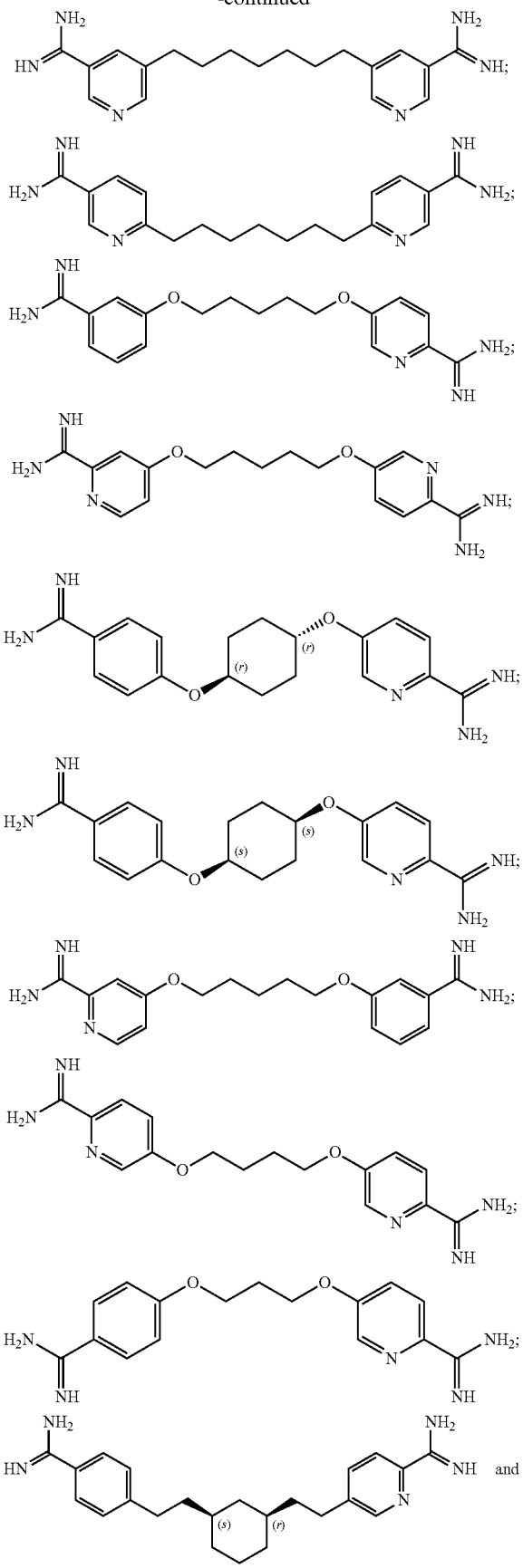

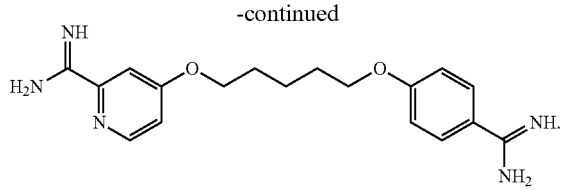

Methods

Compounds and compositions detailed herein, such as a pharmaceutical composition containing a compound of any formula provided herein or a salt thereof and a pharmaceutically acceptable carrier or excipient, may be used in methods of administration and treatment as provided herein. It is understood that any of the methods, or pharmaceutical compositions, detailed herein may employ a compound of any formulae or variation thereof detailed herein, or a pharmaceutically acceptable salt thereof. In one embodiment, any of the methods, or pharmaceutical compositions, detailed herein employ a compound of Formula (A), or a pharmaceutically acceptable salt thereof, such as a method that comprises administering a compound of Formula (A), or a pharmaceutically acceptable salt thereof, to a subject. In one embodiment, any of the methods, or pharmaceutical compositions, detailed herein employ a compound of Formula (I), or a pharmaceutically acceptable salt thereof. In one embodiment, any of the methods, or pharmaceutical compositions, detailed herein employ a compound of Formula (II), or a pharmaceutically acceptable salt thereof. In one embodiment, any of the methods, or pharmaceutical compositions, detailed herein employ a compound of Formula (III), or a pharmaceutically acceptable salt thereof. In one embodiment, any of the methods, or pharmaceutical compositions, detailed herein employ a compound of Formula (IV), or a pharmaceutically acceptable salt thereof. In one embodiment, any of the methods, or pharmaceutical compositions, detailed herein employ a compound of Formula (V), or a pharmaceutically acceptable salt thereof. In one embodiment, any of the methods, or pharmaceutical compositions, detailed herein employ a compound of Formula (VI), or a pharmaceutically acceptable salt thereof. In one embodiment, any of the methods, or pharmaceutical compositions, detailed herein employ a compound of Formula (VII), or a pharmaceutically acceptable salt thereof. In one embodiment, any of the methods, or pharmaceutical compositions, detailed herein employ a compound of Formula (VIII), or a pharmaceutically acceptable salt thereof. In one embodiment, any of the methods, or pharmaceutical compositions, detailed herein employ a compound of Table I, or a pharmaceutically acceptable salt thereof. Thus, it is appreciated that any method or pharmaceutical composition detailed herein in one embodiment comprises a compound of formula

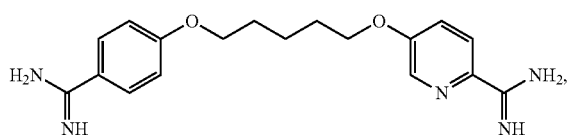 [SMILES: N=C(N)c1ccc(OCCCCCOc2ccc(C(=N)N)nc2)cc1]

or a pharmaceutically acceptable salt thereof, such as a method that comprises administering the compound or a pharmaceutically acceptable salt thereof to a subject. In one embodiment, any method or pharmaceutical composition detailed herein comprises a pharmaceutically acceptable salt of a compound of formula

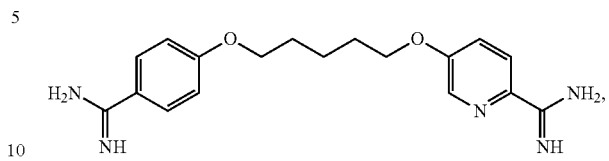

such as a method that comprises administering a pharmaceutically acceptable salt of said compound to a subject.

Provided herein is a method of treating cancer comprising administering the compounds described herein to a subject in need thereof. In some embodiments, the method comprises treating a solid tumor. In some embodiments, the method comprises treating a cancer selected from the group consisting of liver cancer, cholangiocarcinoma, colon cancer, hepatic cholangiocarcinoma, and kidney cancer. In some embodiments, the subject is human.

The compounds and compositions described herein can be administered to a subject in need of treatment for a cell proliferation disorder such as cancer, particularly cancers selected from liver cancer, cholangiocarcinoma, osteosarcoma, melanoma, breast cancer, renal cancer, prostate cancer, gastric cancer, colorectal cancer, thyroid cancer, head and neck cancer, ovarian cancer, pancreatic cancer, neuronal cancer, lung cancer, uterine cancer, leukemia, or lymphoma. The subject is typically a mammal diagnosed as being in need of treatment for one or more of such proliferative disorders, and frequently the subject is a human. The methods comprise administering an effective amount of at least one compound of the invention; optionally the compound may be administered in combination with one or more additional therapeutic agents, particularly the therapeutic agents known to be useful for treating the cancer or proliferative disorder afflicting the particular subject. It would be appreciate by one of ordinary skill in the art that colorectal cancer and colon cancer are used interchangeably and kidney and renal cancer are used interchangeably in this disclosure.

The compounds of the present disclosure or their pharmaceutically acceptable salts are generally administered in a therapeutically effective amount. The term "therapeutically effective amount" may refer to the amount (or dose) of a compound or other therapy that is necessary and sufficient to prevent, reduce, ameliorate, treat or eliminate a condition, or risk thereof, when administered to a subject in need of such compound or other therapy. The amount of the compound actually administered to a subject may be determined by a physician or caregiver, in the light of the relevant circumstances, including the condition to be treated, the chosen route of administration, the compound administered and its relative activity, the age, weight, the response of the individual patient, the severity of the patient's symptoms, and the like. Thus, the therapeutically effective amount may vary, for example, it may vary depending upon the subject's condition, the weight and age of the subject, the severity of the disease condition, the manner of administration and the like.

The compounds of the current disclosure may be administered by any of the accepted modes of administration of agents having similar utilities, for example, by oral, cutaneous, topical, intradermal, intrathecal, intravenous, subcutaneous, intramuscular, intra-articular, intraspinal or spinal, nasal, epidural, rectal, vaginal or transdermal/transmucosal routes. A suitable route will depend on the nature and severity of the condition being treated. Oral administration may be a primary route of administration for compounds of the present disclosure as they generally exhibit increased oral bioavailability as well as enhanced organ targeting in combination of reduced in vivo toxicity. However, intravenous (IV) administration may be a route of administration for compounds of this disclosure. Intramuscular (IM) administration may be a route of administration for compounds of this disclosure. Subcutaneous, Sublingual, or percutaneous administration can be also contemplated as a route of administration for the compounds of the present disclosure. Sublingual administration may be implemented with an appropriate formulation for the compounds. Inhalation administration can be also employed for a route of administration with an appropriate formulation for the compounds and type of cancer that can be benefited by this route (e.g., lung cancer).

In a particular example, the pharmaceutical composition provided herein may be administered to a human patient orally at a dose about 0.1 mg per kg to about 300 mg per kg or to even 500 mg per kg. In another embodiment, the pharmaceutical composition provided herein may be administered to a human patient orally at a dose about 1 mg per kg to about 300 mg per kg daily. In another particular example, the pharmaceutical composition provided herein may be administered to a human patient orally a t a dose about 1 mg per kg to about 100 m per kg.

A subject may suffer from cancer. The subject can be a mammal. The subject can be a human patient suffering from cancer. Examples of cancer include, but are not limited to, adrenal cancer, anal cancer, bile duct cancer, bladder cancer, cancer of the blood, bone cancer, a brain tumor, breast cancer, cancer of the cardiovascular system, cervical cancer, colon cancer, cancer of the digestive system, cancer of the endocrine system, endometrial cancer, esophageal cancer, eye cancer, gallbladder cancer, a gastrointestinal tumor, kidney cancer, laryngeal cancer, leukemia, liver cancer, lung cancer, cholangiocarcinoma, lymphoma, mesothelioma, cancer of the muscular system, myelodysplastic syndrome, myeloma, nasal cavity cancer, nasopharyngeal cancer, cancer of the nervous system, cancer of the lymphatic system, oral cancer, oropharyngeal cancer, ovarian cancer, pancreatic cancer, penile cancer, pituitary tumors, prostate cancer, cancer of the reproductive system, cancer of the respiratory system, a sarcoma, salivary gland cancer, skeletal system cancer, skin cancer, small intestine cancer, stomach cancer, testicular cancer, thymus cancer, thyroid cancer, bladder cancer, or vaginal cancer. In one embodiment, the subject suffers from liver cancer. In another embodiment, the subject suffers from cholangiocarcinoma. In another embodiment, the subject suffers from hepatic cholangiocarcinoma. In yet another embodiment, the subject suffers from kidney cancer. In yet another embodiment, the subject suffers from colon cancer. In yet another embodiment, the subject suffers from lung cancer (e.g., small cell lung cancer or non-small cell lung cancer). In yet another embodiment, the subject suffers from breast cancer. In yet another embodiment, the subject suffers from ovarian cancer.

Examples of cancer include cancers that cause solid tumors as well as cancers that do not cause solid tumors. Furthermore, any of the cancers mentioned herein may be a primary cancer (e.g., a cancer that is named after the part of the body where it first started to grow) or a secondary or metastatic cancer (e.g., a cancer that has originated from another part of the body).

In some embodiments, provided herein in a method of inhibiting cancer cell proliferation in an individual comprising administering a compound provided herein to the individual. In some embodiments, at least about 10% (including for example at least about any of about 20%, about 30%, about 40%, about 60%, about 70%, about 80%, about 90%, or about 100%) of cell proliferation is inhibited. In some embodiments, th In some embodiments, proliferation of a solid tumor is inhibited. In some embodiments, the proliferation of liver cancer cells is inhibited. In some embodiments, proliferation of colon cancer cells is inhibited. In some embodiments, proliferation of kidney cancer cells is inhibited. In some embodiments, proliferation of cholangiocarcinoma cells is inhibited.

Also provided herein is a method of inhibiting tumor metastasis in an individual comprising administering a compound provided herein to the individual. In some embodiments, at least about 10% (including for example at least about any of about 20%, about 30%, about 40%, about 60%, about 70%, about 80%, about 90%, or about 100%) of metastasis is inhibited. In some embodiments, metastasis of liver cancer is inhibited. In some embodiments, metastasis of colon cancer is inhibited. In some embodiments, metastasis of kidney cancer is inhibited. In some embodiments, metastasis of cholangiocarcinoma is inhibited. In any of the above embodiments, metastasis to the lymph nodes, lung, bone, or brain is inhibited. In any of the above embodiments, tumor metastasis may be inhibited for at least 1, 2, 3, 4, 5, 6, 7, 8, 9, 10, 11, or 12 weeks following treatment.

In some embodiments, the method comprises reducing tumor size and/or tumor burden in an individual. In some embodiments, the tumor size is reduced at least about 10% (including for example at least about any of about 20%, about 30%, about 40%, about 60%, about 70%, about 80%, about 90%, or about 100%). In some embodiments, the tumor is liver cancer. In some embodiments, the tumor is kidney cancer. In some embodiments, the tumor is colon cancer. In some embodiments, the tumor is a cholangiocarcinoma.

In some embodiments, the method comprises prolonging progression free survival in an individual. In some embodiments, the method prolongs the time to disease progression by at least any of 1, 2, 3, 4, 5, 6, 7, 8, 9, 10, 11, or 12 weeks. In some embodiments, the individual has a solid tumor. In some embodiments, the individual has liver cancer. In some embodiments, the individual has kidney cancer. In some embodiments, the individual has colon cancer. In some embodiments, the individual has a cholangiocarcinoma.

In some embodiments, the method comprises alleviating one or more symptoms in an individual having cancer. In some embodiments, the individual has a solid tumor. In some embodiments, the individual has liver cancer. In some embodiments, the individual has kidney cancer. In some embodiments, the individual has colon cancer. In some embodiments, the individual has a cholangiocarcinoma.

In some embodiments, the method comprises improving the quality of life in an individual having cancer. In some embodiments, the individual has a solid tumor. In some embodiments, the individual has liver cancer. In some embodiments, the individual has kidney cancer. In some embodiments, the individual has colon cancer. In some embodiments, the individual has a cholangiocarcinoma.

In some embodiments, the method results in an objective response (such as a partial response or a complete response) in a patient having cancer. In some embodiments, the individual has a solid tumor. In some embodiments, the individual has liver cancer. In some embodiments, the individual has kidney cancer. In some embodiments, the individual has colon cancer. In some embodiments, the individual has a cholangiocarcinoma.

In some embodiments, compounds of the present invention are not metabolized by cytochrome P-450, resulting in reduced toxicity, in particular hepatotoxicity, compared to existing treatments. Accordingly, in some embodiments, provided herein is a method of treating cancer in an individual, wherein the individual has reduced liver function. In some embodiments, the individual has a Child-Pugh score of Class B or Class C.

In some embodiments, the present methods result in a decrease in one or more markers of liver damage or tumor burden in an individual having liver cancer. In some embodiments, the method results in the level of one or more of alanine amino transferase (ALT), aspartate amino transferase (AST), or alkaline phosphate (ALP) being reduced. In some embodiments, the level of a marker of liver damage is reduced by at least about 5% (such as by about 10%, about, about 15%, about 20%, about 25%, about 30%, about 40%, about 50% about 60%, about 70%, about 80%, or about 90%).

Compounds of the present disclosure or a pharmaceutically acceptable salt thereof can be administered to a subject (e.g., human patient) suffering from cancer, e.g., orally, intravenously or subcutaneously, at a dose of, for example, about 0.5 mg per kg, 0.6 mg per kg, about 0.7 mg per kg, about 0.8 mg per kg, about 0.9 mg per kg, about 1 mg per kg, about 2 mg per kg, about 3 mg per kg, about 4 mg per kg, about 5 mg per kg, about 6 mg per kg, about 7 mg per kg, about 8 mg per kg, about 9 mg per kg, about 10 mg per kg, about 15 mg per kg, about 20 mg per kg, about 30 mg per kg about 30 mg per kg, about 40 mg per kg, about 50 mg per kg, about 60 mg per kg, about 70 mg per kg, about 80 mg per kg, about 90 mg per kg, about 100 mg per kg, about 110 mg per kg, about 120 mg per kg, about 130 mg per kg, about 140 mg per kg, about 150 mg per kg, about 160 mg per kg, about 170 mg per kg, about 180 mg per kg, about 190 mg per kg, about 200 mg per kg, about 210 mg per kg, about 220 mg per kg, about 230 mg per kg, about 240 mg per kg, about 250 mg per kg, about 260 mg per kg, about 270 mg per kg, about 280 mg per kg, about 290 mg per kg, about 300 mg per kg, about 350 mg per kg, about 400 mg per kg, about 450 mg per kg, about 500 mg per kg, or about 600 mg per kg.

In one embodiment, compounds of the present disclosure or a pharmaceutically acceptable salt thereof can be administered orally at a dose of, for example, about 0.5 mg per kg, 0.6 mg per kg, about 0.7 mg per kg, about 0.8 mg per kg, about 0.9 mg per kg, about 1 mg per kg, about 2 mg per kg, about 3 mg per kg, about 4 mg per kg, about 5 mg per kg, about 6 mg per kg, about 7 mg per kg, about 8 mg per kg, about 9 mg per kg, about 10 mg per kg, about 15 mg per kg, about 20 mg per kg, about 30 mg per kg, about 40 mg per kg, about 50 mg per kg, about 60 mg per kg, about 70 mg per kg, about 80 mg per kg, about 90 mg per kg, about 100 mg per kg, about 110 mg per kg, about 120 mg per kg, about 130 mg per kg, about 140 mg per kg, about 150 mg per kg, about 160 mg per kg, about 170 mg per kg, about 180 mg per kg, about 190 mg per kg, about 200 mg per kg, about 210 mg per kg, about 220 mg per kg, about 230 mg per kg, about 240 mg per kg, about 250 mg per kg, about 260 mg per kg, about 270 mg per kg, about 280 mg per kg, about 290 mg per kg, about 300 mg per kg, about 350 mg per kg, about 400 mg per kg, about 450 mg per kg, about 500 mg per kg, or about 600 mg per kg.

In one embodiment, compounds of the present disclosure or a pharmaceutically acceptable salt thereof can be administered intravenously at a dose of, for example, 0.5 mg per kg, 0.6 mg per kg, about 0.7 mg per kg, about 0.8 mg per kg, about 0.9 mg per kg, about 1 mg per kg, about 2 mg per kg, about 3 mg per kg, about 4 mg per kg, about 5 mg per kg, about 6 mg per kg, about 7 mg per kg, about 8 mg per kg, about 9 mg per kg, about 10 mg per kg, about 15 mg per kg, about 20 mg per kg, about 25 mg per kg, about 30 mg per kg, about 35 mg per kg, about 40 mg per kg, about 50 mg per kg, about 60 mg per kg, about 70 mg per kg, about 80 mg per kg, about 90 mg per kg, about 100 mg per kg, about 110 mg per kg, about 120 mg per kg, about 130 mg per kg, about 140 mg per kg, about 150 mg per kg, about 160 mg per kg, about 170 mg per kg, about 180 mg per kg, about 190 mg per kg, about 200 mg per kg, about 210 mg per kg, about 220 mg per kg, about 230 mg per kg, about 240 mg per kg, about 250 mg per kg, about 260 mg per kg, about 270 mg per kg, about 280 mg per kg, about 290 mg per kg, or about 300 mg per kg.

In one embodiment, compounds of the present disclosure or a pharmaceutically acceptable salt thereof can be administered subcutaneously at a dose of, for example, 0.5 mg per kg, 0.6 mg per kg, about 0.7 mg per kg, about 0.8 mg per kg, about 0.9 mg per kg, about 1 mg per kg, about 2 mg per kg, about 3 mg per kg, about 4 mg per kg, about 5 mg per kg, 6 mg per kg, about 7 mg per kg, about 8 mg per kg, about 9 mg per kg, about 10 mg per kg, about 15 mg per kg, about 20 mg per kg, about 30 mg per kg, about 40 mg per kg, about 50 mg per kg, about 60 mg per kg, about 70 mg per kg, about 80 mg per kg, about 90 mg per kg, about 100 mg per kg, about 110 mg per kg, about 120 mg per kg, about 130 mg per kg, about 140 mg per kg, about 150 mg per kg, about 160 mg per kg, about 170 mg per kg, about 180 mg per kg, about 190 mg per kg, about 200 mg per kg, about 210 mg per kg, about 220 mg per kg, about 230 mg per kg, about 240 mg per kg, about 250 mg per kg, about 260 mg per kg, about 270 mg per kg, or about 280 mg per kg, about 290 mg per kg, or about 300 mg per kg.

In one embodiment, compounds of the present disclosure or a pharmaceutically acceptable salt thereof can be administered orally to a subject suffering from liver cancer at a dose of, for example, about 0.5 mg per kg, 0.6 mg per kg, about 0.7 mg per kg, about 0.8 mg per kg, about 0.9 mg per kg, about 1 mg per kg, about 2 mg per kg, about 3 mg per kg, about 4 mg per kg, about 5 mg per kg, about 6 mg per kg, about 7 mg per kg, about 8 mg per kg, about 9 mg per kg, about 10 mg per kg, about 15 mg per kg, about 20 mg per kg, about 30 mg per kg, about 40 mg per kg, about 50 mg per kg, about 60 mg per kg, about 70 mg per kg, about 80 mg per kg, about 90 mg per kg, about 100 mg per kg, about 110 mg per kg, about 120 mg per kg, about 130 mg per kg, about 140 mg per kg, about 150 mg per kg, about 160 mg per kg, about 170 mg per kg, about 180 mg per kg, about 190 mg per kg, about 200 mg per kg.

The administration can be three times a day, twice a day, once a day, once in two days, once in three days, once in four days, once in five days, once in six days, once in a week, once in ten days, or once in two weeks. The administration can also include dosing holiday(s) from about 1 day to about 7 days between administration.

Combination Therapy

The disclosure provided herein describes methods to treat cancer in a subject by administering to a subject at least one compound of the present disclosure. The methods disclosed herein can further comprise administering to the subject a combination of a compound of Formulae (I)-(VIII) or a pharmaceutically acceptable salt thereof and at least one additional anticancer agent wherein the combined composition may be administered as a co-formulation or separately.

In certain particular embodiments, more than one compound of the current disclosure may be administered at a time to the subject. In some embodiments, two compounds of the current disclosure in combination may act synergistically or additively, and either compound may be used in a lesser amount than if administered alone.

In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent. In other embodiments, compounds disclosed herein and/or pharmaceutical compositions thereof are administered prior or subsequent to administration of other therapeutic agents.

In combination therapy, the additional therapeutic agent(s) used in combination therapy can be an anticancer agent such as etoposide, cisplatin, oxaliplatin, gemcitabine, irinotecan, anthracycline, and taxol.

As used herein, the term "therapeutically effective amount" means an amount of pentamidine analog as in Formulae (I)-(VIII), or a pharmaceutically acceptable salt thereof. The dose of a compound to be administered according to this invention will be determined in light of the particular circumstances surrounding the case including, for example, the compound administered, the route of administration, condition of the patient, the stage of cancer and physical property of an anti-cancer drug used in combinatory therapy.

For administration to a subject, a pentamidine analog, or a pharmaceutically acceptable salt thereof, is typically formulated into a pharmaceutical composition and a pharmaceutically acceptable carrier. Therapeutic compositions typically are sterile and adequately stable under the conditions of manufacture and storage.

There are numerous types of anti-cancer approaches that can be used in conjunction with a pentamidine analogue, or a pharmaceutically acceptable salt thereof, for example, treatment with chemotherapeutic agents, biological agents, radiation, and surgery. The methods of the invention can employ these approaches to treat the same types of cancers as those for which they are used in the art. Also, these approaches can be carried out according to parameters (e.g., regimens and doses) that are similar to those that are known in the art for their use.

Chemotherapeutic drugs of several different types including, for example, antimetabolites, antibiotics, alkylating agents, plant alkaloids, hormonal agents, anticoagulants, antithrombotics, and other natural products, among others, can be used in conjunction with pentamidine analogues disclosed herein.

Numerous approaches for administering anticancer drugs are known in the art, and can readily be adapted for use in the present invention. A preferred route of administration is oral administration for combination therapy. For systemic administration, the drugs can be administered by, for example, intravenous injection or infusion (continuous or bolus). Appropriate scheduling and dosing of such administration can readily be determined by those of skill in this art based on, for example, preclinical studies in animals and clinical studies (e.g., phase I studies) in humans. Many regimens used to administer chemotherapeutic drugs involve, for example, intravenous administration of a drug (or drugs) followed by repetition of this treatment after a period (e.g., 1-4 weeks) during which the patient recovers from any adverse side effects of the treatment. It may be desirable to use both drugs at each administration or, alternatively, to have some (or all) of the treatments include only one drug.

Pharmaceutical Formulation

The compounds of the current disclosure may be administered by any of the accepted modes of administration of agents having similar utilities, for example, by oral, cutaneous, topical, intradermal, intrathecal, intravenous, subcutaneous, intramuscular, intra-articular, intraspinal or spinal, nasal, epidural, or transdermal/transmucosal inhalable routes.

In one particular example, the pharmaceutical composition can be administered to a patient orally. In another particular example, the pharmaceutical composition comprising pentamidine or a pharmaceutically acceptable salt thereof may be administered to a patient intravenously (e.g., injection or infusion). In another particular example, the pharmaceutical composition may be administered to a patient intramuscularly. In a particular example, the pharmaceutical composition may be administered to a patient nasally. A pharmaceutical composition (e.g., for oral administration or for inhalation, injection, infusion, subcutaneous delivery, intramuscular delivery, intraperitoneal delivery, sublingual delivery, or other methods) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. A liquid pharmaceutical composition may be delivered orally.

A pharmaceutical composition comprising a compound of Formulae (I)-(VIII) or a pharmaceutically acceptable salt thereof may be formulated for sustained or slow release (also called timed release or controlled release). Such compositions can be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may be biodegradable; preferably the formulation provides a relatively constant level of active component release. Non-limiting examples of excipients include water, alcohol, glycerol, chitosan, alginate, chondroitin, Vitamin E, mineral oil, and dimethyl sulfoxide (DMSO). The amount of compound contained within a sustained release formulation depends upon the site of implantation, the rate and expected duration of release, and the nature of the condition, disease or disorder to be treated or prevented.

The pharmaceutical composition comprising one or more pentamidine analogs or a pharmaceutically acceptable salt thereof may be effective over time. In some cases, the pharmaceutical composition may be effective for one or more days. In some cases, the duration of efficacy of the pharmaceutical composition is over a long period of time. In some cases, the efficacy of the pharmaceutical composition may be greater than 2 days, 3 days, 4 days, 5 days, 6 days, 1 week, 2 weeks, 3 weeks, or 1 month.

In making the pharmaceutical composition comprising one or more pentamidine analogs or a pharmaceutically acceptable salt thereof, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The compositions of the disclosure can be formulated so as to provide quick, sustained or delayed release of the active ingredient after administration to the patient by employing procedures known in the art. In some cases, the pharmaceutical composition comprising pentamidine or a pharmaceutically acceptable salt thereof may comprise an excipient that can provide long term preservation, bulk up a formulation that contains a potent active ingredient, facilitate drug absorption, reduce viscosity, add flavoring, or enhance the solubility of the pharmaceutical composition.

In some cases, the pharmaceutical composition comprising a pentamidine analog or a pharmaceutically acceptable salt thereof may comprise a pharmaceutically acceptable carrier. The pharmaceutically acceptable carrier may include any and all solvents, dispersion media, coatings, antibacterial and antifungal agents, isotonic and absorption delaying agents, and the like that are physiologically compatible. Preferably, the carrier is suitable for oral administration. The active compound may be coated in a material to protect the compound from the action of acids and other natural conditions that may inactivate the compound. The carrier can be suitable for parenteral (e.g., intravenous, intramuscular, subcutaneous, intrathecal) administration (e.g., by injection or infusion).

The present invention also contemplates formulating a pharmaceutically acceptable salt of a compound of Formulae (I)-(VIII). In general, pharmaceutical salts may include, but are not included, salts and base addition salts (e.g., hydrochloric acid salt, dihydrochloric acid salt, sulfuric acid salt, citrate, hydrobromic acid salt, hydroiodic acid salt, nitric acid salt, bisulfate, phosphoric acid salt, super phosphoric acid salt, isonicotinic acid salt, acetic acid salt, lactic acid salt, salicylic acid salt, tartaric acid salt, pantothenic acid salt, ascorbic acid salt, succinic acid salt, maleic acid salt, fumaric acid salt, gluconic acid salt, saccharinic acid salt, formic acid salt, benzoic acid salt, glutaminic acid salt, methanesulfonic acid salt, ethanesulfonic acid salt, benzenesulfonic acid salt, p-toluenesulfonic acid salt, pamoic acid salt (pamoate)), as well as salts of aluminum, calcium, lithium, magnesium, calcium, sodium, zinc, and diethanolamine.

The present invention is further illustrated by the following examples which should not be construed as further limiting. The contents of all references, patents and published patent applications cited throughout this application, as well as the Figures and the Appendix of sequences provided herein, are expressly incorporated herein by reference in their entirety.

EXAMPLES

Analogs of pentamidine were designed and synthesized (see Table 1) using the synthesis methods described further below.

Formula (I)

General Information $^1$H NMR spectra and $^{13}$C NMR spectra were recorded on a Varian 400 MHz or Bruker Avance III 500 MHz spectrometers. Spectra are referenced to residual chloroform (δ 7.26, $^1$H), DMSO (δ 2.54, $^1$H) or methanol (δ 3.34, $^1$H) unless otherwise noted. Chemical shifts are reported in ppm (δ); multiplicities are indicated by s (singlet), d (doublet), t (triplet), q (quartet), quint (quintet), sext (sextet), m (multiplet) and br (broad). Coupling constants, J, are reported in Hertz. Silica gel chromatography was performed using a Teledyne Isco CombiFlash® Rf+ instrument using Hi-Purit Silica Flash Cartridges (National Chromatography Inco) or RediSep Rf Gold C18 Cartridges (Teledyne Isco). Analytical HPLC was performed on a Waters ACQUITY UPLC with a photodiode array detector using and a Waters ACQUITY BEH Shield RPC18 (2.1×50 mm, 1.7 μm) column. Analytical LCMS was performed on a Waters ACQUITY UPLC with a Waters 3100 mass detector. Chiral HPLC was performed on a Waters Alliance e2695 with a photodiode array detector using Daicel Chiralpak® AD-H, Chiralpak® IA, Chiralpak IB, Chiralpak® IC, Chiralcel® OD-H or Chiralcel® OJ-H columns. Optical rotations were obtained on a Jasco P-2000 digital polarimeter and are reported as $[\square]_D^T$ temperature (T), concentration (c=g/100 mL) and solvent. Commercially available reagents and solvents were used as received unless otherwise indicated.

TABLE 1

Heteroaryl Pentamidine Analogues

| Cmpd No. | Structure | Name | Human Microsomal CL Rate (uL/min/mg) |
|---|---|---|---|
| 1 | 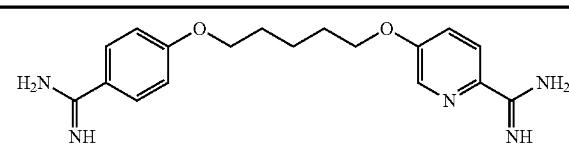 | 5-(5-(4-carbamimidoylphenoxy)pentyloxy)picolinimidamide | 13.6 |

TABLE 1-continued

Heteroaryl Pentamidine Analogues

| Cmpd No. | Structure | Name | Human Microsomal CL Rate (uL/min/mg) |
|---|---|---|---|
| 2 | 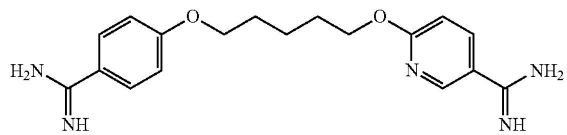 [SMILES: N=C(N)c1ccc(OCCCCCOc2ccc(C(=N)N)cn2)cc1] | 6-((5-(4-carbamimidoylphenoxy)pentyl)oxy)nicotinimidamide | 9.8 |
| 3 | 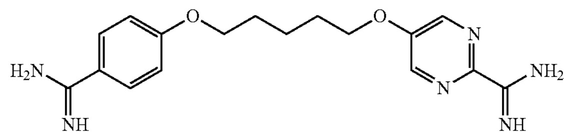 [SMILES: N=C(N)c1ccc(OCCCCCOc2cnc(C(=N)N)nc2)cc1] | 5-((5-(4-carbamimidoylphenoxy)pentyl)oxy)pyrimidine-2-carboximidamide | N/A |
| 4 | 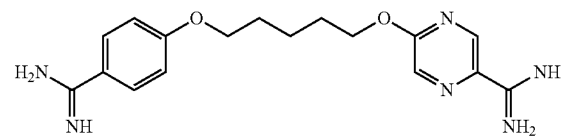 [SMILES: N=C(N)c1ccc(OCCCCCOc2cnc(C(=N)N)cn2)cc1] | 5-((5-(4-carbamimidoylphenoxy)pentyl)oxy)pyrazine-2-carboximidamide | N/A |
| 5 | 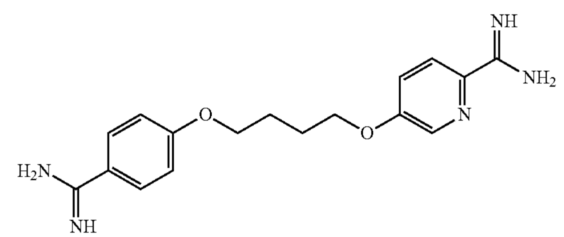 [SMILES: N=C(N)c1ccc(OCCCCOc2ccc(C(=N)N)nc2)cc1] | 5-(4-(4-carbamimidoylphenoxy)butoxy)picolinimidamide | 3.9 |
| 6 | 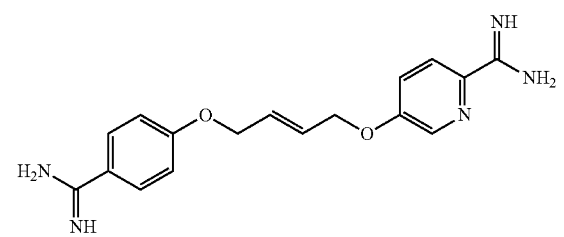 [SMILES: N=C(N)c1ccc(OC/C=C/COc2ccc(C(=N)N)nc2)cc1] | 5-(4-(4-carbamimidoylphenoxy)butoxy)picolinimidamide | 8.1 |
| 7 | 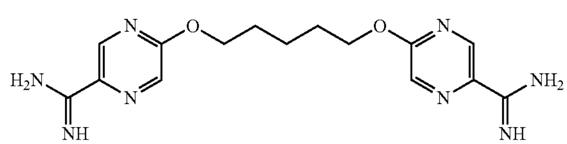 [SMILES: N=C(N)c1cnc(OCCCCCOc2cnc(C(=N)N)cn2)cn1] | 5,5'-(pentane-1,5-diylbis(oxy))bis(pyrazine-2-carboximidamide) | N/A |
| 8 | 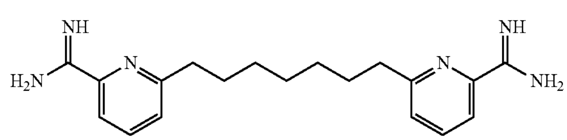 [SMILES: N=C(N)c1cccc(CCCCCCCc2cccc(C(=N)N)n2)n1] | 6,6'-(heptane-1,7-diyl)dipicolinimidamide | 11 |
| 9 | 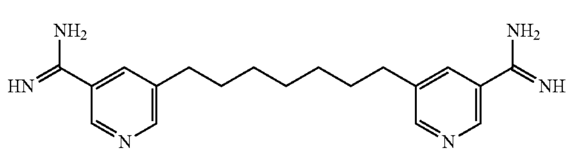 [SMILES: N=C(N)c1cncc(CCCCCCCc2cncc(C(=N)N)c2)c1] | 5,5'-(heptane-1,7-diyl)dinicotinimidamide | 13 |
| 10 | 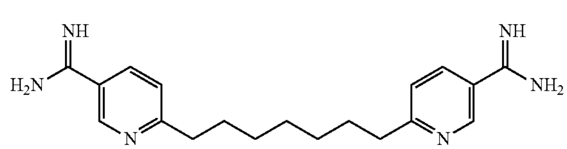 [SMILES: N=C(N)c1ccc(CCCCCCCc2ccc(C(=N)N)cn2)nc1] | 6,6'-(heptane-1,7-diyl)dinicotinimidamide | N/A |

TABLE 1-continued

Heteroaryl Pentamidine Analogues

| Cmpd No. | Structure | Name | Human Microsomal CL Rate (uL/min/mg) |
|---|---|---|---|
| 11 | 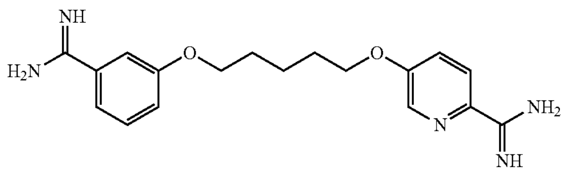 [SMILES: N=C(N)c1cccc(OCCCCCOc2ccc(C(=N)N)nc2)c1] | 5-(5-(3-carbamimidoylphenoxy)pentyloxy)picolinimidamide | 5.2 |
| 12 | 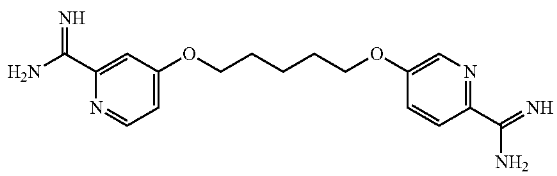 [SMILES: N=C(N)c1ccc(OCCCCCOc2ccnc(C(=N)N)c2)cn1] | 4-((5-((6-carbamimidoylpyridin-3-yl)oxy)pentyl)oxy)picolinimidamide | 7.5 |
| 13 | 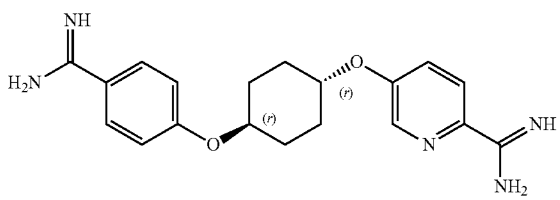 [SMILES: N=C(N)c1ccc(O[C@H]2CC[C@H](Oc3ccc(C(=N)N)nc3)CC2)cc1] | 5-(((1r,4r)-4-(4-carbamimidoylphenoxy)cyclohexyl)oxy)picolinimidamide | 11 |
| 14 | 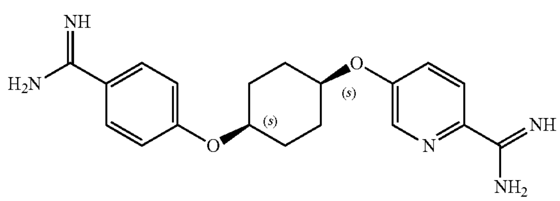 [SMILES: N=C(N)c1ccc(O[C@H]2CC[C@@H](Oc3ccc(C(=N)N)nc3)CC2)cc1] | 5-(((1s,4s)-4-(4-carbamimidoylphenoxy)cyclohexyl)oxy)picolinimidamide | 15.3 |
| 15 | 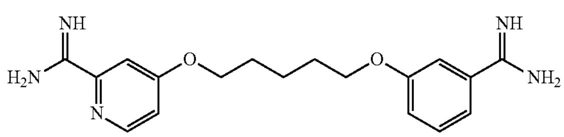 [SMILES: N=C(N)c1cccc(OCCCCCOc2ccnc(C(=N)N)c2)c1] | 4-(5-(3-carbamimidoylphenoxy)pentyloxy)picolinimidamide | 3.2 |
| 16 | 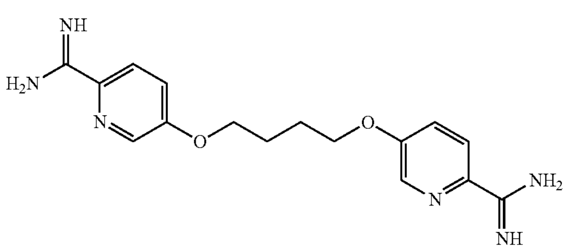 [SMILES: N=C(N)c1ccc(OCCCCOc2ccc(C(=N)N)nc2)cn1] | 5,5'-(butane-1,4-diylbis(oxy))dipicolinimidamide | 4.6 |
| 17 | 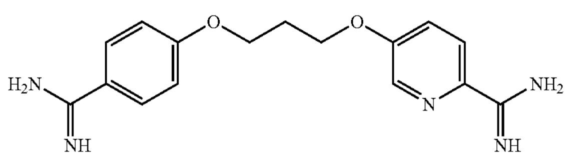 [SMILES: N=C(N)c1ccc(OCCCOc2ccc(C(=N)N)nc2)cc1] | 5-(3-(4-carbamimidoylphenoxy)propoxy)picolinimidamide | 8.1 |
| 18 | 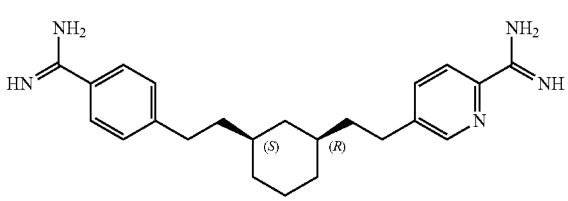 | 5-{2-[(1R,3S)-3-[2-(4-carbamimidoylphenyl)ethyl]cyclohexyl]ethyl}pyridine-2-carboximidamide | 9.5 |

TABLE 1-continued

Heteroaryl Pentamidine Analogues

| Cmpd No. | Structure | Name | Human Microsomal CL Rate (uL/min/mg) |
|---|---|---|---|
| 19 | ![structure] | 4-{[5-(4-carbamimidoylphenoxy)pentyl]oxy}pyridine-2-carboximidamide | 27.7 |

Example 1

Preparation of 5-(5-(4-carbamimidoylphenoxy)pentyloxy)picolinimidamide

Compound 1

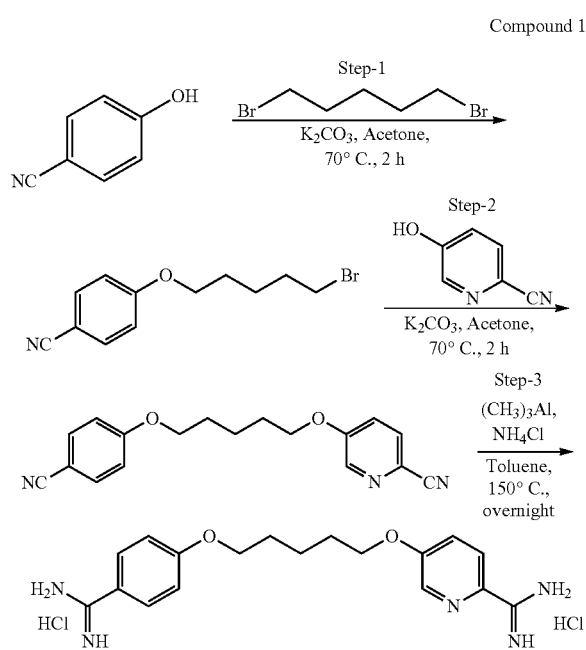

Step 1

To a stirred solution of 4-hydroxybenzonitrile (10 g, 0.08 mol, 1 eq.) in acetone (120 mL) was added 1,5-dibromopentane (95.72 g, 0.42 mol, 5 eq.) and potassium carbonate (23.21 g, 0.16 mol, 2 eq.) Then reaction mixture was stirred at 70° C. for 2 h. The reaction mixture was monitored by TLC-LC-MS. The reaction mixture was diluted with water (500 mL) and extracted with EtOAC (2×800 mL). The separated organic layer was dried over anhydrous Na$_2$SO$_4$ and concentrated under reduced pressure to get crude product. The crude product was purified by glass column to afford 4-((5-bromopentyl) benzonitrile (15 g, 66.94%).

Analytical Data

LC-MS: 268 ([M+1])$^+$

Step 2

To a stirred solution of 4-((5-bromopentyl)benzonitrile (0.52 g, 4.33 mmol, 1 eq.) in acetone (5 mL) was added compound 5-hydroxypicolinonitrile (1.15 g, 4.33 mmol, 1 eq.) and potassium carbonate (1.19 g, 8.66 mmol, 2 eq.) at 70° C. for 2 h. The reaction mixture was monitored by TLC and LC-MS. The reaction mixture was diluted with water (80 mL) and extracted with EtOAC (400 mL). The separated organic layer were dried over anhydrous Na$_2$SO$_4$ and concentrated under reduced pressure to get crude product. The crude product was purified by combi-flash chromatography to afford 5-((5-(cyanophenoxy) pentyl) oxy)picolinonitrile (0.6 g, 45.11%).

Analytical Data

LCMS: 308 ([M+1])$^+$

Step 3

To a stirred suspension of NH$_4$Cl (0.27 g, 0.65 mmol, 8 eq.) in toluene (5 mL) at 0° C. was added trimethylaluminum (0.27 g, 5.21 mmol, 8 eq.). The reaction mixture was allowed to stir at 0° C. for 10 min followed by stirring at RT for 15 min. To this solution was added 5-((5-(4-cyanophenoxy)pentyl)oxy)picolinonitrile (0.2 g, 0.65 mmol 1 eq.) and reaction mixture was allowed to stir at RT for 15 min. The reaction mixture was then stirred under reflux for 18 h. The reaction mixture was cooled to RT and to it was added methanol (5 mL) under ice cooled condition and reaction mixture was allowed to stir at RT for 30 min. The reaction mixture was diluted with 1N HCl (20 mL) and washed with ethyl acetate (20 mL). Aqueous layer was basified with 1N NaOH solution (15 mL) and extracted with ethanol-ethyl acetate (20%, 3×20 mL). The separated organic layer was dried over anhydrous Na$_2$SO$_4$ and concentrated under vacuum to get crude product which was purified by reversed phase HPLC to afford 5-(5-(4-carbamimidoylphenoxy)pentyloxy)picolinimidamide as free base. The free base material was dissolved in 1.25 N HCl in ethanol (5 mL). Removal of ethanol under reduced pressure gave solid which after lyophilization gave white solid 5-(5-(4-carbamimidoylphenoxy)pentyloxy)picolinimidamide as a dihydrochloride salt (0.18 g, 84.68%

Analytical Data

LCMS: 342 [M+1]$^+$ $^1$H NMR (400 MHz, DMSO-d$_6$) δ 9.35 (s, 2H), 9.18 (s, 2H), 9.10 (s, 2H), 8.80 (s, 2H), 8.48 (s, 1H), 8.30 (d, 1H), 7.80 (d, 2H), 7.74 (d, 1H), 7.18 (d, 2H), 4.18 (t, 2H), 4.22 (t, 2H), 1.83 (m, 4H), 1.61 (m, 2H).

Example 2

Preparation of 6-((5-(4-carbamimidoylphenoxy) pentyl)oxy)nicotinimidamide

Compound 2

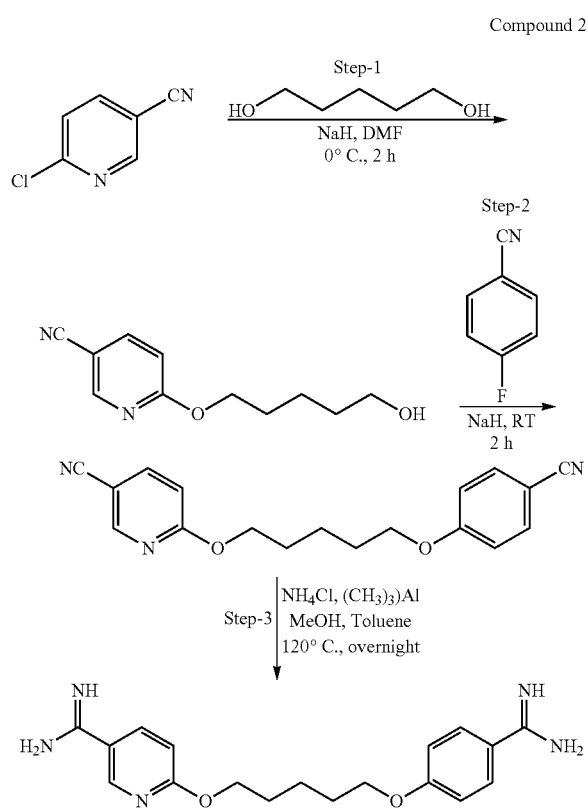

Step 1

To a stirred suspension of NaH (0.28 g, 7.21 mmol, 2.0 eq.) in DMF (6 mL) was added pentane-1,5-diol (0.37 g, 3.62 mmol, 1 eq.) at 0° C. The reaction mixture was allowed to stir at 0° C. for 15 minutes. Then 6-chloronicotinonitrile (0.35 g, 2.52 mmol, 1 eq.) was added to the reaction mixture. The reaction mixture was stirred at 0° C. for 3 h. Progress of reaction was monitored by TLC and LCMS. After the consumption of starting material, the reaction mixture was diluted with water (50 mL) and extracted with ethyl acetate (3×50 mL). The separated organic layer was dried over anhydrous $Na_2SO_4$ and concentrated under reduced pressure to get crude product. The crude product was purified by Combi-Flash chromatography to afford 6-((5-hydroxypentyl) oxy) nicotinonitrile (0.50 g, 67.02%) which was used in the next step.

Analytical Data
LCMS: 207[M+1]$^+$

Step 2

To a stirred solution of 6-((5-hydroxypentyl)oxy)nicotinonitrile (0.15 g, 0.72 mmol, 1.0 eq.) in DMF (5 mL) was added NaH (0.005 g, 1.45 mmol) and the mixture was allowed to stir at 0° C. for 10 minutes. To this mixture was added 4-fluorobenzonitrile (0.10 g, 0.87 mmol, 1.2 eq.) at 0° C. and the reaction mixture was allowed to stir at RT for 2 h. Progress of reaction was monitored by TLC and LCMS. After consumption of starting material, the reaction mixture was diluted with water (50 mL) and extracted with ethyl acetate (2×50 mL). Combined organic layer was dried over anhydrous $Na_2SO_4$ and concentrated under reduced pressure to afford crude product 6-((5-(4-cyanophenoxy)pentyl)oxy) nicotinonitrile (0.18 g, 80.71%) which was used in the next step without further purification.

Analytical Data
LCMS: 308[M+1]$^+$

Step 3

To a stirred suspension of $NH_4Cl$ (0.19 g, 3.66 mmol, 8.0 eq) in toluene (5 mL) at 0° C. was added trimethylaluminum (1.83 mL, 3.66 mmol, 8.0 eq.). The reaction mixture was allowed to stir at 0° C. for 10 minutes followed by stirring at RT for 15 minutes. To this solution was added 6-((5-(4-cyanophenoxy)pentyl)oxy)nicotinonitrile (0.14 g, 0.45 mmol, 1.0 eq.) and reaction mixture was allowed to stir at RT for 15 minutes. The reaction mixture was then stirred under reflux for 18 h. The reaction mixture was cooled to RT and was added methanol (5 mL) under ice cooled condition and reaction mixture was allowed to stir at RT for 30 minutes. The reaction mixture was diluted with 1N HCl (20 mL) and washed with ethyl acetate (20 mL). Aqueous layer was basified with 1N NaOH solution (15 mL) and extracted with ethanol-ethyl acetate (3×20 mL, 20%). The separated organic layer were dried over anhydrous $Na_2SO_4$ and concentrated under vacuum to afford crude (0.11 g) which was purified by reversed phase HPLC to afford 6-((5-(4-carbamimidoylphenoxy) pentyl)oxy) nicotinimidamide as diformate salt. Solid was dissolved in 1.25 M HCl in ethanol (8 mL), solvent was evaporated under reduced pressure to get solid which after lyophilization afforded 6-((5-(4-carbamimidoylphenoxy)pentyl)oxy)nicotinimidamide as dihydrochloride salt (0.02 g, 11.17%).

Analytical Data
LCMS: 342 [M+1]$^+$
$^1$HNMR (400 MHz, DMSO-d6) δ 9.30 (brs, 2H), 9.18 (brs, 2H), 8.95 (brs, 2H), 8.78 (brs, 2H), 8.62 (s, 1H), 8.10 (d, 1H), 7.80 (d, 2H), 7.18 (d, 2H), 7.03 (d, 1H), 4.40 (t, 2H), 4.11 (t, 2H), 1.70-1.90 (m, 4H), 1.50-1.65 (m, 2H).

Example 3

Preparation of 5-((5-(4-carbamimidoylphenoxy) pentyl)oxy)pyrimidine-2-carboximidamide Compound 3

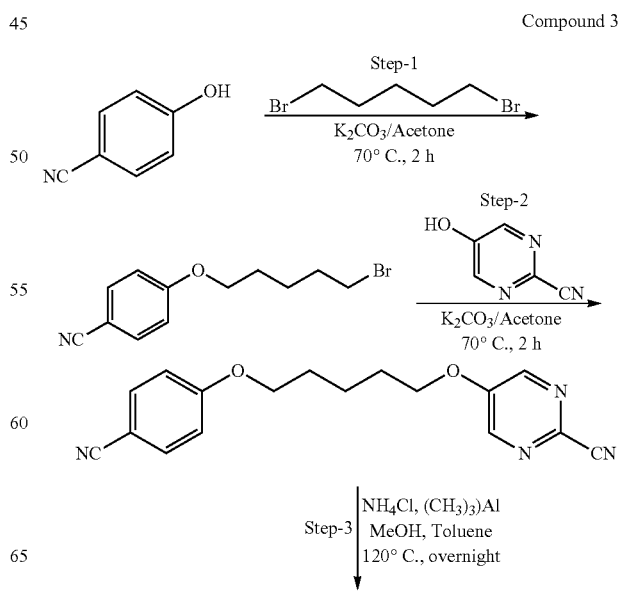

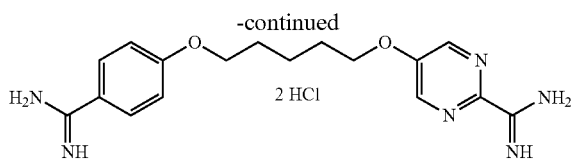

Step 1

To a stirred solution of 4-hydroxybenzonitrile (10 g, 0.08 mol, 1.0 eq.) in acetone (120 mL) was added 1,5-dibromopentane (95.72 g, 0.42 mol, 5.0 eq.) and potassium carbonate (23.21 g, 0.16 mol, 2.0 eq.). The reaction mixture was stirred at 70° C. for 2 h; monitored by TLC and LC-MS. The reaction mixture was diluted with water (2×500 mL) and extracted with EtOAC (2×800 mL). The separated organic layer was dried over anhydrous $Na_2SO_4$ and concentrated under reduced pressure to obtain crude product. The crude product was purified by glass column to afford 4-((5-bromopentyl)oxy)benzonitrile (15 g, 66.94%) which was used in the next step without further purification.

Analytical Data

LCMS: 268 $[M+1]]^+$

Step 2

To a stirred solution of 5-hydroxypyrimidine-2-carbonitrile (0.3 g, 2.47 mmol, 1.0 eq.) in acetone (10 mL) was added compound of 4-((5-bromopentyl)oxy)benzonitrile (0.79 g, 2.97 mmol, 1.2 eq.) and potassium carbonate (0.68 g, 4.95 mmol, 2.0 eq.) at 70° C. for 2 h. The reaction mixture was monitored by TLC and LCMS. The reaction mixture was diluted with water (50 mL) and extracted with EtOAC (3×40 mL). The separated organic layer were dried over anhydrous $Na_2SO_4$ and concentrated under reduced pressure to get crude product. The crude product was purified by Combi-Flash chromatography to afford 5-((5-(4-cyanophenoxy)pentyl)oxy)pyrimidine-2-carbonitrile (0.2 g, 32.76%) which was used in the next step without further purification.

Analytical Data

LCMS: 309 $[M+1]^+$

Step 3

To a stirred suspension of $NH_4Cl$ (0.34 g, 6.49 mmol, 8.0 eq.) in toluene (5 mL) at 0° C. was added trimethylaluminum (3.2 mL, 6.49 mmol, 8.0 eq.). The reaction mixture was allowed to stir at 0° C. for 10 minutes followed by stirring at RT for 15 minutes. To this solution was added 5-((5-(4-cyanophenoxy)pentyl)oxy)pyrimidine-2-carbonitrile (0.25 g, 0.81 mmol, 1.0 eq.) and reaction mixture was allowed to stir at RT for 15 min. The reaction mixture was then stirred under reflux for 18 h. The reaction mixture was cooled to RT and methanol was added (5 mL) under ice cooled condition and reaction mixture was allowed to stir at RT for 30 min. The reaction mixture was diluted with 1N HCL (20 mL) and washed with ethyl acetate (20 mL). The aqueous layer was basified with 1N NaOH solution (15 mL) and extracted with ethanol-ethyl acetate (3×20 mL, 20%). The separated organic layer was dried over anhydrous $Na_2SO_4$ and concentrated under vacuum to afford crude material (0.260 g) which was purified by reversed phase HPLC to afford 4-((5-((3-aminobenzo[d]isoxazol-6-yl)oxy)pentyl)oxy)benzimidamide as diformate salt. The solid was dissolved in 1.25 M HCl in ethanol (8 mL), solvent was evaporated under reduced pressure to obtain solid, which after lyophilization afforded 5-((5-(4-carbamimidoylphenoxy)pentyl)oxy)pyrimidine-2-carboximidamide as dihydrochloride salt (0.01 g, 5.36%).

Analytical Data

LCMS: 343 $([M+1])^+$ $^1$H NMR (400 MHz, DMSO-$d_6$) δ 9.53 (br. s., 2H), 9.30 (br. s., 2H), 9.15 (br. s., 2H), 8.82 (s, 2H), 8.78 (br. s., 2H), 7.82 (d, J=8.33 Hz, 2H), 7.16 (d, J=8.33 Hz, 2H), 4.35 (t, J=6.14 Hz, 2H), 4.13 (t, J=6.36 Hz, 2H), 1.76-1.91 (m, 4H), 1.61 (br. s., 2H)

Example 4

Preparation of 5-((5-(4-carbamimidoylphenoxy)pentyl)oxy)pyrazine-2-carboximidamide Compound 4

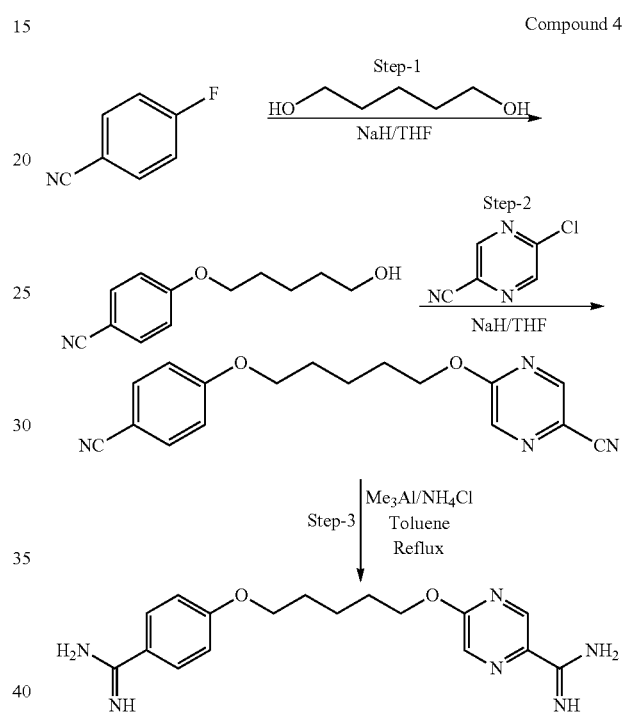

Step 1

To a solution of pentane-1,5-diol (0.86 g, 8.26 mmol, 1 eq.) in THF (10 mL) was added NaH (0.33 g, 8.26 mmol, 1 eq.) reaction mixture was allowed to stir at 0° C. for 20 minutes. To this solution was added 4-fluorobenzonitrile (1 g, 8.26 mmol, 1 eq.) and the reaction mixture was allowed to stir at 60° C. for 2 h. Progress of reaction was monitored by TLC. After consumption of starting material, reaction mixture was diluted with water (50 mL) and extracted with ethyl acetate (2×200 mL). Combined organic layer was washed with water (3×50 mL), dried over anhydrous sodium sulfate and concentrated under reduced pressure to afford 4-((5-hydroxypentyl)oxy)benzonitrile (0.8 g, 47.33%)

Analytical Data

LCMS: 206 $[M+1]^+$

Step 2

To a solution of 4-((5-hydroxypentyl)oxy)benzonitrile (0.5 g, 2.43 mmol, 1 eq.) in THF (10 mL) was added NaH (0.117 g, 2.92 mmol, 1.2 eq.). The reaction mixture was allowed to stir at 0° C. for 20 minutes, after which time 5-chloropyrazine-2-carbonitrile (0.306 g, 2.19 mmol, 0.9 eq.) was added and the reaction mixture was allowed to stir at RT for 2 h. Progress of reaction was monitored by TLC. After consumption of starting material, reaction mixture was diluted with water (50 mL) and extracted with ethyl acetate (2×200 mL). The combined organic layer was washed with water (3×50 mL), dried over anhydrous sodium sulfate and concentrated under reduced pressure to afford 5-((5-(4-cyanophenoxy)pentyl)oxy)pyrazine-2-carbonitrile (0.4 g, 53.26%)

Analytical Data

LCMS: 309 [M+1]$^+$

Step 3

To a suspension of ammonium chloride (555 mg, 10.39 mmol, 8 eq.) in toluene (5 mL) was added trimethylaluminum (5.2 mL, 10.39 mmol, 8 eq.) dropwise at 0° C. The mixture was allowed to stir at the same temperature for 10 minutes followed by stirring at RT for 15 minutes. To this mixture was added 5-((5-(4-cyanophenoxy)pentyl)oxy) pyrazine-2-carbonitrile (400 mg, 1.30 mmol, 1 eq.) and reaction mixture was allowed to stir at RT for 15 minutes. The reaction mixture was then allowed to stir at under reflux for 18 h. Reaction mixture was cooled to RT, diluted with methanol (5 mL) and allowed to stir at RT for 30 minutes. Reaction mixture was diluted with 3M aq. HCl (25 mL) and washed with ethyl acetate (20 mL). Aqueous layer was basified with 5N NaOH (20 mL) and extracted with a solution of 1:5 mixture of ethanol-ethyl acetate (3×25 mL). Combined organic layer was dried over anhydrous sodium sulfate. Removal of solvent afforded crude material which was purified by reversed phase HPLC to afford 5-((5-(4-carbamimidoylphenoxy)pentyl)oxy)pyrazine-2-carboximidamide as free base. The solid was dissolved in 1.25 M HCl (5 mL), the solution was concentrated under vacuum and lyophilized to afford 5-((5-(4-carbamimidoylphenoxy)pentyl)oxy)pyrazine-2-carboximidamide as di HCl salt (50 mg, 11.26%).

Analytical Data

LCMS: 343 [M+1]$^+$ $^1$H NMR (400 MHz, DMSO-d$_6$) 9.45 (bs, 2H), 9.20 (bs, 2H), 9.15 (bs, 2H), 9.07 (s, 1H), 8.80 (bs, 2H), 8.49 (s, 1H), 7.80 (d, 4H), 7.17 (d, 4H), 4.42 (t, 2H), 4.08 (t, 4H), 1.70-1.90 (m, 4H), 1.50-1.65 (m, 2H).

Example 5

Preparation of 5-(4-(4-carbamimidoylphenoxy)butoxy)picolinimidamide

Compound 5

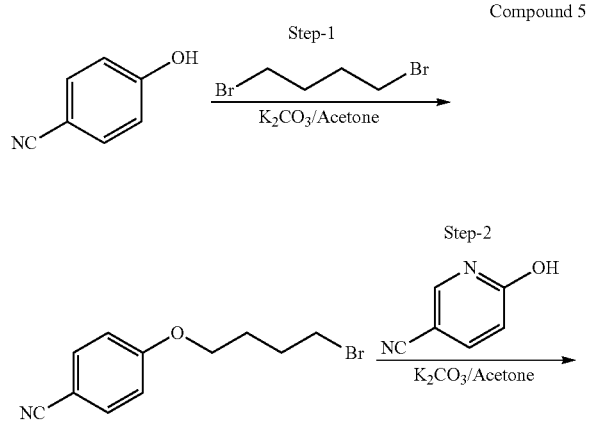

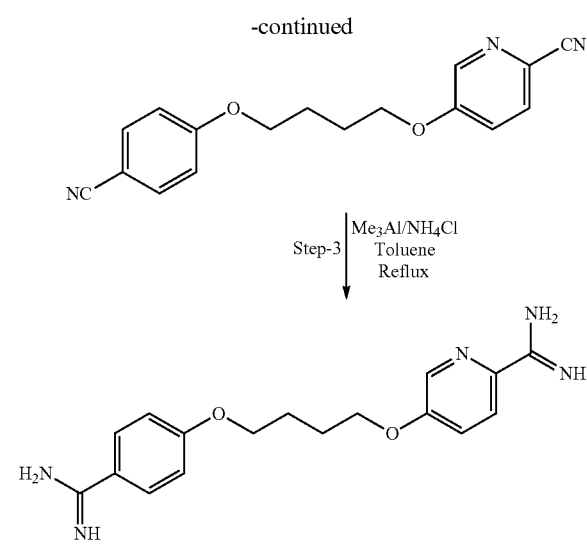

Step 1

To a solution of 4-hydroxybenzonitrile (1 g, 8.39 mmol, 1 eq.) in acetone (10 mL) were added K$_2$CO$_3$ (2.32 g, 16.78 mmol, 2 eq.) and 1,4-dibromobutane (7.25 g, 33.56 mmol, 4 eq.) and the reaction mixture was allowed to stir under reflux for 2 h. Progress of reaction was monitored by TLC. After consumption of starting material, the reaction mixture was extracted with ethyl acetate (2×200 mL). Combined organic layer was washed with water (3×50 mL), dried over anhydrous sodium sulfate and concentrated under reduced pressure. The crude material obtained was purified by Combi-Flash using ethyl acetate-hexane to afford 4-(4-bromobutoxy)benzonitrile (1.5 g, 70.42%)

Analytical Data

LCMS: 255 [M+1]$^+$

Step 2

To a solution of 6-hydroxynicotinonitrile (0.2 g, 1.65 mmol, 1 eq) in acetone (10 mL) was added K$_2$CO$_3$ (0.57 g, 4.162 mmol, 2.5 eq) and 4-(bromobutoxy)benzonitrile (0.50 g, 1.99 mmol, 1.2 eq) and the reaction mixture was allowed to stir at 70° C. for 2 h. Progress of reaction was monitored by TLC. The reaction mixture was cooled to RT, diluted with water (150 mL) and allowed to stir at RT for 10 minutes. The precipitate was filtered and dried under vacuum to afford (0.3 g, 61.47%) of 5-(4-(4-cyanophenoxy) butoxy)picolinonitrile, which was used in the next step without further purification.

Analytical Data

LCMS: 294 [M+1]$^+$

Step 3

To a suspension of ammonium chloride (370 mg, 6.81 mmol, 8 eq) in toluene (8 mL) was added trimethylaluminum (3.41 mL, 6.81 mmol, 8 eq.) dropwise at 0° C. The mixture was allowed to stir at the same temperature for 10 minutes followed by stirring at RT for 15 minutes. To this mixture was added 5-(4-(4-cyanophenoxy)butoxy)picolinonitrile (250 mg, 0.85 mmol) and reaction mixture was allowed to stir at RT for 15 minutes. The reaction mixture was then allowed to stir under reflux for 18 h. Reaction mixture was cooled to RT, diluted with methanol (5 mL) and allowed to stir at RT for 30 minutes. Reaction mixture was diluted with 3M aq. HCl (25 mL) and washed with ethyl acetate (20 mL). The aqueous layer was basified with 5N NaOH (20 mL) and extracted with a solution of 1:5 mixture of ethanol-ethyl acetate (3×25 mL). Combined organic layer was dried over anhydrous sodium sulfate. Removal of solvent afforded crude which was purified by reversed phase HPLC to afford 5-(4-(4-carbamimidoylphenoxy)butoxy)picolinimidamide as free base. Solid was dissolved in 1.25 M HCl (5 mL), the solution was concentrated under vacuum and lyophilized to afford 5-(4-(4-carbamimidoylphenoxy)butoxy)picolinimidamide as a di-HCl salt (80 mg, 28.77%).
Analytical Data
LCMS 328 [M+1]
$^1$H NMR (400 MHz, DMSO-d6) δ 9.41 (brs, 2H), 9.20 (brs, 2H), 9.16 (brs, 2H), 8.85 (brs, 2H), 8.46 (s, 1H), 8.32 (d, 1H), 7.82 (d, 2H), 7.71 (d, 1H), 7.18 (d, 2H), 4.20-4.28 (m, 2H), 4.10-4.19 (m, 2H), 1.85-1.96 (m, 4H).

Example 6

Preparation of 5-(4-(4-carbamimidoylphenoxy)butoxy)picolinimidamide

Compound 6

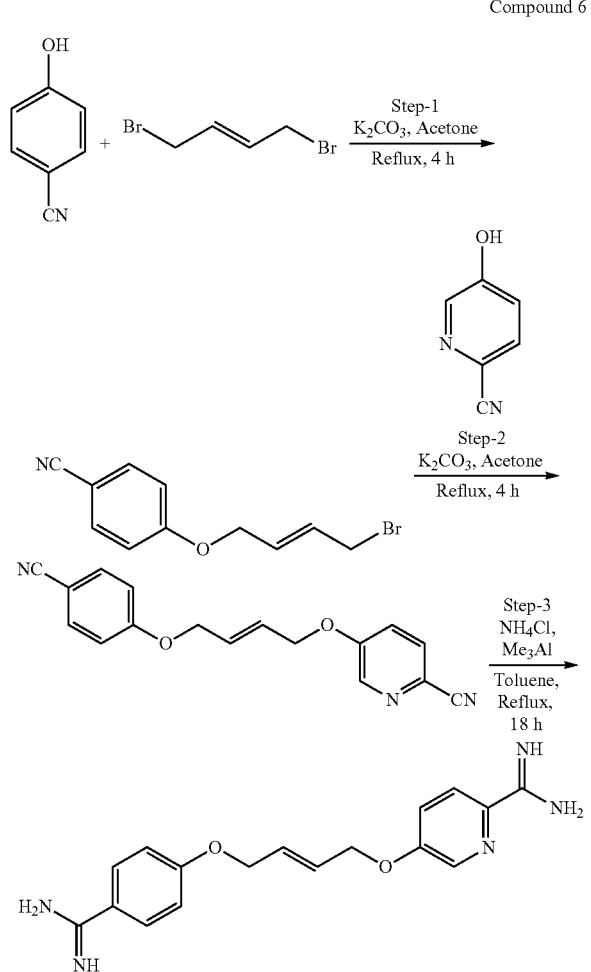

Step 1

To a solution of 4-hydroxybenzonitrile (1.0 g, 8.40 mmol, 1 eq.) in acetone (20 mL) under inert atmosphere were added sequentially K$_2$CO$_3$ (2.3 g, 16.80 mmol, 2 eq.) and (E)-1,4-dibromobut-2-ene (5.4 g, 25.21 mmol, 3 eq.) at room temperature. The resulting mixture was stirred at reflux temperature for 4 h. Progress of reaction was monitored by TLC. After completion the reaction mixture was diluted with water (200 mL) and extracted with ethyl acetate (3×300 mL) organic layer was dried over anhydrous sodium sulphate. Removal of solvent under reduced pressure gave solid which was triturated with ether and pentane to (E)-4-((4-bromobut-2-en-1-yl)oxy)benzonitrile (1.68 g, 80%).
Analytical Data
LCMS: 253 [M+1]$^+$
Step 2

To a solution of 5-hydroxypicolinonitrile (0.2 g, 1.66 mmol, 1 eq.) in acetone (20 mL) under inert atmosphere were added sequentially K$_2$CO$_3$ (0.46 g, 3.2 mmol, 2 eq.) and (E)-4-((4-bromobut-2-en-1-yl)oxy)benzonitrile (0.5 g, 1.99 mmol, 0.5 eq.) at room temperature. The resulting mixture was stirred at refluxed temperature for 4 h. Progress of reaction was monitored by TLC. After completion the reaction mixture was diluted with water (100 mL) and extracted with ethyl acetate (3×100 mL) organic layer was dried over anhydrous sodium sulphate. Removal of solvent under reduced pressure gave solid which was triturated with ether and pentane to (E)-5-((4-(4-isocyanophenoxy)but-2-en-1-yl)oxy)picolinonitrile (0.25 g, 51%).
Analytical Data
LCMS: 292 [M+1]$^+$
Step 3

To a suspension of ammonium chloride (0.54 g, 10.13 mmol, 8 eq.) in toluene (10 mL) was added trimethylaluminum (5 mL, 10.13 mmol, 8 eq.) dropwise at 0° C. The mixture was allowed to stir at the same temperature for 10 minutes followed by stirring at room temperature for 15 minutes. To this mixture was added (E)-5-((4-(4-isocyanophenoxy)but-2-en-1-yl)oxy)picolinonitrile (0.37 g, 1.267 mmol, 1 eq.) and reaction mixture was allowed to stir at room temperature for 15 minutes. The reaction mixture was then allowed to stir under reflux for 18 h. The reaction mixture was cooled to RT, diluted with methanol (5 mL) and allowed to stir at RT for 30 minutes. Reaction mixture was diluted with 3M aq. HCl (20 mL) and washed with ethyl acetate (20 mL). Aqueous layer was basified with 5N NaOH (15 mL) and extracted with ethanol-ethyl acetate (20%, 3×50 mL). Combined organic layer was dried over anhydrous sodium sulphate. Removal of solvent afforded crude which was purified by reversed phase HPLC to 5-(4-(4-carbamimidoylphenoxy)butoxy)picolinimidamide as free base. Solid was dissolved in 1.25 M HCl (5 mL), the solution was concentrated under vacuum and lyophilized to afford 5-(4-(4-carbamimidoylphenoxy)butoxy)picolinimidamide as di-HCl salt (0.05 g, 12.07
Analytical Data
LCMS: 326 [M+1]
$^1$H NMR (400 MHz, DMSO-d6) δ 9.40 (brs, 2H), 9.08 (brs, 2H), 8.82 (brs, 2H), 8.53 (brs, 2H), 8.30 (d, 1H), 7.82 (d, 2H), 7.74 (d, 1H), 7.19 (d, 2H), 6.17 (brs, 2H), 4.82 (brs, 2H), 4.74 (brs, 2H).

Example 7

Preparation of 5,5'-(pentane-1,5-diylbis(oxy))bis(pyrazine-2-carboximidamide)

Compound 7

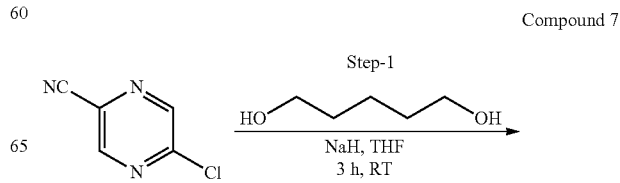

-continued

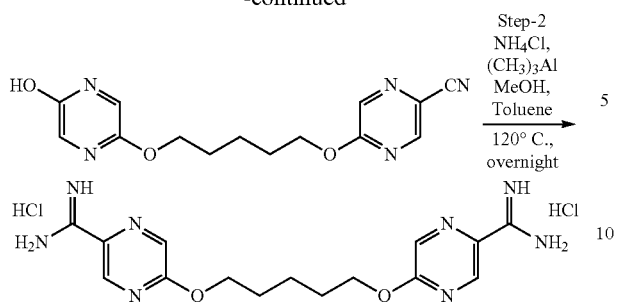

Step 1

To a stirred solution of pentane-1,5-diol (0.22 g, 2.15 mmol, 1 eq.) in THF (10 mL) at 0° C. was added NaH (0.26 g, 6.44 mmol, 3.0 eq.) and the reaction mixture was allowed to stir at the same temperature for 10 minutes. To this solution was added 5-chloropyrazine-2-carbonitrile (0.30 g, 2.14 mmol, 3.0 eq.) and the resulting mixture was allowed to stir at RT for 3 h. Progress of reaction was monitored by TLC and LCMS. After completion, reaction mixture was diluted with water (50 mL) and extracted with ethyl acetate (2×100 mL). Combined organic layer was dried over anhydrous $Na_2SO_4$ and concentrated under reduced pressure to obtain crude product. The crude product was purified by Combi-Flash on silica gel using ethyl acetate-hexane system as eluent to afford 5, 5'-(pentane-1, 5-diylbis (oxy)) bis (pyrazine-2-carbonitrile) (0.36 g, 53.81%).

Analytical Data

LCMS: 311 [M+1]]$^+$

Step 2

To a stirred suspension of $NH_4Cl$ (1.10 g, 20.64 mmol, 16 eq.) in toluene (10 mL) at 0° C. was added trimethylaluminum (10.32 mL, 20.64 mmol, 16 eq.). The reaction mixture was allowed to stir at 0° C. for 10 minutes followed by stirring at RT for 15 minutes. To this solution was added 5, 5'-(pentane-1, 5-diylbis (oxy)) bis(pyrazine-2-carbonitrile) (0.40 g, 1.29 mmol, 1.0 eq.) and reaction mixture was allowed to stir at RT for 15 minutes. The reaction mixture was then stirred under reflux for 18 h. The reaction mixture was cooled to RT and methanol (5 mL) was added under ice cooling and the reaction mixture was allowed to stir at RT for 30 minutes. The reaction mixture was diluted with 1N HCL (20 mL) and washed with ethyl acetate (20 mL). Aqueous layer was basified with 1N NaOH solution (15 mL) and extracted with ethanol-ethyl acetate (20%, 3×20 mL). The separated organic layer was dried over anhydrous $Na_2SO_4$ and concentrated under vacuum to afford crude product (0.35 g) which was purified by reversed phase HPLC to afford 5,5'-(pentane-1,5-diylbis(oxy))bis(pyrazine-2-carboximidamide) 5-5-(hepta-1, 6-diyne-1, 7-diyl) as diformate salt. The solid was dissolved in 1.25 M HCl in ethanol (8 mL), after which the solvent was evaporated under reduced pressure. The solid obtained was lyophilized to afford 5,5'-(pentane-1,5-diylbis(oxy))bis(pyrazine-2-carboximidamide) as a dihydrochloride salt (0.08 g, 13.25%).

Analytical Data

LCMS: 345 ([M+1])$^+$ $^1$H NMR (400 MHz, DMSO-d$_6$) δ 9.52 (brs, 4H), 9.24 (brs, 4H), 9.05-9.12 (brs, 2H), 8.52 (brs, 2H), 4.47 (t, 4H), 1.92-1.80 (m, 4H), 1.55-1.65 (m, 2H)

Example 8

Preparation of 6,6'-(heptane-1,7-diyl)dipicolinimidamide

Compound 8

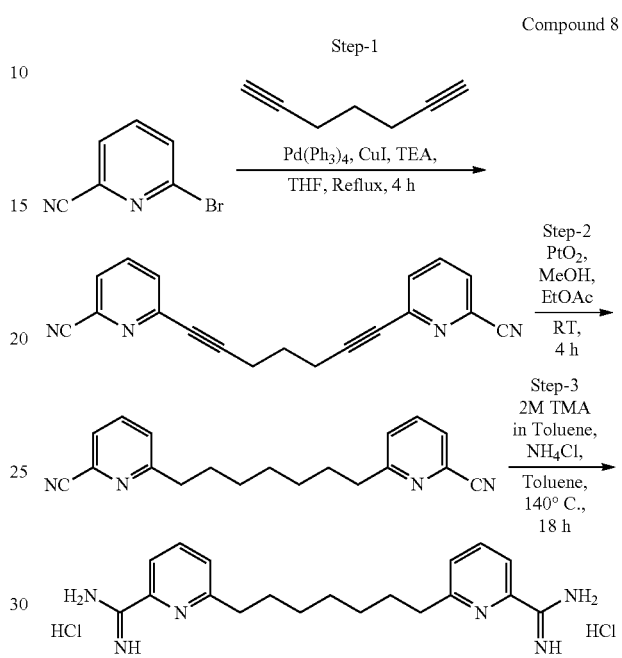

Step 1

To a stirred solution of hepta-1,6-diyne (0.30 g, 3.26 mmol, 1.0 eq.) in THF (20 mL) were added 6-bromopicolinonitrile (1.8 g, 9.38 mmol, 3.0 eq.), triethylamine (1.37 mL, 9.38 mmol, 3.0 eq.) and CuI (62 mg, 0.32 mmol, 0.1 eq.). The resulting reaction mixture was deoxygenated by purging with nitrogen for 20 minutes. To this mixture was added (Ph$_3$P)$_4$Pd (0.188 g, 0.163 mmol, 0.05 eq.) and the reaction mixture was again deoxygenated by purging with nitrogen for 10 minutes. The reaction mixture was allowed to stir at 60° C. for 4 h. Progress of reaction was monitored by TLC. After completion, reaction mixture was cooled to RT, diluted with water and extracted with ethyl acetate (3×50 mL). Combined organic layer was washed with brine, dried over sodium sulphate and evaporated under reduced pressure to afford crude which was purified on Combi-Flash on silica gel using ethyl acetate-hexane system as eluent to afford 6,6'-(hepta-1,6-diyne-1,7-diyl)dipicolinonitrile (400 mg, 40.40%).

Analytical Data

LCMS: 297 [M+1]$^+$

Step 2

To a stirred suspension of 6,6'-(hepta-1,6-diyne-1,7-diyl) dipicolinonitrile (0.3 g, 1.01 mmol) in a solution of ethyl acetate (10 mL) and methanol (10 mL) was added Pt/O$_2$ (40 mg). The reaction mixture was allowed to stir at RT under hydrogen atmosphere for 2 h. Progress of reaction was monitored by TLC and $^1$H NMR. After completion, reaction mixture was filtered through celite-bed and the bed was washed with ethyl acetate (20 mL). The filtrate was evaporated under reduced pressure to afford crude which was purified by Combi-Flash on silica gel using ethyl acetate-hexane system as eluent to obtain 6,6'-(heptane-1,7-diyl) dipicolinonitrile (250 mg, 82.50%).

Analytical Data

LCMS: 305 [M+1]$^+$

Step 3

To a stirred suspension of NH$_4$Cl (0.32 g, 6.052 mmol, 8 eq.) in toluene (8 mL) at 0° C. was added 2M solution of trimethylaluminum in toluene (3 mL, 6.052 mmol, 8 eq.). The reaction mixture was allowed to stir at 0° C. for 10 minutes followed by stirring at RT for 15 minutes. To this solution was added 6,6'-(heptane-1,7-diyl)dipicolinonitrile (0.230 g, 0.75 mmol, 1.0 eq.) and reaction mixture was allowed to stir at RT for 15 minutes. The reaction mixture was then stirred under reflux for 18 h. The reaction mixture was cooled to RT and to it was added methanol (5 mL) under ice cooling and then allowed to stir at RT for 30 minutes. The reaction mixture was diluted with 1N HCl (20 mL) and washed with ethyl acetate (20 mL). Aqueous layer was basified with 1N NaOH solution (15 mL) and extracted with ethanol-ethyl acetate (20%, 3×20 mL). The separated organic layer were dried over anhydrous Na$_2$SO$_4$ and concentrated under vacuum to afford crude product (0.3 g) which was purified by reverse phase HPLC to obtain 6,6'-(heptane-1,7-diyl)dipicolinimidamide as a diformate salt. Solid was dissolved in 1.25 M HCl in ethanol (8 mL), solvent was evaporated under reduced pressure and the material obtained was lyophilized to afford 6,6'-(heptane-1,7-diyl)dipicolinimidamide as a dihydrochloride salt (0.06 g, 21.89%).

Analytical Data

LCMS: 339 [M+1]$^+$ $^1$H NMR (400 MHz, DMSO-d6) δ 9.50 (brs, 8H), 8.20 (d, 2H), 8.04 (t, 2H), 7.62 (d, 2H), 6.60 (brs, 2H), 2.82 (t, 4H), 1.78-1.63 (m, 4H), 1.40-1.20 (m, 6H).

Example 9

Preparation of 5,5'-(heptane-1,7-diyl)dinicotinimidamide

Compound 9

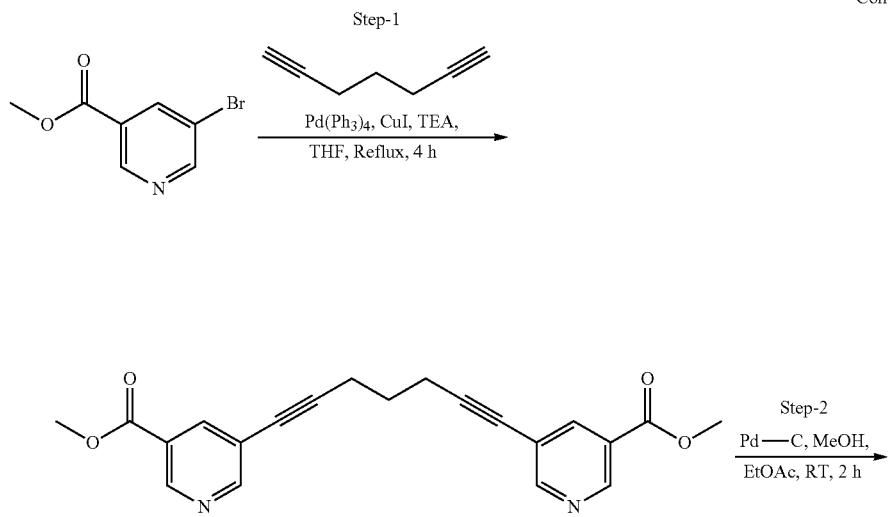

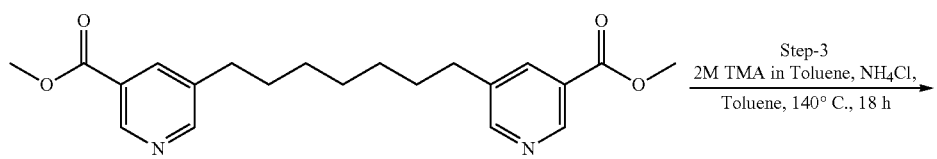

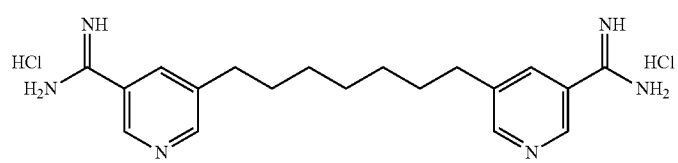

Step 1

To a stirred solution of hepta-1,6-diyne (0.1 g, 1.089 mmol, 1.0 eq.) in THF (10 mL) were added methyl 5-bromonicotinate (0.69 g, 3.62 mmol, 3.0 eq.), triethylamine (0.45 mL, 3.26 mmol, 3.0 eq.) and CuI (20 mg, 0.108 mmol, 0.1 eq.). The resulting reaction mixture was deoxygenated by purging with $N_2$ for 20 minutes. Then Pd(PPh$_3$)$_4$ (62 mg, 0.0544 mmol, 0.05 eq.) was added and again the reaction mixture was deoxygenated by purging with nitrogen for 10 minutes. The reaction mixture was allowed to stir at 70° C. for 4 h. Progress of reaction was monitored by TLC. After completion, reaction mixture was brought to RT, diluted with water (20 mL) and extracted with ethyl acetate (3×30 mL). Combined organic layer was washed with brine (20 mL), dried over sodium sulphate and evaporated under reduced pressure to afford crude material which was purified by column chromatography on silica gel using ethyl acetate-hexane system as eluent to afford dimethyl 5,5'-(hepta-1,6-diyne-1,7-diyl)dinicotinate (180 mg, 45.80%).

Analytical Data

LCMS: 343.4 [M+1]$^+$

Step 2

To a stirred suspension of dimethyl 5,5'-(hepta-1,6-diyne-1,7-diyl)dinicotinate (0.18 g, 0.593 mmol) in methanol (5 mL) was added Pd—C (150 mg). The reaction mixture was allowed to stir at room temperature under hydrogen atmosphere for 2 h. Progress of reaction was monitored by TLC and $^1$H NMR. After completion of reaction mixture was filtered through celite-bed and the bed was washed with ethyl acetate (20 mL) and the filtrate was evaporated under reduced pressure to afford crude material which was purified by column chromatography on silica gel using ethyl acetate-hexane system as eluent to afford dimethyl 5,5'-(heptane-1,7-diyl)dinicotinate (120 mg, 65.57%).

Step 3

To a stirred suspension of NH$_4$Cl (0.15 g, 2.91 mmol, 8 eq.) in toluene (5 mL) at 0° C. was added 2M solution of trimethylaluminum in toluene (1.45 mL, 2.909 mmol, 8 eq.). The reaction mixture was allowed to stir at 0° C. for 10 minutes followed by stirring at RT for 15 minutes. To this solution was added dimethyl 5,5'-(heptane-1,7-diyl)dinicotinate (0.12 g, 0.363 mmol, 1.0 eq.) and reaction mixture was allowed to stir at RT for 15 minutes. The reaction mixture was then stirred under reflux for 18 h. The reaction mixture was cooled to RT and to it was added methanol (3 mL) under ice cooling and the reaction mixture was allowed to stir at RT for 30 minutes. The reaction mixture was diluted with 1N HCl (20 mL) and washed with ethyl acetate (20 mL). Aqueous layer was basified with 1N NaOH solution (15 mL) and extracted with ethanol-ethyl acetate (20%, 3×20 mL). The separated organic layer were dried over anhydrous Na$_2$SO$_4$ and concentrated under vacuum to afford crude (0.3 g) which was purified by reversed phase HPLC to afford 5,5'-(heptane-1,7-diyl)dinicotinimidamide as diformate salt. Solid was dissolved in 1.25 M HCl in ethanol (8 mL), solvent was evaporated under reduced pressure to provide a solid which was lyophilized to afford 5,5'-(heptane-1,7-diyl)dinicotinimidamide as a dihydrochloride salt (0.022 g, 14.59%).

Analytical Data

LCMS: 339.3 [M+1]$^+$ $^1$H NMR (400 MHz, DMSO-d6) δ 9.55 (brs, 4H), 9.25 (brs, 4H), 8.81 (s, 2H), 8.75 (s, 2H), 8.08 (s, 2H), 2.70-2.60 (m, 4H), 1.70-1.55 (m, 4H), 1.40-1.22 (m, 6H).

Example 10

Preparation of 6,6'-(heptane-1,7-diyl)dinicotinimidamide

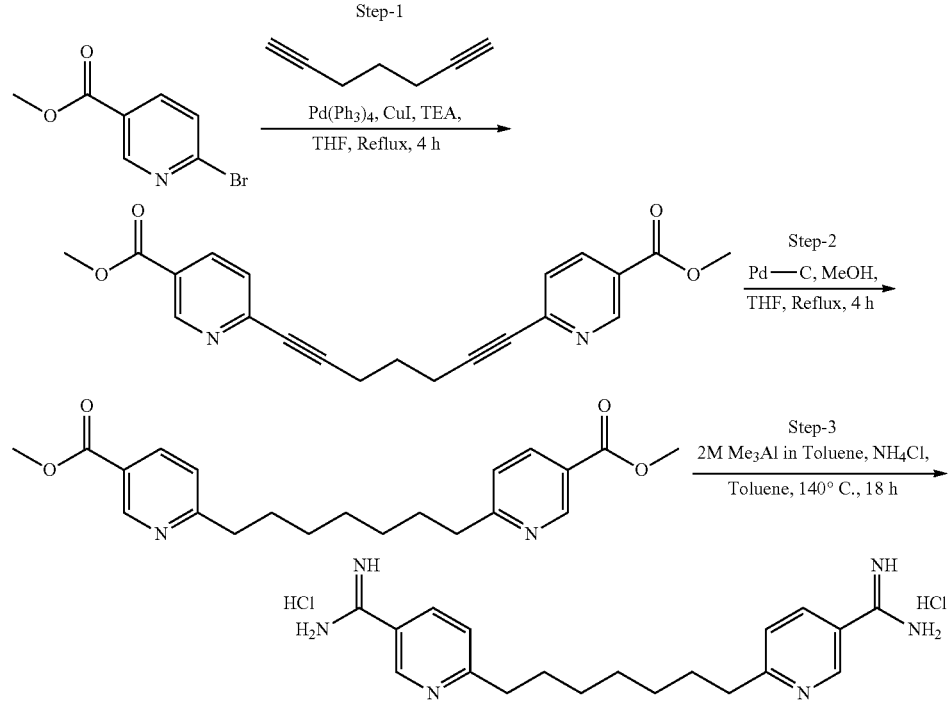

Compound 10

Step 1

To a stirred solution of hepta-1,6-diyne (0.25 g, 2.71 mmol, 1.0 eq.) in THF (20 mL) were added methyl 6-bromonicotinate (1.46 g, 6.79 mmol, 2.5 eq.), triethylamine (1.14 mL, 8.13 mmol, 3.0 eq.) and CuI (52 mg, 0.271 mmol, 0.1 eq.) and the resulting mixture was deoxygenated by purging with $N_2$ for 20 minutes. To this mixture was added Pd(PPh$_3$)$_4$ (156 mg, 0.135 mmol, 0.05 eq.) and again the reaction mixture was deoxygenated by purging with $N_2$ for 10 minutes. The reaction mixture was allowed to stir at 60° C. for 4 h. Progress of reaction was monitored by TLC. After completion, reaction mixture was brought to room temperature, diluted with water (30 mL) and extracted with ethyl acetate (3×35 mL). Combined organic layers were washed with brine (30 mL), dried over sodium sulphate and evaporated under reduced pressure to afford crude product which was purified by column chromatography on silica gel using ethyl acetate-hexane system as eluent to afford dimethyl 6,6'-(hepta-1,6-diyne-1,7-diyl)dinicotinate (0.95 g, 96.93%).
Analytical Data
LCMS: 363.3 [M+1]$^+$
Step 2

To a stirred suspension of dimethyl 6,6'-(hepta-1,6-diyne-1,7-diyl)dinicotinate (0.95 g, 2.76 mmol) in methanol (15 mL) and ethyl acetate (5 mL) was added Pd—C (1 g). The reaction mixture was allowed to stir at RT under hydrogen atmosphere for 2 h. Progress of reaction was monitored by TLC and $^1$H NMR. After completion, the mixture was filtered through celite-bed, the bed washed with ethyl acetate (50 mL) and filtrate was evaporated under reduced pressure to afford crude which was purified by column chromatography on silica gel using ethyl acetate-hexane system as eluent to afford dimethyl 6,6'-(heptane-1,7-diyl)dinicotinate (0.6 g, 61.79%)
Step 3

To a stirred suspension of NH$_4$Cl (0.19 g, 3.51 mmol, 10 eq.) in toluene (7 mL) at 0° C. was added 2M solution of trimethylaluminum in toluene (1.75 mL, 3.51 mmol, 10 eq.). The reaction mixture was allowed to stir at 0° C. for 10 minutes followed by stirring at RT for 15 minutes. To this solution was added dimethyl 6,6'-(heptane-1,7-diyl)dinicotinate (0.13 g, 0.351 mmol, 1.0 eq.) and reaction mixture was allowed to stir at room temperature for 15 minutes. The reaction mixture was then stirred under reflux for 18 h. The reaction mixture was cooled to RT and to it was added methanol (5 mL) under ice cooled condition and reaction mixture was allowed to stir at RT for 30 minutes. The reaction mixture was diluted with 1N HCl (30 mL) and washed with ethyl acetate (20 mL). Aqueous layer was basified with 1N NaOH solution (25 mL) and extracted with ethanol-ethyl acetate (20%, 3×60 mL). The separated organic layer were dried over anhydrous Na$_2$SO$_4$ and concentrated under vacuum to afford crude (0.3 g) which was purified by reversed phase HPLC to obtain 5,5'-(heptane-1,7-diyl)dinicotinimidamide as diformate salt. Solid was dissolved in 1.25 M HCl in ethanol (8 mL), solvent was evaporated under reduced pressure to provide a solid which after lyophilization afforded 6,6'-(heptane-1,7-diyl)dinicotinimidamide as dihydrochloride salt (0.012 g, 10.16%).
Analytical Data
LCMS: 339.2 [M+1]$^+$
$^1$H NMR (400 MHz, DMSO-d$_6$) δ 9.30-9.44 (brs, 4H), 8.97-9.13 (brs, 4H), 8.81-8.92 (s, 2H), 8.01-8.23 (m, 2H), 7.39-7.63 (m, 2H), 2.75-2.93 (m, 4H), 1.60-1.78 (m, 4H), 1.23-1.46 (m, 6H).

Example 11

Preparation of 5-(5-(3-carbamimidoylphenoxy)pentyloxy)picolinimidamide

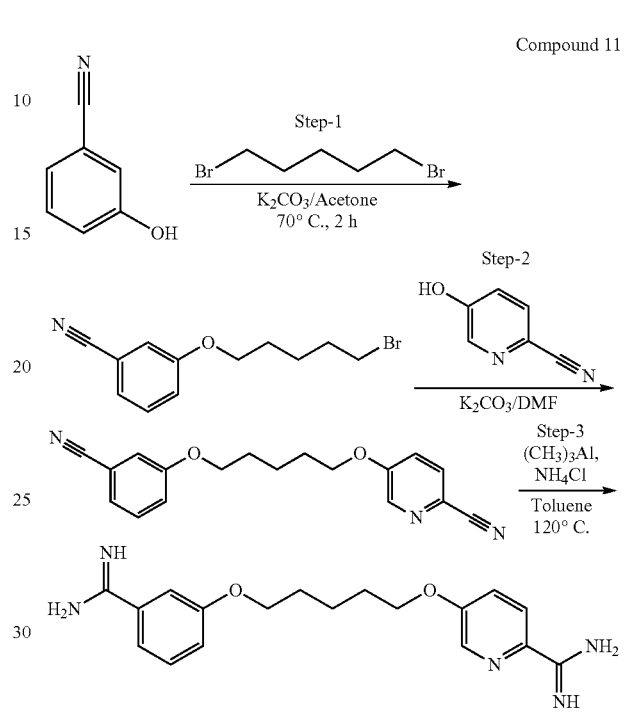

Compound 11

Step 1

To a stirred solution of 3-hydroxybenzonitrile (2.0 g, 16.78 mmol, 1.0 eq.) in acetone (20 mL) were added 1,5-dibromopentane (11.58 g, 3.0 eq.) and K$_2$CO$_3$ (4.41 g, 31.95 mmol, 2 eq.) and the reaction mixture was stirred at 80° C. for 2 h. Progress of reaction was monitored by TLC. After completion, the reaction mixture was filtered and solid was washed with acetone (20 mL). Removal of acetone under reduced pressure afforded oily residue which was purified by column chromatography on silica gel using silica gel using ethyl acetate-hexane system as eluent to afford 3-(5-bromopentyloxy)benzonitrile (3 g, 66.66%).
Analytical Data
LCMS: 268 [M+1]$^+$
Step 2

To a stirred solution of 5-hydroxypyridine-2-carbonitrile (0.2 g, 1.66 mmol, 1 eq.) in DMF (10 mL) were added 3-(5-bromopentyloxy)benzonitrile (0.49 g, 1.83 mmol, 1.1 eq.) and K$_2$CO$_3$ (0.343 g, 2.49 mmol, 1.5 eq.) and the reaction mixture was stirred at 80° C. for 2 h. Progress of reaction was monitored by TLC. After completion, the reaction mixture was diluted with water (50 mL) and extracted with ethyl acetate (3×150 mL). Combined organic layer was dried over sodium sulfate, filtered and evaporated to dryness under vacuum to afford residue which was purified by Comb-Flash on silica gel using ethyl acetate-hexane system as eluent to afford 5-(5-(3-cyanophenoxy)pentyloxy)picolinonitrile (0.3 g, 58.61%).
Analytical Data
LCMS: 308 [M+1]$^+$
Step 3

To a stirred suspension of NH$_4$Cl (0.522 g, 9.76 mmol, 10 eq.) in of toluene (10 mL) at 0° C. was added trimethylaluminum (4.88 ml, 9.76 mmol, 10 eq.) dropwise under nitrogen and the reaction mixture was stirred at 0° C. for 10 minutes followed by stirring at RT for 15 minutes. To this mixture was added 5-{[5-(4-cyanophenoxy)pentyl]oxy}pyridine-2-carbonitrile (1.0 g, 3.25 mmol, 1.0 eq.) was added at 0° C. and the reaction mixture was stirred at RT for 15 minutes. Then the reaction mixture was stirred at 120° C. for 18 h. The reaction mixture was cooled to RT, quenched by dropwise addition of methanol (5 mL) at 0° C. and then allowed to stir at RT for 30 minutes. The reaction mixture was acidified with 3M aq. HCl solution (50 mL) and extracted with ethyl acetate (20 mL). Organic layer was separated and aqueous layer was basified using 5N NaOH solution (50 mL) and extracted with 20% ethanol-ethyl acetate (3×200 mL). Combined organic layer was dried over sodium sulfate, filtered and evaporated to dryness. The residue was completely dried by toluene azeotrope. The residue triturated 50% ethanol-ethyl acetate mixture (2×50 mL) and solid was removed by filtration. Filtrate was evaporated to afford crude which was purified by reversed phase HPLC to afford the 5-(5-(3-carbamimidoylphenoxy)pentyloxy)picolinimidamide free base. This solid was dissolved in 1.25 M HCl in ethanol (5 mL) at 0° C. and ethanol was removed and residue was lyophilized to afford 5-(5-(3-carbamimidoylphenoxy)pentyloxy)picolinimidamide dihydrochloride salt (130 mg, 39

Analytical Data:

LCMS: 342 [M+1]$^+$ $^1$H NMR (400 MHz, DMSO-d$_6$) δ 9.43 (d, 4H), 9.25 (d, 4H), 8.45 (d, 1H), 8.40 (d, 1H), 7.73 (d, 1H), 7.50 (t, 1H), 7.43-7.35 (m, 2H), 7.27 (d, 1H), 4.22 (t, 2H), 4.10 (t, 1H), 1.90-1.78 (m, 4H), 1.66-1.55 (m, 2H).

Example 12

Preparation of 4-((5-((6-carbamimidoylpyridin-3-yl)oxy)pentyl)oxy)picolinimidamide Compound 12

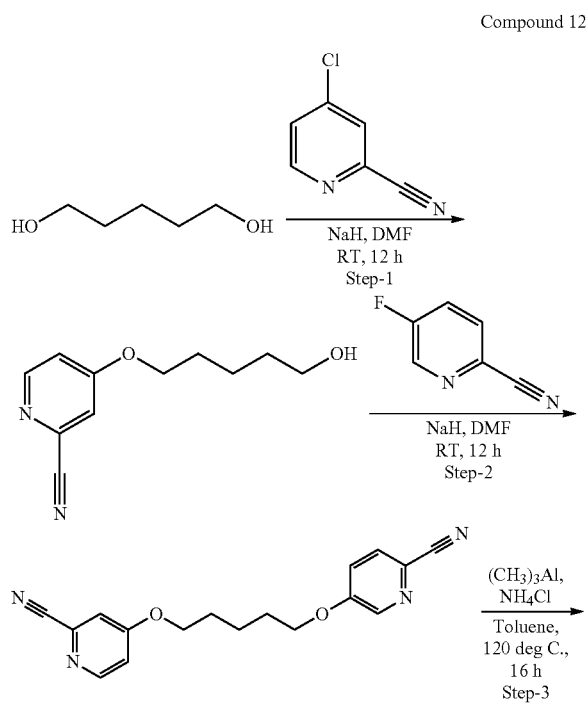

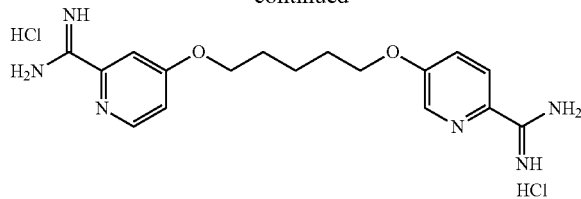

Step 1

To a stirred solution of pentane-1,5-diol (500 mg, 3.62 mmol, 1.0 eq.) in DMF (15 mL) at 0° C. was added NaH (217 mg, 5.43 mmol, 1.5 eq.) and the resulting reaction mixture was stirred at 0° C. for 15 minutes followed by the addition of 4-chloropyridine-2-carbonitrile (754 mg, 7.24 mmol, 2.0 eq.). The reaction mixture was allowed to stir at RT for 12 h. Progress of reaction was monitored by TLC. After consumption of 4-chloropyridine-2-carbonitrile, reaction mixture was diluted with ethyl acetate (50 mL) and washed with water (3×20 mL). Organic layer was dried over sodium sulphate. Removal of ethyl acetate under reduced pressure gave a crude oil which was purified by Combi-Flash on silica gel using ethyl acetate-hexane system as eluent to afford 4-[(5-hydroxypentyl)oxy]pyridine-2-carbonitrile (350 mg, 46.41%).

Step 2

To a stirred solution of 4-[(5-hydroxypentyl)oxy]pyridine-2-carbonitrile (350 mg, 3.62 mmol, 1.0 eq.) in DMF (10 mL) at 0° C. was added NaH (102 mg, 2.53 mmol, 1.5 eq.), the resulting reaction mixture was stirred at 0° C. for 15 minutes followed by the addition of 5-fluoropyridine-2-carbonitrile (413 mg, 3.39 mmol, 2.0 eq). The reaction mixture was allowed to stir at RT for 12 h. Progress of reaction was monitored by TLC. After consumption 4-[(5-hydroxypentyl)oxy]pyridine-2-carbonitrile, reaction mixture was diluted with ethyl acetate (50 mL) and washed with water (3×20 mL). Organic layer was dried over sodium sulphate and concentrated under reduced pressure to afford crude oil which was purified by Combi-Flash on silica gel using ethyl acetate-hexane system as eluent to afford 4-({5-[(6-cyanopyridin-3-yl)oxy]pentyl}oxy)pyridine-2-carbonitrile (185 mg, 35.37%).

Analytical Data:

LCMS: 309 ([M+1])$^+$

Step 3

To a stirred suspension of NH$_4$Cl (257 mg, 4.80 mmol, 8 eq.) in toluene (10 mL) at 0° C. was added trimethylaluminum (2.40 mL, 4.80 mmol, 8 eq.) dropwise under nitrogen. The reaction mixture was stirred at 0° C. for 10 minutes followed by stirring at RT for 15 minutes. Reaction mixture was cooled to 0° C. and 4-({5-[(6-cyanopyridin-3-yl)oxy]pentyl}oxy)pyridine-2-carbonitrile (187 mg, 0.60 mmol, 1 eq.) was added. The reaction mixture was stirred at RT for 15 minutes followed by stirring at 120° C. for 16 h. The reaction mixture was cooled to 0° C. methanol (5 mL) was added dropwise and allowed to stir at RT for 30 minutes. The reaction mixture was acidified with 2M HCl solution (150 mL) and extracted with ethyl acetate (50 mL). Organic layer was separated and aqueous layer was basified with 5N NaOH solution (50 mL) and extracted with 20% ethanol-ethyl acetate (5×200 mL). Combined organic layer was dried over sodium sulphate evaporated to dryness. Traces of water were removed by toluene azeotrope to get solid residue. Solid was triturated with 1:1 ethanol-ethyl acetate (2×200 mL) and filtered. Filtrate was evaporated to dryness and then the residue was purified by reversed phase HPLC to afford 4-((5-((6-carbamimidoylpyridin-3-yl)oxy)pentyl)oxy)picolinimidamide as free base. This solid was dissolved in 1.25 M HCl in ethanol (5 mL) at 0° C., solvent was evaporated to dryness and lyophilized to afford 4-((5-((6-carbamimidoylpyridin-3-yl)oxy)pentyl)oxy)picolinimidamide as hydrochloride salt (20 mg, 7.00%).

Analytical Data

LCMS: 342 [M+1]+

¹H NMR (400 MHz, DMSO-d6) δ d 9.60 (s, 2H), 9.40 (d, 4H), 9.16 (s., 2H), 8.60 (d, 1H), 8.48 (d, 1H), 8.33 (d, 1H), 7.98 (d, 1H), 7.83-7.55 (m, 1H), 7.47-7.27 (m, 1H), 4.23 (t, 4H), 1.97-1.83 (m, 4H), 1.65-1.55 (m, 2H).

Example 13

Preparation of 5-(((1r, 4r)-4-(4-carbamimidoylphenoxy)cyclohexyl)oxy)picolinimidamide Compound 13

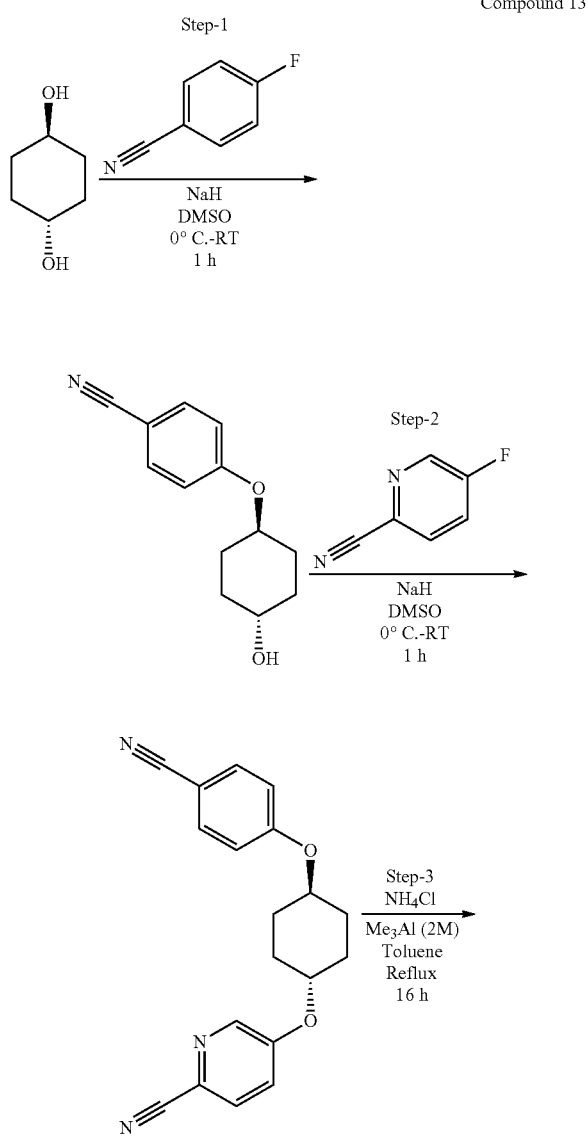

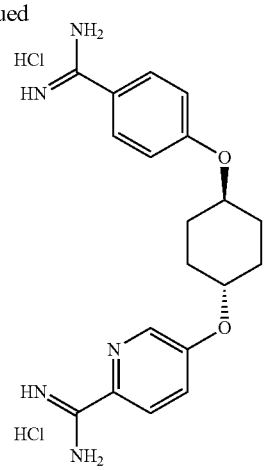

Step 1

To a solution of trans-cyclohexane-1,4-diol (1 g, 8.60 mmol, 1.0 eq.) in DMSO (10 mL) at 0° C. was added, NaH (60% in mineral oil) (104 mg, 4.30 mmol, 0.5 eq.) under inert atmosphere and the resulting mixture was allowed to stir at the same temperature for 15 minutes. To that solution was added 4-fluorobenzonitrile (522 mg, 4.30 mmol, 0.5 eq.) in DMSO (2 mL) and the resulting reaction mixture was allowed to stir at RT for 1 h. Progress of reaction was monitored by TLC. After completion, reaction mixture was diluted with ice cold water (50 mL) and extracted with ethyl acetate (3×200 mL). Combined organic layer was washed with water (5×100 mL) followed by brine (50 mL) and dried over anhydrous sodium sulfate. Removal of solvent under reduced pressure afforded crude material which was purified by Combi-Flash on silica gel using ethyl acetate-hexane system as eluent to afford 4-(((1r,4r)-4-hydroxycyclohexyl)oxy)benzonitrile (900 mg, 50%).

Step 2

To a solution of 4-(((1r, 4r)-4-hydroxycyclohexyl)oxy)benzonitrile (300 mg, 1.38 mmol, 1.0 eq.) in DMSO (5 mL) at 0° C. under inert atmosphere was added NaH (60% in mineral oil) (49.68 mg, 2.07 mmol, 1.5 eq.) and the resulting mixture was allowed to stir at the same temperature for 15 minutes. To that solution was added a solution of 5-fluoropicolinonitrile (202.3 mg, 1.65 mmol, 1.2 eq.) in DMSO (2 mL) and the resulting reaction mixture was allowed to stir at RT for 1 h. Progress of reaction was monitored by TLC. After completion, reaction mixture was diluted with ice-cold water (50 mL) and extracted with ethyl acetate (3×150 mL). Combined organic layer was washed with water (5×100 mL) followed by brine (50 mL) and dried over anhydrous sodium sulfate. Removal of solvent under reduced pressure afforded crude material which was purified by Combi-Flash on silica gel using ethyl acetate-hexane system as eluent to afford 5-(((1r,4r)-4-(4-cyanophenoxy)cyclohexyl)oxy)picolinonitrile (200 mg, 45.35

Step 3

To a suspension of ammonium chloride (267.3 mg, 5.0 mmol, 8 eq.) in toluene (5 mL) was added trimethylaluminum (2M) (721 mg, 2.5 mL, 5.0 mmol, 8 eq.) dropwise at 0° C. The mixture was allowed to stir at the same temperature for 10 minutes followed by stirring at RT for 15 minutes. To this mixture was added 5-(((1r, 4r)-4-(4-cyanophenoxy)cyclohexyl)oxy)picolinonitrile (200 mg, 0.62 mmol, 1.0 eq.) and reaction mixture was allowed to stir at RT for another 15 minutes. The reaction mixture was then allowed to stir under reflux for 16 h. Reaction mixture was cooled to RT, diluted with methanol (5 mL) and allowed to stir at RT for 30 minutes. Reaction mixture was diluted with 1N aq. HCl (25 mL) and washed with ethyl acetate (50 mL). Aqueous layer was basified with 5N NaOH (20 mL) and extracted with a solution of 1:5 mixture of ethanol-ethyl acetate (3×50 mL). Combined organic layer was dried over anhydrous sodium sulfate. Removal of solvent afforded crude material which was purified by reversed phase HPLC to afford 5-(((1r, 4r)-4-(4-carbamimidoylphenoxy)cyclohexyl)oxy)picolinimidamide as free base. Solid was dissolved in 1.25M HCl in EtOH (5 mL) and the solution was concentrated under vacuum and lyophilized to afford 5-(((1r, 4r)-4-(4-carbamimidoylphenoxy)cyclohexyl)oxy)picolinimidamide dihydrochloride salt (5 mg, 4.95%).

Analytical Data

LCMS: 354 [M+1]$^+$ $^1$H NMR (400 MHz, DMSO-d6) δ 8.80-8.54 (m, 6H), 8.46 (d, 1H), 8.27 (d, 1H), 7.82 (d, 2H), 7.77 (d, 1H), 7.20 (d, 2H), 4.76 (brs, 1H), 4.69 (brs, 1H), 2.15-2.00 (m, 4H), 1.75-1.60 (m, 4H).

Example 14

Preparation of 5-(((1s,4s)-4-(4-carbamimidoylphenoxy)cyclohexyl)oxy)picolinimidamide Compound 14

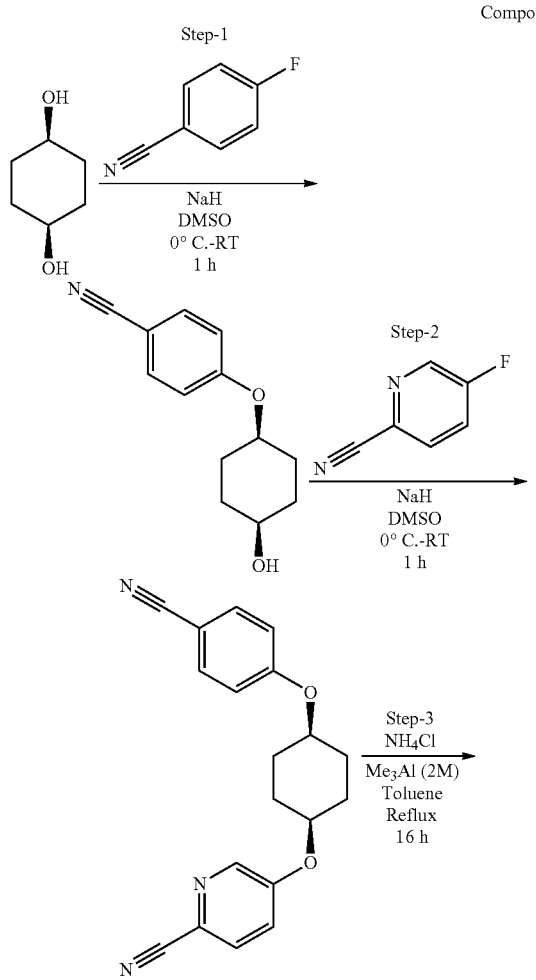

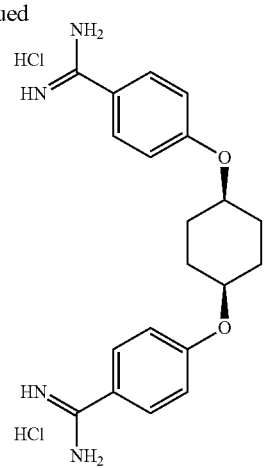

Step 1

To a solution of trans-cyclohexane-1,4-diol (300 mg, 2.58 mmol, 1.0 eq.) in DMSO (5 mL) at 0° C. under inert atmosphere was added NaH (60% in mineral oil) (30.98 mg, 1.29 mmol, 0.5 eq.) and resulting mixture was allowed to stir at the same temperature for 15 minutes. To that solution was added a solution of 4-fluorobenzonitrile (312.9 mg, 2.58 mmol, 1.0 eq.) in DMSO (2 mL) and the resulting reaction mixture was allowed to stir at RT for 1 h. Progress of reaction was monitored by TLC. After completion, reaction mixture was diluted with ice cold water (50 mL) and extracted with ethyl acetate (3×200 mL). Combined organic layer was washed with water (5×100 mL), brine and dried over anhydrous sodium sulfate. Removal of solvent under reduced pressure afforded crude which was purified by Combi-Flash on silica gel using ethyl acetate-hexane system as eluent to afford 4-(((1s,4s)-4-hydroxycyclohexyl)oxy)benzonitrile (200 mg, 71.4%).

Step 2

To a solution of 4-(((1s,4s)-4-hydroxycyclohexyl)oxy)benzonitrile (180 mg, 0.82 mmol, 1.0 eq.) in DMSO (5 mL) at 0° C. under inert atmosphere was added NaH (60% in mineral oil) (29.52 mg, 1.23 mmol, 1.5 eq.) and the resulting mixture was allowed to stir at the same temperature for 15 minutes. To that mixture was a solution of 5-fluoropicolinonitrile (121.4 mg, 0.99 mmol, 1.2 eq.) in DMSO (2 mL) and the resulting reaction mixture was allowed to stir at RT for 1 h. Progress of reaction was monitored by TLC. After completion, reaction mixture was diluted with ice cold water (50 mL) and extracted with ethyl acetate (3×150 mL). Combined organic layer was washed with water (5×100 mL), brine and dried over anhydrous sodium sulfate. Removal of solvent under reduced pressure afforded crude which was purified by Combi-Flash on silica gel using ethyl acetate-hexane system as eluent to afford 5-(((1s,4s)-4-(4-cyanophenoxy)cyclohexyl)oxy)picolinonitrile (220 mg, 83.3%).

Step 3

To a suspension of ammonium chloride (294.2 mg, 5.5 mmol, 8 eq.) in toluene (6 mL) was added trimethylaluminum (2M) (793.1 mg, 2.75 mL, 5.5 mmol, 8 eq.) dropwise at 0° C. The mixture was allowed to stir at the same temperature for 10 minutes followed by stirring at RT for 15 minutes. To this mixture was added 5-(((1s, 4s)-4-(4-cyanophenoxy)cyclohexyl)oxy)picolinonitrile (220 mg, 0.68 mmol, 1.0 eq.) and reaction mixture was allowed to stir at RT for another 15 minutes. The reaction mixture was then allowed to stir under reflux for 16 h. Reaction mixture was cooled to RT, diluted with methanol (5 mL) and allowed to stir at RT for 30 minutes. Reaction mixture was diluted with 1N aq. HCl (25 mL) and washed with ethyl acetate (50 mL). Aqueous layer was basified with 5N NaOH (20 mL) and extracted with a solution of 1:5 mixture of ethanol-ethyl acetate (3×50 mL). Combined organic layer was dried over anhydrous sodium sulfate. Removal of solvent afforded crude which was purified by reversed phase HPLC to afford 5-(((1s, 4s)-4-(4-carbamimidoylphenoxy)cyclohexyl)oxy) picolinimidamide as free base. Solid was dissolved in 1.25 M HCl in EtOH (5 mL) and the solution was concentrated under vacuum and lyophilized to afford 5-(((1s, 4s)-4-(4-carbamimidoylphenoxy)cyclohexyl)oxy)picolinimidamide dihydrochloride salt (5 mg, 4.95%).

Analytical Data

LCMS: 354 [M+1]$^+$ $^1$H NMR (400 MHz, DMSO-d6) δ11.33-10.49 (m, 6H), 8.48 (brs, 1H), 8.22 (brs, 1H), 7.81-7.74 (m, 3H), 7.19 (d, 2H), 2.00-1.75 (m, 8H).

Example 15

Preparation of 4-(5-(3-carbamimidoylphenoxy)pentyloxy)picolinimidamide

Compound 15

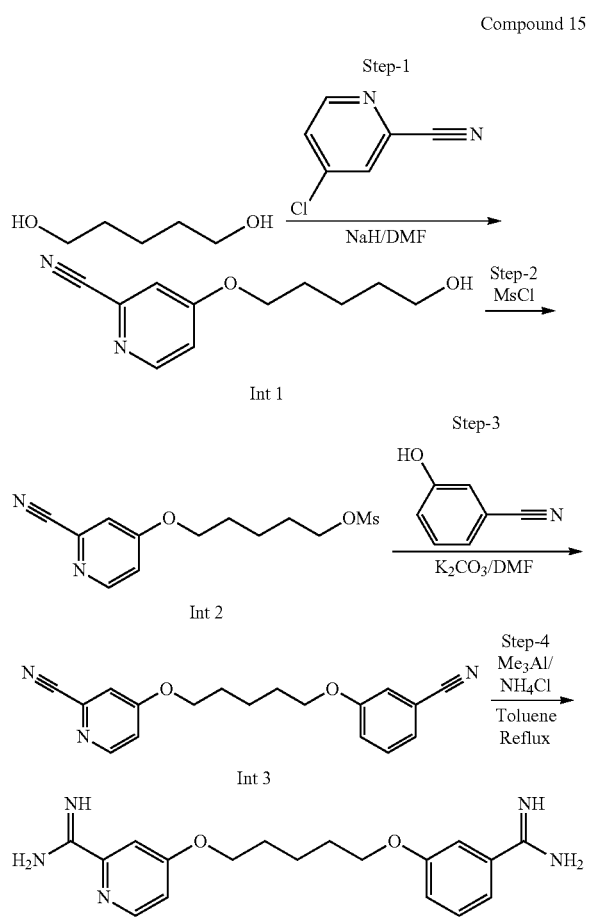

Step 1

To a stirred solution of 1,5-pentanediol (2.25 g, 2.16 mmol, 3.0 eq.) in dimethyl formamide (10 mL) were added sodium hydride (1.5 g, 1.08 mmol, 1.5 eq.) at 0° C. The reaction mixture was stirred at RT for 15 minutes. To this mixture was added 4-chloro-pyridine-2-carbonitrile (1.0 g, 7.20 mmol, 1.0 eq.) and the reaction mixture was stirred at RT for 15 h. Progress of reaction was monitored by TLC. After consumption of 4-chloropyridine-2-carbonitrile, reaction mixture was diluted with ethyl acetate (50 mL) and washed with water (3×20 mL). Organic layer was dried over sodium sulphate and concentrated under reduced pressure to get crude oil which was purified by Combi-Flash on silica gel using ethyl acetate-hexane system as eluent to afford 4-[(5-hydroxypentyl)oxy]pyridine-2-carbonitrile (600 mg, 40.54%).

Step 2

To a stirred solution of 4-(5-hydroxypentyloxy)picolinonitrile (0.450 g, 2.18 mmol, 1 eq.) in dichloromethane (5 mL) was added TEA (0.33 g, 3.27 mmol, 1.5 eq.) at 0° C. and the reaction mixture was stirred at 0° C. for 10 minutes. To this solution was then added methane sulfonyl chloride (0.299 g, 2.61 mmol, 1.2 eq.) at 0° C. The reaction mixture was stirred at RT for 60 minutes. Progress of reaction was monitored by TLC. After completion, the reaction mixture was diluted with water (50 mL) and extracted with dichloromethane (3×50 mL). Combined organic layer was dried over sodium sulfate and concentrated under vacuum to afford crude residue which was purified by Combi-Flash on silica gel using ethyl acetate-hexane system as eluent to afford 5-(2-cyanopyridin-4-yloxy)pentyl methanesulfonate (0.4 g, 68.4%).

Step 3

To a stirred solution of 5-(2-cyanopyridin-4-yloxy)pentyl methanesulfonate (0.4 g, 1.49 mmol, 1 eq.) in DMF (5 mL) was added $K_2CO_3$ (0.61 g, 4.47 mmol, 3 eq.) at RT and the reaction mixture was stirred at RT for 10 minutes. To this mixture was added 3-hydroxybenzonitrile (0.23 g, 1.93 mmol, 1.3 eq.) at RT and the reaction mixture was stirred at RT for 2 h. Progress of reaction was monitored by TLC. After completion, the reaction mixture was diluted with water (50 mL) and extracted with ethyl acetate (3×50 mL). Combined organic layer was dried over sodium sulfate and concentrated to dryness under vacuum to afford crude residue which was purified by Combi-Flash on silica gel using ethyl acetate-hexane system as eluent to afford 4-(5-(3-cyanophenoxy)pentyloxy)picolinonitrile (0.2 g, 43.67%).

Analytical Data

LCMS: 308 [M+1]$^+$

Step 4

To a stirred suspension of $NH_4Cl$ (0.348 g, 6.51 mmol, 10 eq.) in toluene (6 mL) at 0° C. was added trimethylaluminum (3.25 mL, 6.51 mmol, 10 eq.) dropwise under nitrogen and the reaction mixture was stirred at 0° C. for 10 minutes followed by stirring at RT for 15 minutes. To this mixture was added 4-(5-(3-cyanophenoxy)pentyloxy)picolinonitrile (0.2 g, 0.65 mmol, 1.0 eq.) was added at 0° C. and the reaction mixture was stirred at RT for 15 minutes. Then the reaction mixture was stirred at 120° C. for 18 h. The reaction mixture was cooled to RT, quenched by dropwise addition of methanol (5 mL) at 0° C. and then allowed to stir at RT for 30 minutes. The reaction mixture was acidified with 3M aq. HCl solution (50 mL) and extracted with ethyl acetate (20 mL). Organic layer was separated and aqueous layer was basified using 5N NaOH solution (50 mL) and extracted with 20% ethanol-ethyl acetate (3×200 mL). Combined organic layers were dried over sodium sulfate, filtered and evaporated to dryness. The residue was completely dried by toluene azeotrope. The residue was triturated with 50% ethanol-ethyl acetate mixture (2×50 mL) and the solid was removed by filtration. Filtrate was evaporated to afford crude material which was purified by reversed phase HPLC to afford the 4-(5-(3-carbamimidoylphenoxy)pentyloxy)picolinimidamide as a freebase. This solid was dissolved in 1.25 M HCl in ethanol (5 mL) at 0° C., ethanol was removed and residue was lyophilized to afford the dihydrochloride salt of 4-(5-(3-carbamimidoylphenoxy)pentyloxy)picolinimidamide (30 mg, 13.49%).

Analytical Data

LCMS: 342 [M+1]+

$^1$H NMR (400 MHz, DMSO-$d_6$) δ 9.65 (brs, 2H), 9.43 (s, 2H), 9.47 (s, 2H), 9.26 (brs, 2H), 8.60 (d, 1H), 8.06 (brs, 1H), 7.51 (m, 1H), 7.41 (m, 2H), 7.31 (m, 2H), 4.24 (t, 2H), 4.10 (m, 2H), 1.84 (d, 4H), 1.59 (brs, 2H).

Example 16

Preparation of 5,5'-(butane-1,4-diylbis(oxy))dipicolinimidamide

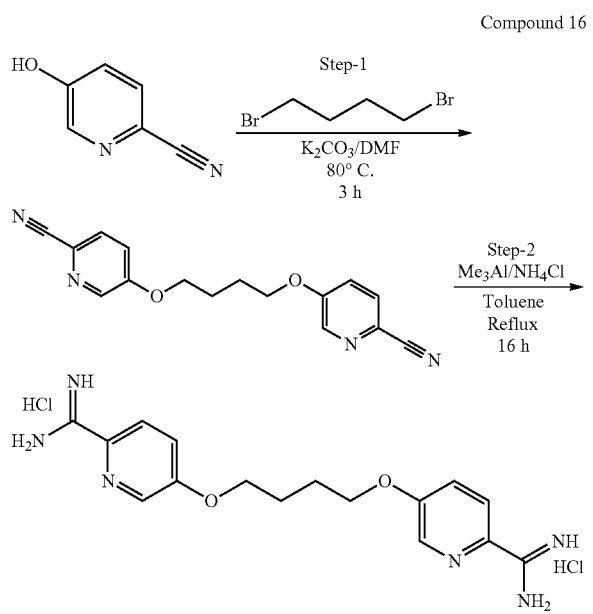

Compound 16

Step 1

To a solution of 1,4-dibromobutane (500 mg, 2.31 mmol, 1.0 eq.) in DMF (5 mL) was added $K_2CO_3$ (960 mg, 6.93 mmol, 3.0 eq.) and 5-hydroxypicolinonitrile (612.35 mg, 5.09 mmol, 2.2 eq.) at RT. The reaction mixture was then allowed to stir at 80° C. for 3 h. Progress of reaction was monitored by TLC. After completion, reaction mixture was diluted with ice cold water (50 mL) and extracted with ethyl acetate (3×200 mL). Combined organic layer was washed with water (5×50 mL) followed by 1N NaOH solution (3×30 mL) then brine (50 mL) and dried over anhydrous sodium sulfate. Removal of solvent under reduced pressure afforded crude material which was purified by Combi-Flash on silica gel using ethyl acetate-hexane system as eluent to afford 5,5'-(butane-1,4-diylbis(oxy))dipicolinonitrile (250 mg, 36.7%).

Step 2

To a suspension of ammonium chloride (334.5 mg, 6.25 mmol, 8.0 eq.) in toluene (10 mL) was added trimethylaluminum (2M) (901.5 mg, 3.13 mL, 6.25 mmol, 8.0 eq.) dropwise at 0° C. The mixture was allowed to stir at the same temperature for 10 minutes followed by stirring at RT for 15 minutes. To this mixture was added 5,5'-(butane-1,4-diylbis(oxy))dipicolinonitrile (230 mg, 0.78 mmol, 1.0 eq.) and reaction mixture was allowed to stir at RT for another 15 minutes. The reaction mixture was then allowed to stir under reflux for 16 h. Reaction mixture was cooled to RT, diluted with methanol (5 mL) and allowed to stir at RT for 30 minutes. Reaction mixture was diluted with 1N aq. HCl (20 mL) and washed with ethyl acetate (50 mL). Aqueous layer was basified with 5N NaOH (15 mL) and extracted with a solution of 1:5 mixture of ethanol-ethyl acetate (5×80 mL). Combined organic layer was dried over anhydrous sodium sulfate. Removal of solvent afforded crude material which was purified by reversed phase HPLC to afford 5,5'-(butane-1,4-diylbis(oxy))dipicolinimidamide as free base. The solid was dissolved in 1.25M HCl in EtOH (5 mL) and the solution was concentrated under vacuum and lyophilized to afford 5,5'-(butane-1,4-diylbis(oxy))dipicolinimidamide dihydrochloride (20 mg, 7.8%).

Analytical Data

LCMS: 329 [M+1]+

$^1$HNMR (400 MHz, DMSO-$d_6$) δ 9.40 (brs, 4H), 9.15 (brs, 1H), 8.49 (d, 2H), 8.30 (dd, 2H), 7.75 (dd, 2H), 4.26 (brs, 4H), 1.90 (brs, 4H).

Example 17

Preparation of 5-(3-(4-carbamimidoylphenoxy)propoxy)picolinimidamide

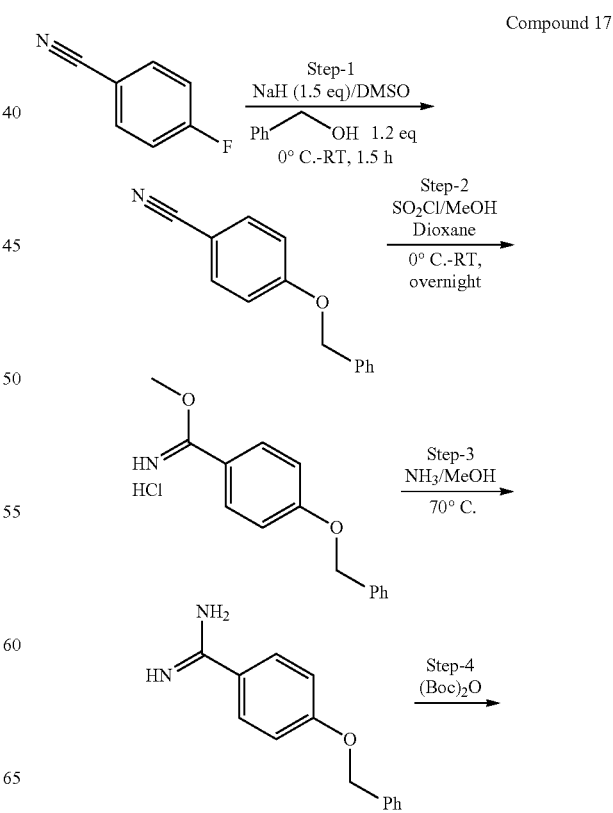

Compound 17

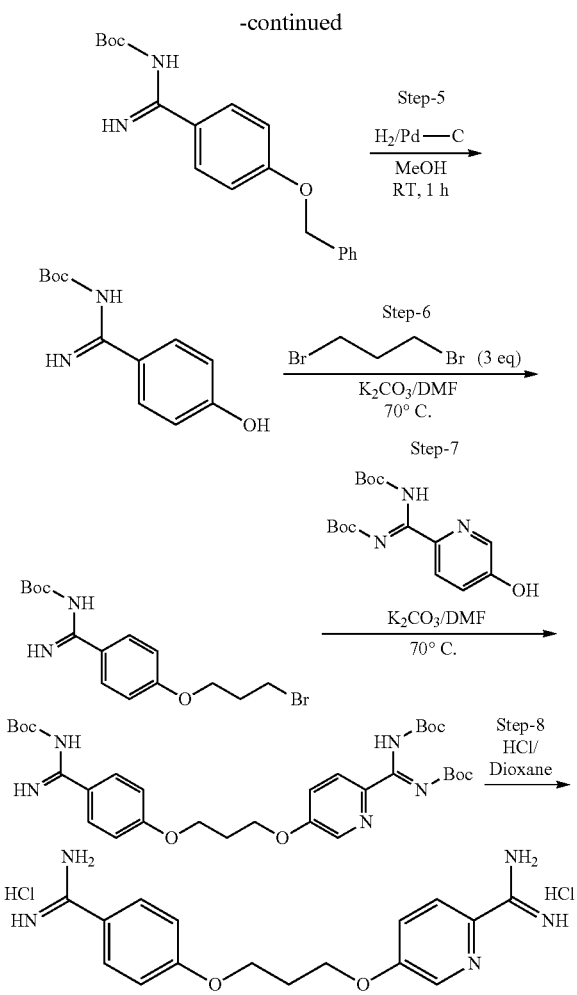

Step 1

To a stirred solution of benzyl alcohol (5.35 g, 49.5 mmol, 1.2 eq.) in DMSO (30 mL) at 0° C. was added sodium hydride (1.28 g, 53.5 mmol, 1.3 eq.) portion-wise and the resulting mixture was stirred at the same temperature for 15 minutes. To this mixture was added 4-fluorobenzonitrile (5 g, 41.2 mmol, 1 eq.) and then the reaction mixture was allowed to stir at room temperature for 2 h. Progress of reaction was monitored by TLC. After completion, reaction mixture was poured into water (200 mL) and the precipitate was filtered and dried under vacuum to afford 4-(benzyloxy) benzonitrile (6.97 g, 80%) which was used in the next step without further purification.

Step-2

To a stirred solution of 4-(benzyloxy)benzonitrile (6.9 g, 32.9 mmol, 1 eq.) in a solution of MeOH and dioxane (1:1, 80 mL) at 0° C. was added thionyl chloride (39.23 g, 329.7 mmol, 10 eq.) dropwise and the reaction mixture was allowed to stir at room temperature overnight. Progress of reaction was monitored by TLC. The reaction mixture was diluted with diethyl ether (500 mL) and stirred for 15 minutes. The precipitate was filtered and dried under vacuum to afford methyl 4-(benzyloxy)benzimidate hydrochloride (5 g, 62%) which was used in the next step without further purification.

Step 3

To a stirred solution of methyl 4-(benzyloxy)benzimidate hydrochloride (5 g, 20.7 mmol, 1 eq.) in methanol (100 mL) was added 7M ammonia in methanol (50 mL) and the reaction mixture was allowed to stir at 70° C. for 2 h. Progress of reaction was monitored by TLC. The methanol was then completely evaporated under reduced pressure to afford 4-(benzyloxy)benzimidamide (4.4 g, 94%) which was used in the next step without further purification.

Step 4

To a stirred solution of 4-(benzyloxy)benzimidamide (2 g, 8.8 mmol, 1 eq.) in THF (30 mL) was added a solution of sodium hydroxide (1.05 g, 26.5 mmol, 3 eq.) in water (10 mL) followed by Boc anhydride (5.78 g, 26.5 mmol, 3 eq.) and the reaction mixture was allowed to stir at room temperature for 1 h. Progress of reaction was monitored by TLC. After completion, reaction mixture was diluted with water (50 mL) and extracted using ethyl acetate (3×50 mL). Combined organic layer was washed with brine (20 mL), dried over anhydrous sodium sulfate and concentrated under vacuum to obtain crude material which was purified by Combi-Flash on silica gel using ethyl acetate-hexane system as eluent to afford tert-butyl (4-(benzyloxy)phenyl)(imino) methylcarbamate (1.5 g, 71%).

Step 5

To a stirred solution of tert-butyl (4-(benzyloxy)phenyl) (imino)methylcarbamate (1.5 g, 4.6 mmol, 1 eq.) in methanol (100 mL) was added Pd—C (300 mg) and the reaction mixture was allowed to stir under hydrogen atmosphere for 1 h. Progress of reaction was monitored by TLC. After completion, the reaction mixture was filtered through a celite bed and was washed with methanol (30 mL). The filtrate was concentrated under reduced pressure to afford tert-butyl (4-hydroxyphenyl)(imino)methylcarbamate (1.3 g, 86%) which was used in the next step without further purification.

Step 6

To a stirred solution of tert-butyl (4-hydroxyphenyl) (imino)methylcarbamate (0.500 g, 2.1 mmol, 1 eq.) and 1,3-dibromopropane (1.28 g, 6.3 mmol, 3 eq.) in acetone (15 mL) was added potassium carbonate (0.434 g, 3.1 mmol, 1.5 eq.) and the reaction mixture was allowed to stir at 60° C. for 2 h. Progress of reaction was monitored by TLC. After completion, the solid was removed by filtration and the filtrate was concentrated to afford an oily crude material which was purified by column chromatography on silica gel to afford tert-butyl (4-(3-bromopropoxy)phenyl)(imino) methylcarbamate (340 mg, 45%).

Step 7

To a stirred solution of (Z)-tert-butyl (5-hydroxypyridin-2-yl)methanediylidenedicarbamate (0.280 mg, 0.8 mmol, 1 eq.) and tert-butyl (4-(3-bromopropoxy)phenyl)(imino) methylcarbamate (325 mg, 0.9 mmol, 1.1 eq.) in DMF (10 mL) was added potassium carbonate (0.331 mg, 2.4 mmol, 3 eq.) and the reaction mixture was allowed to stir at 60° C. for 2 h. Progress of reaction was monitored by TLC. After completion, the reaction mixture was diluted with water (100 mL) and extracted with ethyl acetate (3×50 mL). Combined organic layer was washed with water (5×50 mL) followed by brine (20 mL) and dried over anhydrous sodium sulfate. Removal of solvent under reduced pressure gave crude material which was purified by Combi-Flash on silica gel to afford triboc-5-(3-(4-carbamimidoylphenoxy) propoxy)picolinimidamide (350 mg, 69%).

Step 8

A solution of triboc-5-(3-(4-carbamimidoylphenoxy) propoxy)picolinimidamide (0.350 mg, 0.5 mmol, 1 eq.) in 4M solution of HCl in dioxane was allowed to stir at room temperature for 5 h. Progress of reaction was monitored by $^1$H NMR. After completion, reaction mixture was triturated with ethyl acetate, filtrate was separate and dried under vacuum to afford 5-(3-(4-carbamimidoylphenoxy)propoxy)picolinimidamide dihydrochloride (152 mg, 85%).
Analytical Data
LCMS 313.15 [M+1]+
$^1$H NMR (400 MHz, DMSO-d$_6$) δ ppm 9.40 (brs., 2H) 9.15 (brs, 2H) 9.20 (brs, 2H) 8.91 (brs, 2H) 8.51 (d, 1H) 8.33 (d, 1H) 7.84 (d, 2H) 7.76 (dd, 1H) 7.18 (m, 2H) 4.37 (t, 2H) 4.28 (t, 2H) 2.24-2.31 (m, 2H).

Example 18

Preparation of 5-{2-[(1R,3S)-3-[2-(4-carbamimidoylphenyl)ethyl]cyclohexyl]ethyl}pyridine-2-carboximidamide

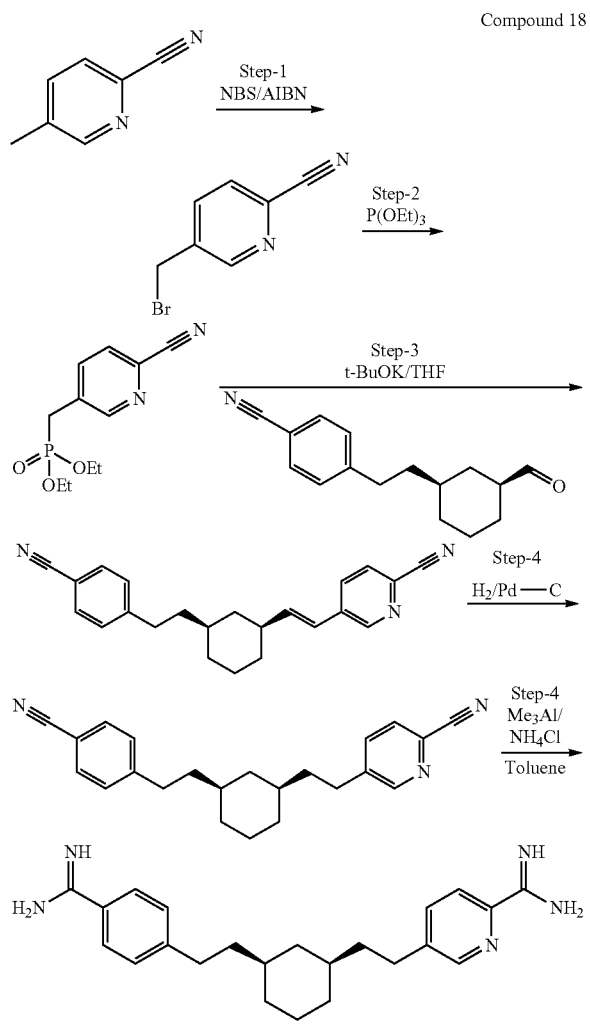

Step 1
To a solution of 5-methylpicolinonitrile (5 g, 42.30 mmol, 1.0 eq.) in CHCl$_3$ (80 mL) were added AIBN (3.47 g, 21.15 mmol, 0.5 eq.) followed by NBS (15.05 g, 84.60 mmol, 2.0 eq.) at RT and the mixture was allowed to stir at 50° C. for 3 h. Progress of reaction was monitored by TLC. After completion, reaction mixture was diluted with water (150 mL) and extracted with dichloromethane (3×300 mL). Combined organic layer was washed with brine and dried over anhydrous sodium sulfate. Removal of solvent under reduced pressure afforded crude which was purified by Combi-Flash on silica gel using ethyl acetate-hexane system as eluent to afford 5-(bromomethyl)picolinonitrile (2.5 g, 30%) as brown solid.

Step 2
A mixture of 5-(bromomethyl)picolinonitrile (2.5 g, 12.69 mmol, 1.0 eq.) and triethylphosphite (2.7 mL, 15.22 mmol, 1.2 eq.) was allowed to stir at 140° C. for 4 h. Progress of reaction was monitored by TLC. After completion, reaction mixture was diluted with ice cold water (150 mL) and extracted with ethyl acetate (3×200 mL). Combined organic layer was washed with brine (100 mL) and dried over anhydrous sodium sulfate. Removal of solvent under reduced pressure afforded crude which was purified by Combi-Flash on silica gel using ethyl acetate-hexane system as eluent to afford diethyl (6-cyanopyridin-3-yl)methylphosphonate (2.5 g, 83%) as viscous liquid.

Step 3
To a stirred solution of diethyl (6-cyanopyridin-3-yl)methylphosphonate (0.316 g, 1.24 mmol, 1.5 eq.) in THF (10 mL) at 0° C. was added 1M potassium tert-butoxide solution in THF (1.24 mL, 1.24 mmol, 1.5 eq.) dropwise and the reaction mixture was allowed to stir at the same temperature for 15 minutes. To this solution was added a solution of 4-(2-((1S,3S)-3-formylcyclohexyl)ethyl)benzonitrile (0.2 g, 0.828 mmol, 1 eq.) in THF (5 mL) and the reaction mixture was allowed to stir at RT for 45 minutes. Progress of reaction was monitored by TLC. After completion, the reaction mixture was diluted with aq. ammonium chloride solution (40 mL) and extracted with ethyl acetate (3×50 mL). Combined organic layer was washed with brine (20 mL), dried over anhydrous sodium sulfate and concentrated under reduced pressure to obtain crude material which was purified by Combi-Flash on silica gel using ethyl acetate-hexane system as eluent to afford 5-((E)-2-((1S,3S)-3-(4-cyanophenethyl)cyclohexyl)vinyl)picolinonitrile (0.180 g, 63.8%).

Step 4
To a solution of 5-((E)-2-((1S,3S)-3-(4-cyanophenethyl)cyclohexyl)vinyl)picolinonitrile (0.130 g, 0.380 mmol, 1 eq.) in methanol (20 mL) was added Pd—C (7 mg). The reaction mixture was allowed to stir at RT under hydrogen atmosphere for 25 minutes. Progress of reaction was monitored by TLC and $^1$H NMR. After completion, reaction mixture was filtered through a celite-bed and the bed was washed with methanol (20 mL). Filtrate was concentrated under reduced pressure to afford 5-(2-((1R,3S)-3-(4-cyanophenethyl)cyclohexyl)ethyl)picolinonitrile (100 mg) which was used in next step without further purification.

Step 5
To a suspension of NH$_4$Cl (161 mg, 3.02 mmol, 8 eq.) in toluene (5 mL) at 0° C. was added 2M trimethylaluminum in toluene (1.5 mL, 3.02 mmol, 8 eq.) dropwise and the mixture was allowed to stir at the same temperature for 15 minutes. The mixture was brought to RT and allowed to stir for an additional 10 minutes. To this mixture was added a solution of 5-(2-((1R,3S)-3-(4-cyanophenethyl)cyclohexyl) ethyl) picolinonitrile (130 mg, 0.378 mmol, 1 eq.) dissolved in toluene (5 mL) and the reaction mixture was allowed to stir at RT for more 10 minutes and then allowed to stir at 120° C. for 18 h. The reaction mixture was cooled to RT, diluted with methanol (5 mL) and allowed to stir at RT for 15 minutes. The reaction mixture was diluted with 3M aq. HCl (15 mL) and washed with ethyl acetate (30 mL). Aqueous layer was basified with 3M Aq. NaOH solution and extracted with 20% ethanol-ethyl acetate solution (3×50 mL). The combined organic layer was dried over sodium sulfate and concentrated under vacuum to afford crude material which was purified by reversed phase HPLC to afford desired product as free base. The solid was dissolved in 1.25 M HCl in ethanol (3 mL) and concentrated to obtain a solid which was lyophilized to afford desired compound as di-HCl salt (20 mg, 11.7
Analytical Data
LCMS: 378.3 [M+1]$^+$
$^1$H NMR (400 MHz, CD$_3$OD) δ 8.68 (d, 1H) 8.10 (d, 1H) 7.94 (dd, 1H) 7.73 (d, 2H) 7.45 (d, 2H) 2.85-2.70 (m, 4H) 1.95-1.75 (m, 4H), 1.70-1.50 (m, 4H), 1.40-1.20 (m, 4H) 1.00-0.77 (m, 2H).

Example 19

Preparation of 4-{[5-(4-carbamimidoylphenoxy) pentyl]oxy}pyridine-2-carboximidamide Compound 19

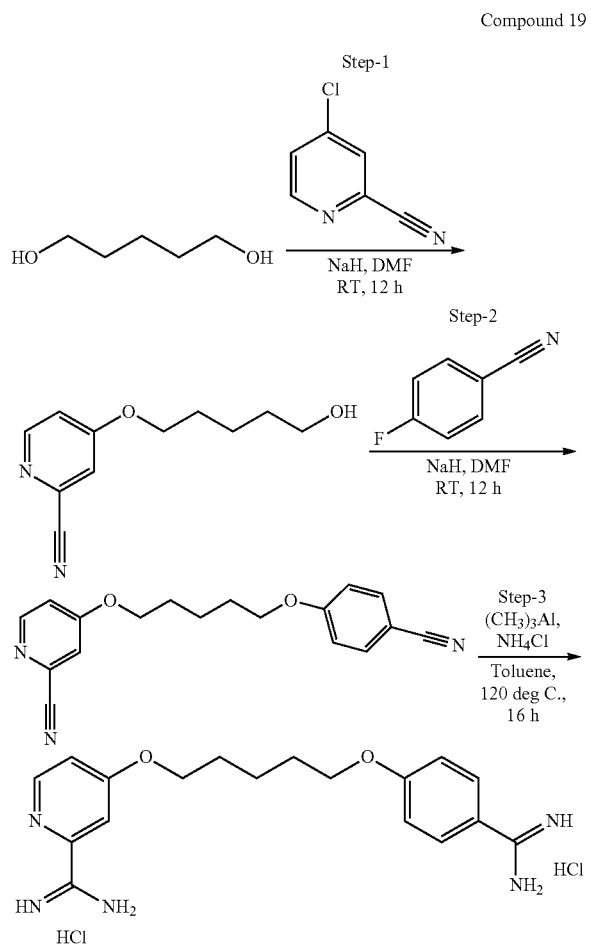

Step 1

To a stirred solution of pentane-1,5-diol (4.5 g, 43.47 mmol, 3.0 eq.) in DMF (15 mL) at 0° C. was added NaH (360 mg, 21.6 mmol, 1.5 eq.) and the resulting mixture was stirred at 0° C. for 15 minutes. To this mixture was added 4-chloropyridine-2-carbonitrile (2 g, 14.4 mmol, 1.0 eq.) and the reaction mixture was allowed to stir at RT for 12 h. Progress of reaction was monitored by TLC. After consumption of 4-chloropyridine-2-carbonitrile, reaction mixture was diluted with ethyl acetate (100 mL) and washed with water (3×50 mL). Combined organic layer was dried over sodium sulphate and concentrated under reduced pressure to afford crude oil which was purified by Combi-Flash on silica gel using ethyl acetate-hexane system as eluent to afford 4-[(5-hydroxypentyl)oxy]pyridine-2-carbonitrile (1 g, 34.38%).
Analytical Data:
LCMS: 206 ([M+1])$^+$
Step 2
To a stirred solution of 4-[(5-hydroxypentyl)oxy]pyridine-2-carbonitrile (500 mg, 2.42 mmol, 1.0 eq.) in DMF (10 mL) at 0° C. was added NaH (291 mg, 7.27 mmol, 1.5 eq.) and the resulting mixture was stirred at 0° C. for 15 minutes. To this mixture was added 4-flurobenzonitrile (588 mg, 4.85 mmol, 2.0 eq.) and the reaction mixture was allowed to stir at RT for 12 h. Progress of reaction was monitored by TLC. After consumption of 4-[(5-hydroxy-pentyl)oxy]pyridine-2-carbonitrile, reaction mixture was diluted with ethyl acetate (100 mL) and washed with water (3×20 mL). Organic layer was dried over sodium sulphate. Removal of ethyl acetate under reduced pressure gave crude oil which was purified by Combi-Flash on silica gel using ethyl acetate-hexane system as eluent to afford 4-{[5-(4-cyanophenoxy)pentyl]oxy}pyridine-2-carbonitrile (300 mg, 40.26%).
Step 3
To a stirred suspension of NH$_4$Cl (418 mg, 7.81 mmol, 8 eq.) in toluene (10 mL) at 0° C. was added trimethylaluminum (4.0 mL, 7.81 mmol, 8 eq.) dropwise under nitrogen. The reaction mixture was stirred at 0° C. for 10 minutes followed by stirring at RT for 15 minutes. The reaction mixture was cooled to 0° C. and 4-{[5-(4-cyanophenoxy)pentyl]oxy}pyridine-2-carbonitrile (300 mg, 0.97 mmol, 1 eq.) was added. The reaction mixture was stirred at room temperature (RT) for 15 minutes followed by stirring at 120° C. for 16 h. The reaction mixture was cooled to 0° C. and methanol (5 mL) was added dropwise and allowed to stir at RT for 30 minutes. The reaction mixture was acidified with 2M HCl solution (150 mL) and extracted with ethyl acetate (50 mL). Organic layer was separated and aqueous layer was basified with 5N NaOH solution (50 mL) and extracted with 20% ethanol-ethyl acetate (5×200 mL). Combined organic layer was dried over sodium sulphate, filtered and evaporated to dryness. Traces of water were removed by toluene azeotrope to get solid residue. Solid was triturated with 1:1 ethanol-ethyl acetate (2×200 mL) and filtered. Filtrate was evaporated to dryness and then the residue was purified by reversed phase HPLC to afford 4-{[5-(4-carbamimidoylphenoxy)pentyl]oxy}pyridine-2-carboximidamide as a free base. This solid was dissolved in 1.25 M HCl in ethanol (5 mL) at 0° C. and the material was evaporated to dryness and then lyophilized to afford 4-{[5-(4-carbamimidoylphenoxy) pentyl]oxy}pyridine-2-carboximidamide as hydrochloride salt (10 mg, 2.5%).
Analytical Data
LCMS: 342 [M+1]$^+$
$^1$H NMR (400 MHz, DMSO-d$_6$) δ 9.58 (brs, 2H), 9.38 (brs, 2H), 9.21 (brs, 2H), 8.95 (brs, 2H), 8.60 (d, 1H), 7.99 (s, 1H), 7.84 (d, 2H), 7.34 (d, 1H), 7.15 (d, 2H), 4.23 (t, 2H), 4.12 (t, 2H), 1.90-1.70 (m, 4H), 1.65-1.50 (m, 2H).

Example 20. Cytotoxicity of Pyridinyl Analog Compounds

The objective of this study is to investigate potential cell killing effect of Compounds 1-15 on 3 cancer cell lines. 50% inhibition concentration ($IC_{50}$) was determined for these compounds in various cancer cell lines using CellTiter-Glo™ luminescent cell viability assay at different compound concentrations. Each cell line (e.g., NCI-H209; NCI-H69; and SW1271) was treated with Compounds 1-15 and culture medium contains 0.2% [v/v] DMSO vehicle control. All the cells were cultured in the media supplemented with 10-20% fetal bovine serum at 37° C., 5% $CO_2$ and 95% humidity. $IC_{50}$ of values against NCI-H209; NCI-H69; and SW1271 cell lines are shown in Table 2 below.

TABLE 2

$IC_{50}$ of Compounds 1 through 15

| Compound No. | $IC_{50}$ (uM) [NCI-H209] | $IC_{50}$ (uM) [NCI-H69] | $IC_{50}$ (uM) [SW1271] |
| --- | --- | --- | --- |
| 1 | 1.7 | 0.858 | N/A |
| 2 | 9.38 | 3.48 | 1.6 |
| 3 | 3.47 | 2.91 | 3.47 |
| 5 | 2.78 | 0.876 | N/A |
| 6 | 3.48 | 1.07 | 0.455 |
| 7 | N/A | 0.804 | N/A |
| 8 | N/A | 0.687 | N/A |
| 9 | N/A | 5.28 | N/A |
| 10 | N/A | 22.2 | N/A |
| 11 | N/A | 0.62 | N/A |
| 12 | N/A | 1.58 | N/A |
| 13 | N/A | 2.11 | N/A |
| 14 | N/A | 1.1 | N/A |
| 15 | N/A | 0.49 | N/A |

*N/A, not determined

Example 21. Cytotoxicity of Pyridinyl Compounds

The objective of this study is to investigate the effect of Compound 1 on cytotoxicity against 61 different types of cancer cell lines. $IC_{50}$ were values were obtained using CellTiter-Glo™ as described above. Each cell line shown in Table 3 was treated with Compound 1, a standard chemotherapy drug, cisplatin, as reference control and culture medium contains 0.2% [v/v] DMSO vehicle control. All cancer cell lines were cultured in media supplemented with 10-20% fetal bovine serum at 37° C., 5% $CO_2$ and 95% humidity. Table 3 shows $IC_{50}$ values of Compound 1 against various types of liver cancer, cholangiocarcinoma, gallbladder cancer, renal cancer, prostate cancer, lung cancer, brain cancer, ovarian cancer, gastric cancer, colon cancer, and bone cancer.

TABLE 3

Cytotoxicity of Compound 1 ($IC_{50}$)

| Cell Line Name | Type | $IC_{50}$ (uM) |
| --- | --- | --- |
| HCCC-9810 | Intrahepatic cholangiocarcinoma | 0.71 |
| HCCLM3 | Hepatocellular carcinoma | 12.16 |
| Hep G2 | Hepatoblastoma carcinoma | 0.34 |
| Hep G2/C3A | Hepatoblastoma carcinoma | 0.23 |
| Hep3B | Hepatocellular carcinoma | 0.28 |
| HLE | Hepatocellular carcinoma | 0.59 |
| HLF | Hepatocellular carcinoma | 2.04 |
| HuCCT1 | Intrahepatic cholangiocarcinoma | 8.01 |
| HUH-1 | Hepatocellular carcinoma | 3.2 |
| HUH-6 CLONE5 | Hepatoblastoma carcinoma | 0.86 |
| HUH-7 | Hepatocellular carcinoma | 0.97 |
| JHH-1 | Hepatocellular carcinoma | 3.87 |
| JHH-4 | Hepatocellular carcinoma | 1.27 |
| JHH-5 | Hepatocellular carcinoma | 0.65 |
| JHH-6 | Hepatocellular carcinoma | 0.38 |
| JHH-7 | Hepatocellular carcinoma | 0.5 |
| Li-7 | Hepatocellular carcinoma | 0.76 |
| MHCC97-H | Hepatocellular carcinoma | 8.31 |
| NOZ | Gallbladder carcinoma | 2.54 |
| OCUG-1 | Gallbladder carcinoma | 2.89 |
| OZ | Intrahepatic cholangiocarcinoma | 9.39 |
| PLC/PRF/5 | Hepatocellular carcinoma | 4.13 |
| RBE | Intrahepatic cholangiocarcinoma | 1.4 |
| SK-HEP-1 | Hepatocellular carcinoma | 4.72 |
| SNU-354 | Hepatocellular carcinoma | 0.84 |
| SNU-368 | Hepatocellular carcinoma | 0.36 |
| SNU-387 | Hepatocellular carcinoma | 4 |
| SNU-398 | Hepatocellular carcinoma | 0.22 |
| SNU-423 | Hepatocellular carcinoma | 1.75 |
| SNU-449 | Hepatocellular carcinoma | 1.57 |
| SNU-475 | Hepatocellular carcinoma | 1.25 |
| SNU-739 | Hepatocellular carcinoma | 2.23 |
| SNU-761 | Hepatocellular carcinoma | 3.31 |
| 786-O | Renal cell carcinoma | 9.63 |
| 769-P | Renal cell carcinoma | 1.63 |
| A498 | Renal cell carcinoma | 1.17 |
| ACHN | Papillary renal cell carcinoma | 4.64 |
| Caki-2 | Papillary renal cell carcinoma | 4.18 |
| OS-RC-2 | Renal cell carcinoma | 1.7 |
| SK-NEP-1 | Ewing sarcoma | 1.93 |
| SW 156 | Renal cell carcinoma | 6.28 |
| UO.31 | Renal cell carcinoma | 3.47 |
| Caki-1 | Clear cell renal cell carcinoma | 3.42 |
| LNCaP clone FGC | Prostate carcinoma | 1.78 |
| OVCAR-3 | High grade ovarian serous adenocarcinoma | 1.96 |
| SK-OV-3 | Ovarian serous cystadenocarcinoma | 1.17 |
| A549 | Lung adenocarcinoma | 0.37 |
| NCI-H460 | Large cell lung carcinoma | 0.52 |
| NCI-H1975 | Lung adenocarcinoma | 2.66 |
| LN-229 | Glioblastoma | 1.6 |
| SF268 | Astrocytoma | 0.75 |
| U-87 MG | Glioblastoma | 5.58 |
| MKN45 | Gastric adenocarcinoma | 0.64 |
| DLD-1 | Colon adenocarcinoma | 3.11 |
| HCT 116 | Colon carcinoma | 2.67 |
| BT-474 | Invasive ductal carcinoma | 15.68 |
| DU4475 | Breast carcinoma | 0.24 |
| HCC1954 | Ductal breast carcinoma | 2.71 |
| MCF7 | Invasive ductal carcinoma | 0.93 |
| ZR-75-1 | Invasive ductal carcinoma | 1.32 |
| Saos-2 | Osteosarcoma | 2.39 |

Liver Cell Lines

The objective of this study is to investigate the effect of Compound 1 on cell viability of various types of liver cancer. Ten (10) different liver cancer cell lines were employed in the study. Each liver cell line shown in Table 4 was treated with Compound 1, pentamidine, as reference control, a stand of care (cisplatin) and culture medium contains 0.2% [v/v] DMSO vehicle control and $IC_{50}$ values were obtained as described above. The raw data values from the CellTiter-Glo™ cell viability assay expressed in relative luminescence units were normalized to the vehicle for each individual plate, and any reduction in luminescence indicated a decrease in viability (%). The data was analyzed in GraphPad PRISM using a non-linear sigmoidal plot with variable slope (asymmetric four-point linear regression), and an $IC_{50}$ value for each compound was generated. The experiment tested pentamidine, compound 1, and standard-of-care control Cisplatin in full growth media for 8 days. Cells were initially treated with the test compounds on Day 0, and the cells were then replenished with fresh compound dilutions on Day 3. Pentamidine, Compound 1, and cisplatin were tested at 9 concentration points; 100, 33.33, 11.11, 3.70, 1.23, 0.41, 0.14, 0.05, and 0.02 µM (final DMSO concentration=0.5%). One independent experiment was performed and IC$_{50}$ values are summarized in Table 4 below. In particular, the IC$_{50}$ values of pentamidine and Compound 1 were 0.8 and 0.6 µM in Hep3B-luc, respectively. The IC$_{50}$ value for cisplatin was 5.1 µM was consistent with historical data.

TABLE 4

IC$_{50}$ of Liver Cell Lines

| Cell Line Name | Pentamidine (IC$_{50}$) | Compound 1 (IC$_{50}$) |
| --- | --- | --- |
| Hep3B-luc (IC50 uM) | 0.8 | 0.6 |
| HCCLM3 (IC50 uM) | 6.9 | 9.65 |
| Hep3B (IC50 uM) | 0.16 | 0.18 |
| HepG2 (IC50 uM) | 0.29 | 0.31 |
| HUH1 (IC50 uM) | 1.79 | 2.95 |
| HUH7 (IC50 uM) | 0.68 | 0.53 |
| MHCC97H (IC50 uM) | 4.26 | 5.32 |
| SK-HEP-1 (IC50 uM) | 1.45 | 1.4 |
| HEP3B2.7-1 (IC50 uM) | 0.28 | 0.32 |
| SK-HEP-1 (IC50 uM) | 0.72 | 0.63 |

Furthermore, IC$_{50}$ of Compounds 4, 5, and 19 also were also assessed in a similar experiment and demonstrated potent cytotoxicity against liver cell lines as shown in Table 5.

TABLE 5

IC$_{50}$ of Compounds 4, 5, and 19

| Cell Line Name | Cmpd 4 (IC$_{50}$ uM) | Cmpd 5 (IC$_{50}$ uM) | Cmpd 19 (IC$_{50}$ uM) |
| --- | --- | --- | --- |
| HEP3B2.7-1 (IC50 uM) | 1.91 | 0.207 | 0.222 |
| SK-HEP-1 (IC50 uM) | 5.95 | 0.73 | 0.84 |

TABLE 6

Compounds 20 and 21

Figure 2:
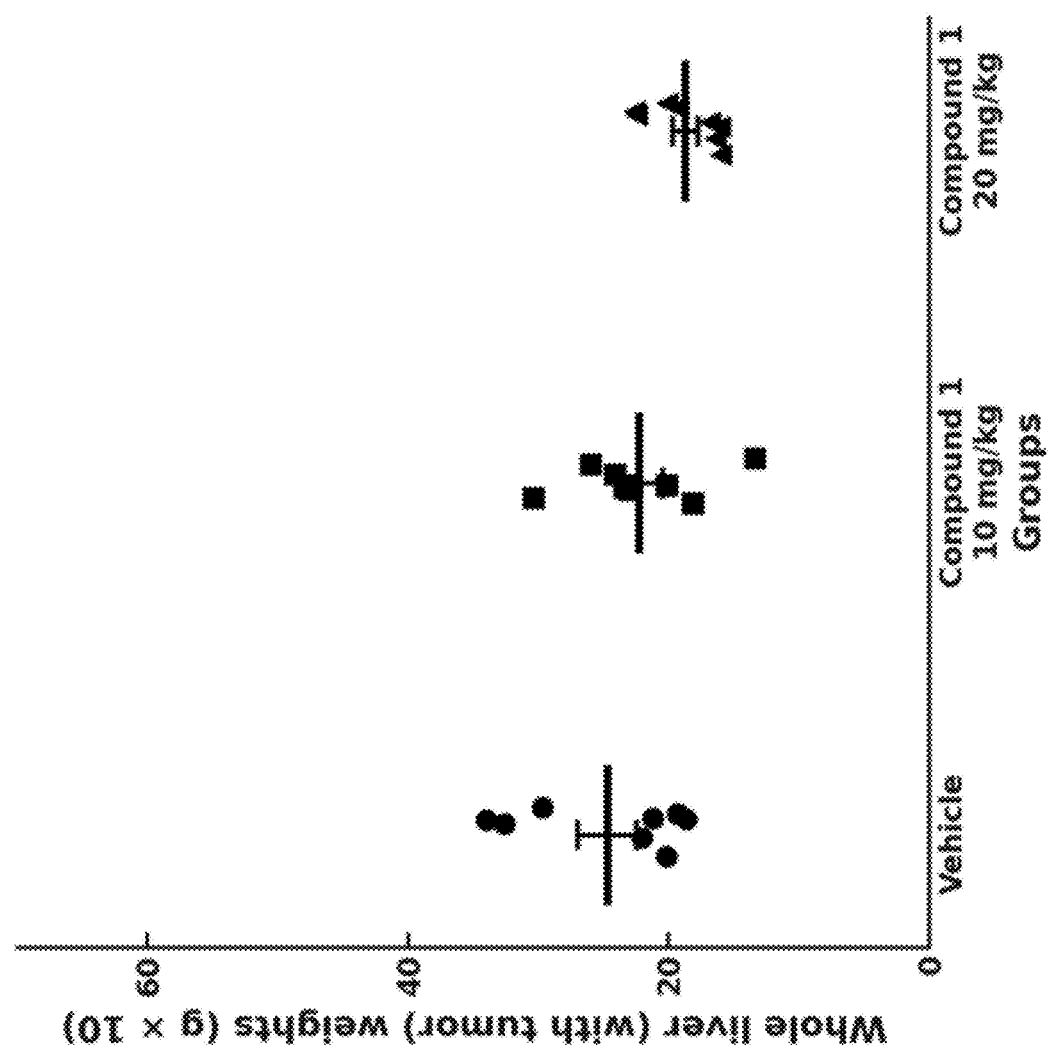
FIG. 2 depicts whole liver weights of mice treated with Compound 1 at 10 mg per kg and 20 mg per kg compared with vehicle.
Figure 3:
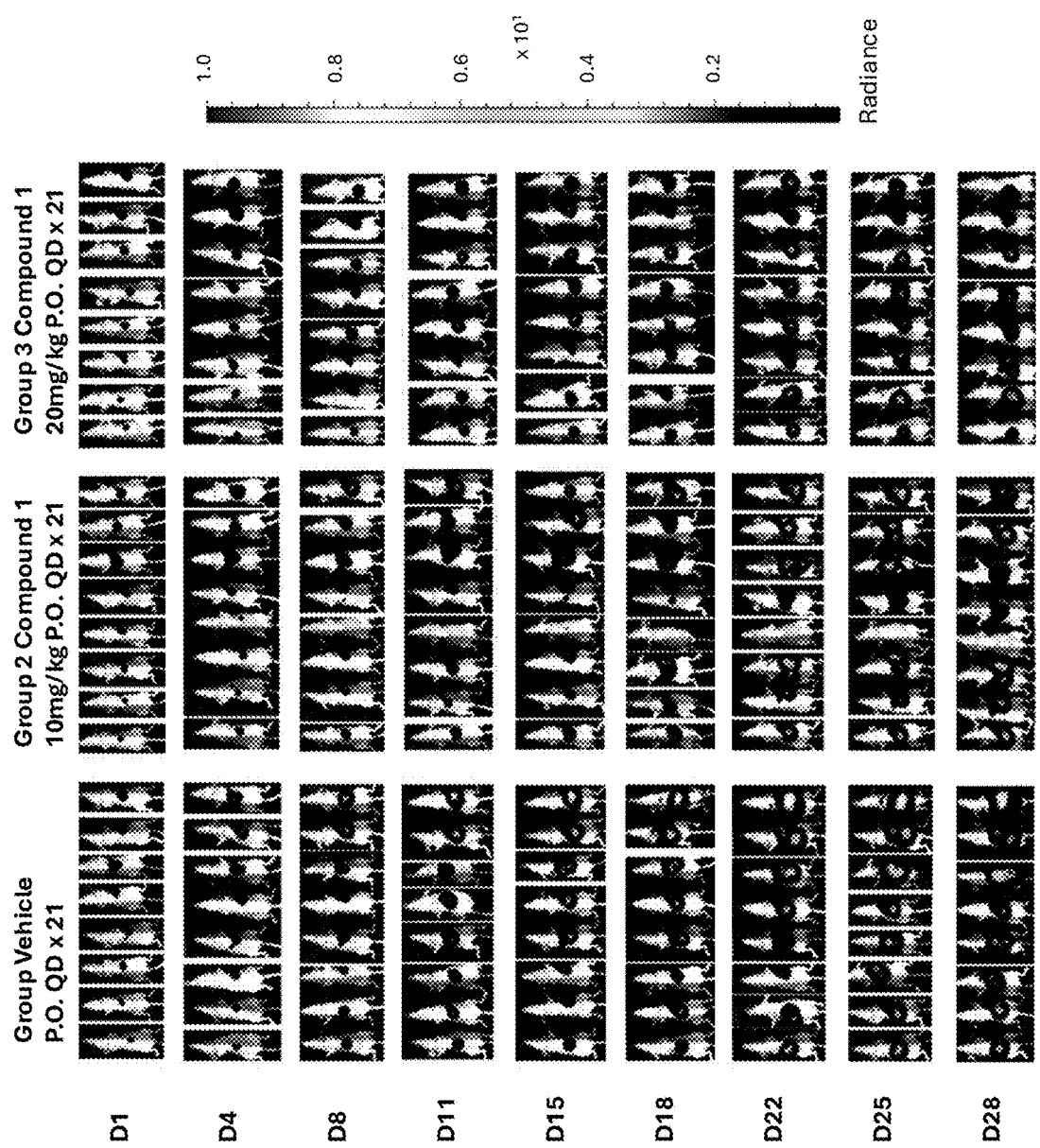
FIG. 3 depicts images of mice carrying liver cancer cell line treated with Compound 1.

| Cmpd No. | Structure | Name | Human Microsomal CL Rate (uL/min/mg) |
| --- | --- | --- | --- |
| 20 | [structure] | 5-({5-[(6-carbamimidoylpyridin-3-yl)oxy]pentyl}oxy)pyridine-2-carboximidamide | 4 |
| 21 | [structure] | 4-({5-[2-carbamimidoylpyridin-4-yl)oxy]pentyl}oxy)pyridine-2-carboximidamide | 5.1 | photons/s/10$^6$ in three groups are shown in FIG. 1. The mean Total Flux (photons/s/10$^6$) of the mice in vehicle control group reached 1223.01 photons/s/10$^6$ at day 28 post grouping. The mean Total Flux (photons/s/10$^6$) was 464.74 and 306.74 for Compound 1 (10 mg/kg) group and Compound 1 (20 mg/kg) group at day 28 post grouping. Compared to vehicle group, Compound 1 (10 mg/kg) group showed significant anti-tumor effect at day 8 to day 18 and day 28; Compound 1 (20 mg/kg) group showed significant anti-tumor effect at day 8 to day 28 (FIG. 1). Compound 1 was well tolerated in both 10 mg/kg and 20 mg/kg groups with no obvious body weight loss. Both Compound 1 groups steadily gained body weight until day 28, whereas the mice in the vehicle treated group exhibited weight loss at day 28. The whole liver (with tumor) weights are shown in Table 7 and FIG. 2.

TABLE 7

Mice whole liver (with tumor) weights in different treatment groups

| | Whole liver (with tumor) weights (g) | | |
| --- | --- | --- | --- |
| Animal no. | Vehicle | Compound 1 10 mg/kg | Compound 1 20 mg/kg |
| 1 | 1.866 | 1.817 | 1.610 |
| 2 | 2.206 | 2.019 | 1.603 |
| 3 | 1.933 | 2.311 | 2.260 |
| 4 | 3.258 | 1.334 | 1.681 |
| 5 | 2.015 | 2.415 | 2.243 |
| 6 | 2.966 | 2.602 | 1.645 |
| 7 | 3.397 | 2.280 | 2.012 |
| 8 | 2.123 | 3.035 | 1.926 |

Tumor sizes (indicated by signal intensity) in Compound 1 (10 mg/kg) group showed significant difference at day 25 and extremely significant difference at day 28; and tumor sizes in Compound 1 (20 mg/kg) showed extremely significant difference at day 22 to day 28, compared with that in vehicle control group as based on two-way ANOVA and Bonferroni post-test.

Tumor sizes in Compound 1 (10 mg/kg) group showed no significant difference during the treatment days; and tumor sizes in Compound 1 (20 mg/kg) showed significant difference at day 28 and extremely significant difference at day Example 22. Liver Orthotopic In Vivo Analysis In this study, the in vivo therapeutic effect of Compound 1 on liver cancer was evaluated in an orthotopic mouse model using Hep3B2.1-7-Luc cell line. Three groups of orthotopic model in BALB/c nude mice were treated with vehicle, Compound 1 at 10 mg/kg, and Compound 1 at 20 mg/kg orally (p.o.) Q3D for a week followed by QD for three weeks. Results of Total Flux as measured in unit of 25, compared with that in vehicle control group based on statistical analyses using nonparametric ANOVA followed by Kruskal-Wallis test.

Figure 4:
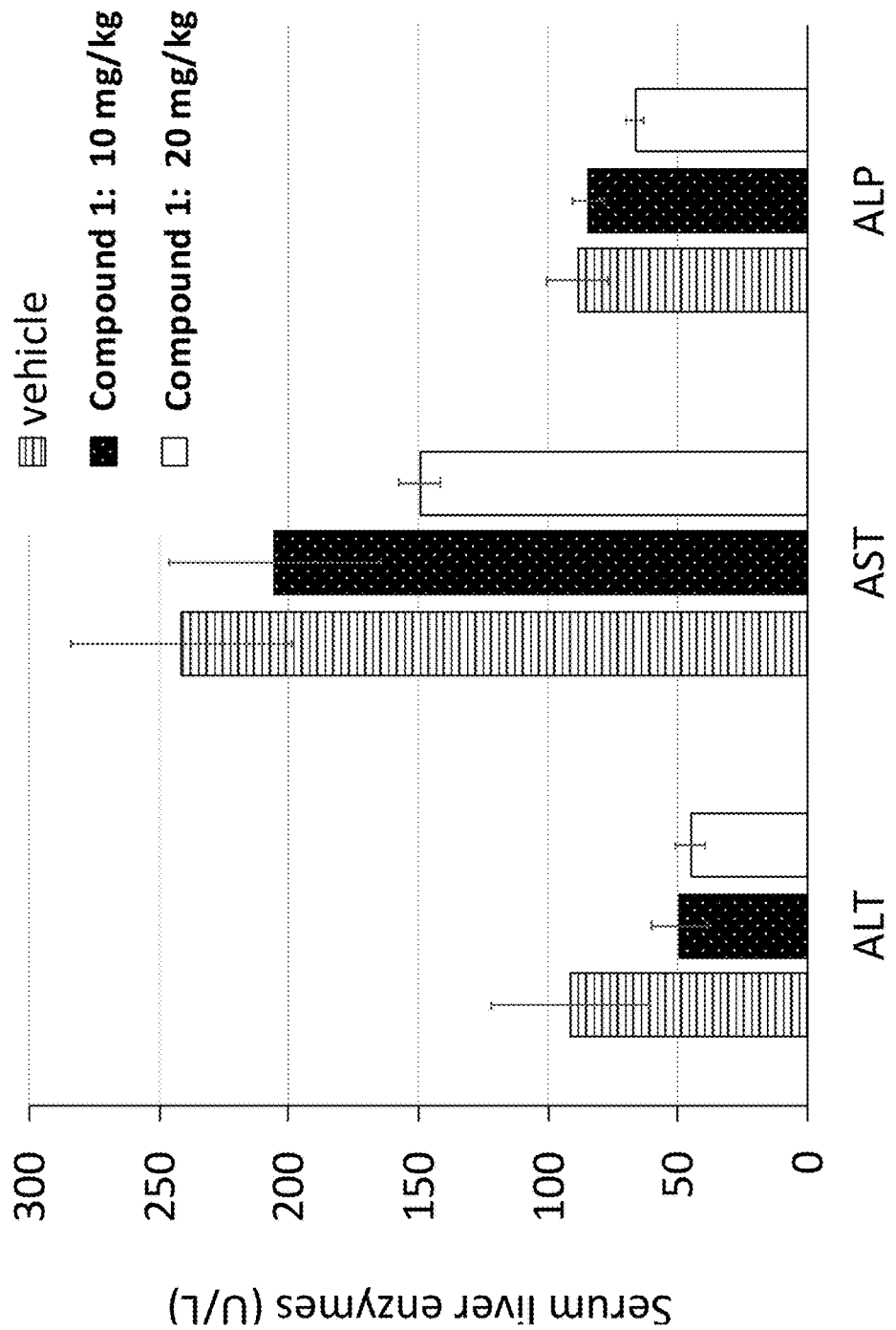
FIG. 4 depicts in vivo effects of Compound 1 on liver transaminases levels (ALT, AST, and ALP).

A One-way ANOVA combined with Dunnett post-test was performed to compare the results of serum-derived blood chemistries (including ALT, AST, ALP, TP, ALB, UA, UREA, Glu, TC, TG, Ca, Mg, P, CK, LDH, GLB, A/G and CREA) among vehicle and treatment groups. A nonparametric ANOVA followed by Kruskal-Wallis test was performed to compare serum-derived blood chemistries (including ALT, AST and ALP) among vehicle and treatment groups. Both treated groups (10 mg/kg and 20 mg/kg) showed significant reduction in levels of liver injury/damage markers, i.e., ALT and AST, in a dose dependent manner, suggesting that the treatment with Compound 1 enhanced liver function by reducing the liver tumor burden (FIG. 4).

To summarize, Compound 1 was well tolerated at both doses level tested. Further, Compound 1 dosed at 20 mg/kg showed significant in vivo anti-tumor activity against the Hep3B2.1-7-Luc liver orthotopic model in BALB/c nude mice at day 25 and day 28 (FIGS. 1-4).

Example 23. Tolerance of Compound 1 in BALB/c Nude Mice

The objective of this research is to assess Compound 1 tolerance in non-tumor bearing mice in BALB/c nude mice. Compound 1 exposure in plasma, liver, kidney, colon and bladder as well as serum-derived blood chemistries were tested.

Materials

Thirty-six (36) female BALB/c nude mice of age 6-8 weeks having body weight of around 19-23 g were kept in individual ventilation cages at constant temperature (20-26° C.) and humidity (40-70%) with 3 animals per cage. Animals had free access to irradiation sterilized dry granule food and sterile drinking water during the entire study period. Details of the study design are shown in Table 8.

TABLE 8

Experimental Design

| Group | treatment | N* | Dose level (mg/kg) | Dose Route | Dose schedule |
|---|---|---|---|---|---|
| 1 | Vehicle | 6 | — | PO | QD*21 |
| 2 | Compound 1 | 6 | 5 | PO | QD*21 |
| 3 | Compound 1 | 6 | 10 | PO | QD*21 |
| 4 | Compound 1 | 6 | 10 | PO | Q2D*21 |
| 5 | Compound 1 | 6 | 20 | PO | QD*21 |
| 6 | Compound 1 | 6 | 40 | PO | QD*21 |

Note:
N*: animal number; PO, per os (oral administration, p.o.)

After grouping, the animals were checked daily for morbidity and mortality. At the time of routine monitoring, the animals were measured for any effects on behavior such as mobility, food and water consumption, body weight gain/loss. Body weights were measured daily. Death and other clinical signs were recorded.

Animals from each group were tested and samples collected at two different time points for blood chemistry tests as well as compound concentration in plasma, kidney, liver, colon and bladder. The first sampling was performed right before the last dose (0 h) on Day 21; and the second sampling was performed 1 hour after the last dose (1 h) on day 21. Detailed descriptions for sampling methods are as follows:

Serum Collection: Collected about 500 uL of blood into 1.5 mL tube. All samples were put in room temperature for 30 minutes before centrifugation, then blood was centrifuged at 6,000 rpm, 4° C. for 5 minutes to get serum. Serum samples were transferred to −80° C. freezers for storage for blood routine test.

Plasma Collection: Collected about 200 uL blood into 1.5 mL tube containing anti-coagulant—2K-EDTA for plasma. Plasma was transferred to −80° C. freezers for storage for exposure analysis.

Kidney Collection: Left kidney in each mouse was collected, weighed and snapped frozen in dry ice and then transferred to −80° C. freezers for storage for exposure analysis. Right kidney was fixed in neutral formalin for 24 hours then 70% EtOH, for paraffin embedding and H&E stain and image analysis.

Liver Collection: Left liver lobe in each mouse was collected and divided in two. One part was weighed and snapped frozen in dry ice and then transferred to −80° C. freezers for storage for subsequent exposure analysis. The other part was fixed in neutral formalin for 24 hours then 70% EtOH, for paraffin embedding and H&E stain and image analysis.

Colon Collection: Collected the whole colon and then manually perfused the whole colon with cold PBS solution to remove fecal material. Finally, transversely opened the colon, and gently blotted it. The whole colon in each mouse was collected, weighed and snapped frozen in dry ice and then transferred to −80° C. freezers for storage. The whole colon from group 5 (compound 1, 20 mg/kg, p.o. QD*21 group) were stored for exposure analysis.

Bladder Collection: Bladder in each mouse was collected, weighed and snapped frozen in dry ice and then transferred to −80° C. freezers for storage. The bladder from group 5 (compound 1, 20 mg/kg, p.o. QD*21 group) was stored for bioassay analysis for exposure analysis. TBD for others.

Results

Figure 5:
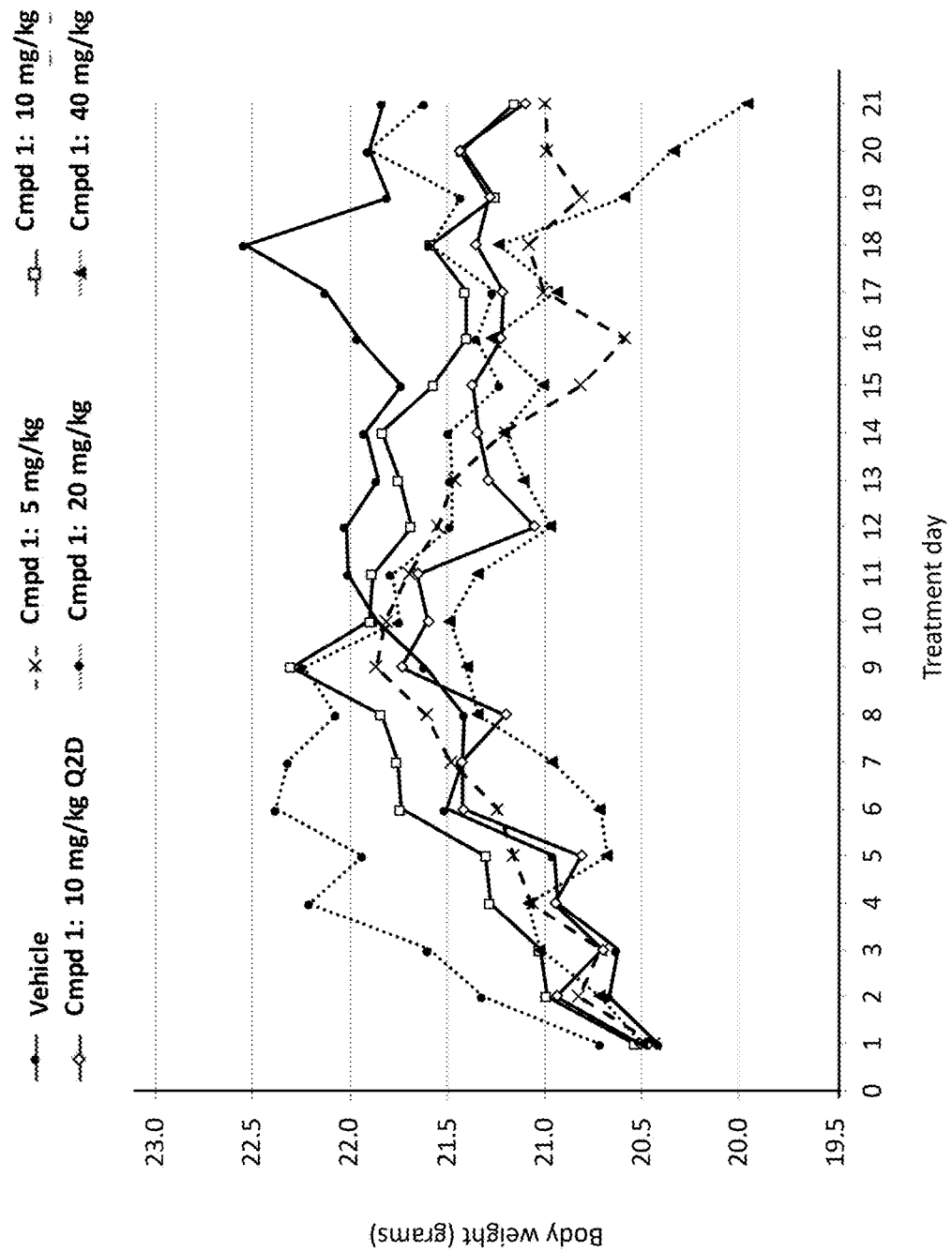
FIG. 5, depicts body weights changes in BALB/c nude mice treated with Compound 1 at 5 mpk, 10 mpk, 10 mpk Q2D, 20 mpk, and 40 mpk dosed orally (PO).
Figure 6:
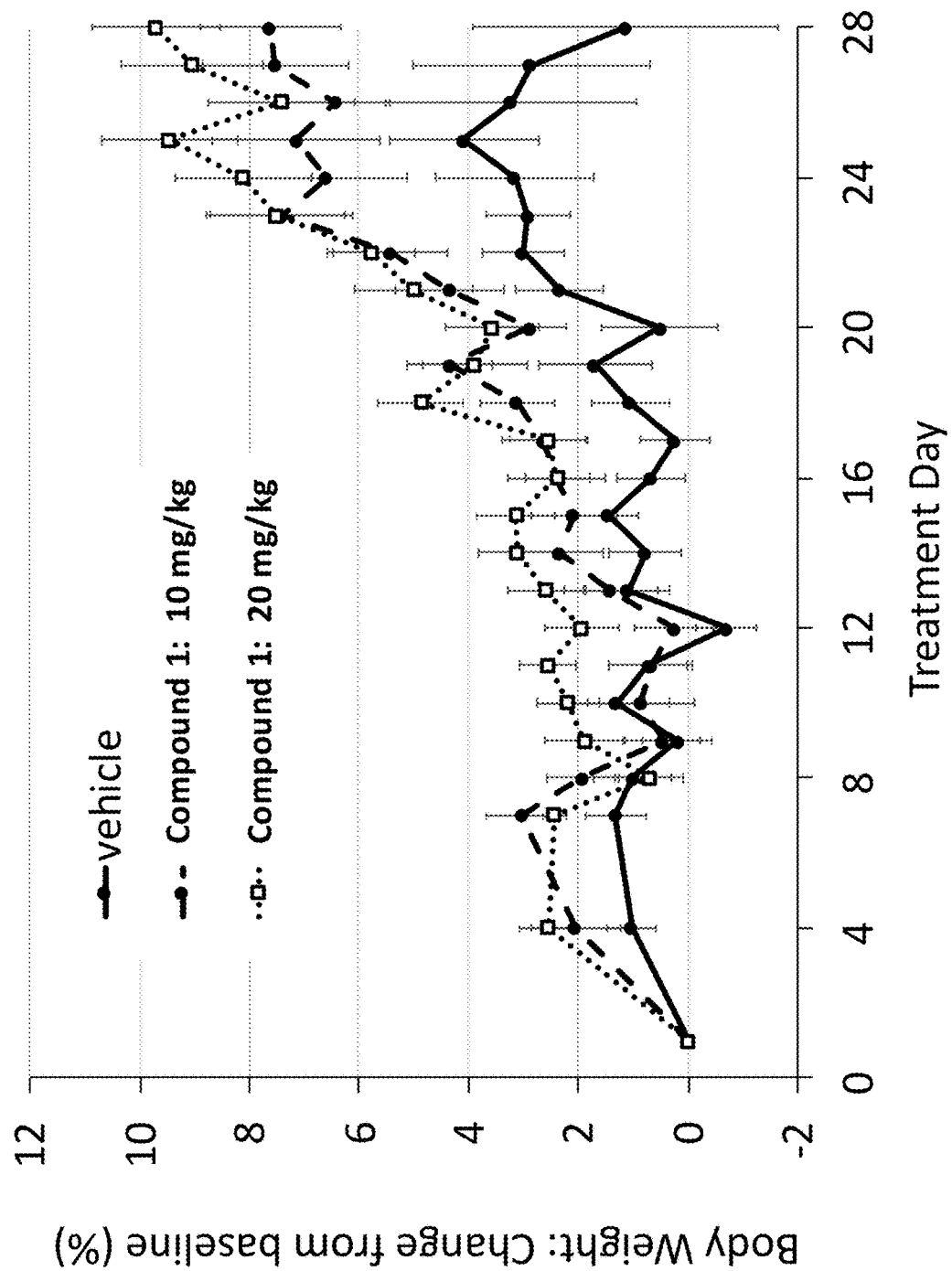
FIG. 6 depicts relative changes of body weight (%) from the baseline of Compound 1 MTD study in BALB/c nude mice.

Mice body weight change and percentage of relative change of body weight (RCBW) were shown in FIGS. 5 and 6. Overall, Compound 1 was well tolerated with no obvious body weight loss observed in in 5 mg/kg QD, 10 mg/kg QD, 10 mg/kg Q2D and 20 mg/kg QD groups, but body weights in Compound 1 (40 mg/kg QD) group was lower in a statistically significant manner at day 20 and 21, compared with the vehicle control group (FIGS. 5 and 6). No mice in all experimental groups died during the study period.

Example 24. Pharmacokinetics in Liver of Compound 1 and Compound 5

Compound 1 (20 mg per kg), Compound 5 (10 mg per kg), and pentamidine (20 mg per kg) were tested for their PK. Tissue samples were collected as described above in Example 23. Briefly, blood samples (approximately 50-60 µL) were collected under light isoflurane anesthesia from retro orbital plexus of mice at 0.5, 1, 3, 8, 48 and 72 hr. Plasma samples were separated by centrifugation at 2,000×g for 6 minutes and stored below −70±10° C. until bioanalysis. Immediately after collection of blood, animals were euthanized using excess $CO_2$ asphyxiation and samples were collected from set of five mice at each time point. Collected tissue samples were immediately dipped and rinsed three times in ice cold PBS (for 5-10 seconds/rinse using ~5-10 mL fresh PBS in disposable petri dish for each rinse) and dried on blotting paper. Tissue samples were homogenized using ice-cold phosphate buffer saline (pH7.4) and homogenates were stored below −70±10° C. until analysis. Total homogenate volume was three times the tissue weight except for liver samples, total homogenate volume was ten times the liver weight. Bioanalysis process was determined by fit-for-purpose LC-MS/MS method.

Calibration standards were prepared by spiking the test compound into blank plasma. 10 μL of working calibration standard was spiked into 190 μL of blank Mice Plasma or tissue homogenate to generate linearly spiked calibration standards. Calibrator concentrations were 5,000, 2,000, 1,000, 200, 100, 20, 10, 2 and 1 ng/mL. Calibration standard samples were processed along with the test samples. Twenty-five μL aliquots of plasma or tissue homogenate test samples were treated with 100 μL of acetonitrile containing internal standard (500 ng/mL Glipizide). Samples were vortexed for 5 minutes. Samples were centrifuged for 10 minutes at a speed of 4000 rpm at 4° C. Following centrifugation, 100 μL of clear supernatant was transferred in 96-well plates of and analyzed using LC-MS/MS. Chromatographic separation was achieved using a Kintex Polar column (C18, 100×4.6 mm, 5p) and column oven temperature 45° C. For compound 1 diHCl the mobile phase A was water with 0.1% formic acid in Acetonitrile; mobile phase B was 10 mM ammonium formate. However, the mobile phase for pentamidine and Compound 5 mobile phase A was water with 0.1% formic acid and mobile phase B acetonitrile with 0.1% formic acid.

The gradient program for Compound 1 was as follows: 5% B (1-2.40 min), 90% B (2.60-3.00 min), and the initial for B was 90%. The retention rate was 1.47 per minute and the internal standard Glipizide was 1 per 9 minutes. The column was maintained at 45° C. For pentamidine and Compound 5, analysis was performed using 233 MassSpec by AB Sciex API5000 with Turbo Ion Spray interface operating in a positive ionization mode. Quantification was performed using multiple reaction monitoring (MRM) method with the transitions of (m/z) 328 à (m/z) 311 for Compound 5 and (m/z) 548 à (m/z) 366 for Edoxaban (internal standard). While, for pentamidine (m/z) 341 à (m/z) 324 and (m/z) 548 à (m/z) 366 for Verapmil (internal standard).

The gradient program for Compound 5 was as follows: 10% B (0-0.2 min), 95% B (1.5-2 min), the initial for B was 10% and it stopped at 2.6 mins. The flow rate was 0.5 mL/min. The gradient program for pentamidine was as follows: 10% B (0-0.2 min), 95% B (1.4-2 min), the initial for B was 10% and it stopped at 2.5 mins. The flow rate was 0.5 mL/min.

Figure 7:
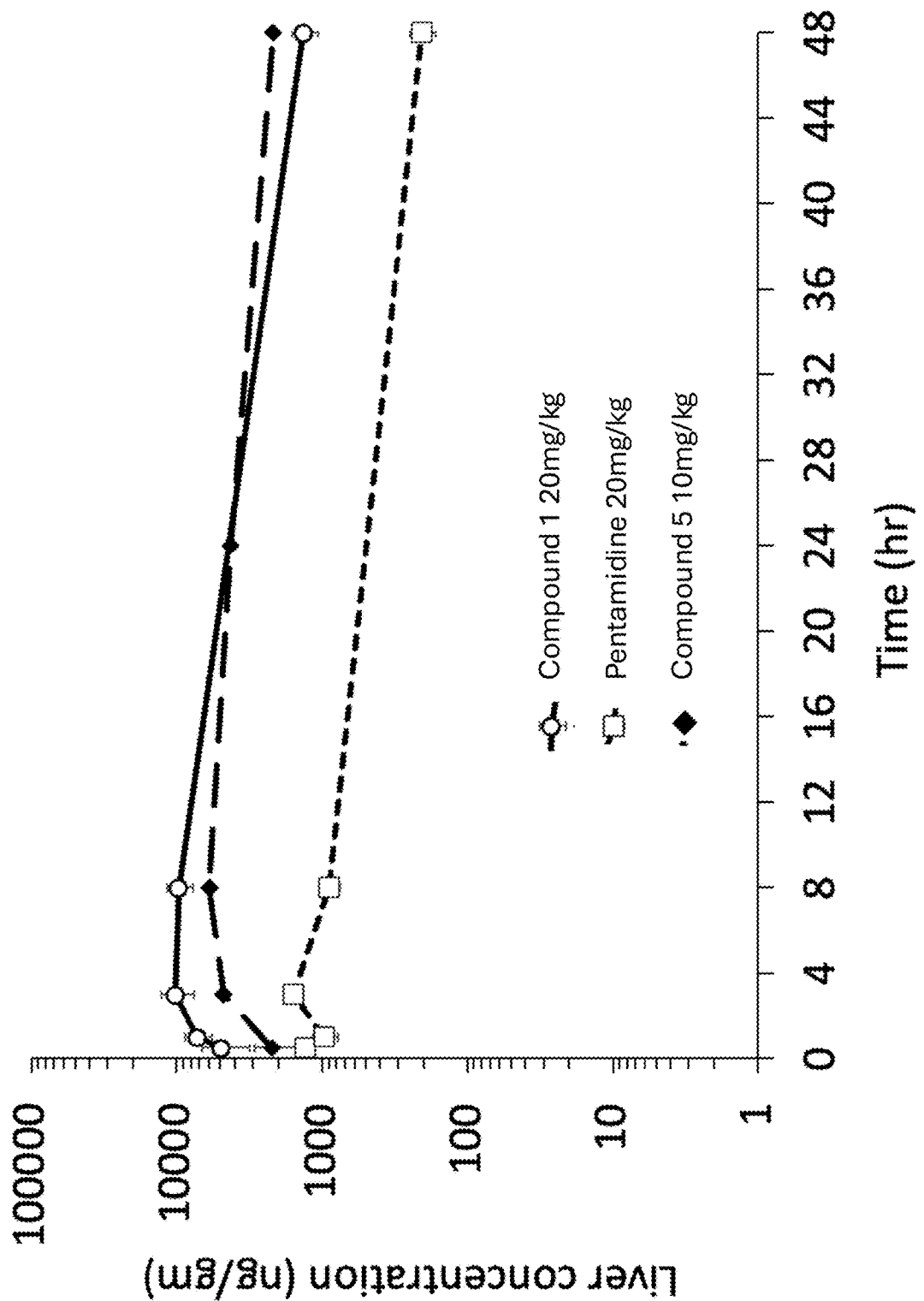
FIG. 7 depicts liver exposure of Compound 1 (20 mg per kg), Compound 5 (10 mg per kg) and pentamidine (20 mg per kg).
Figure 8:
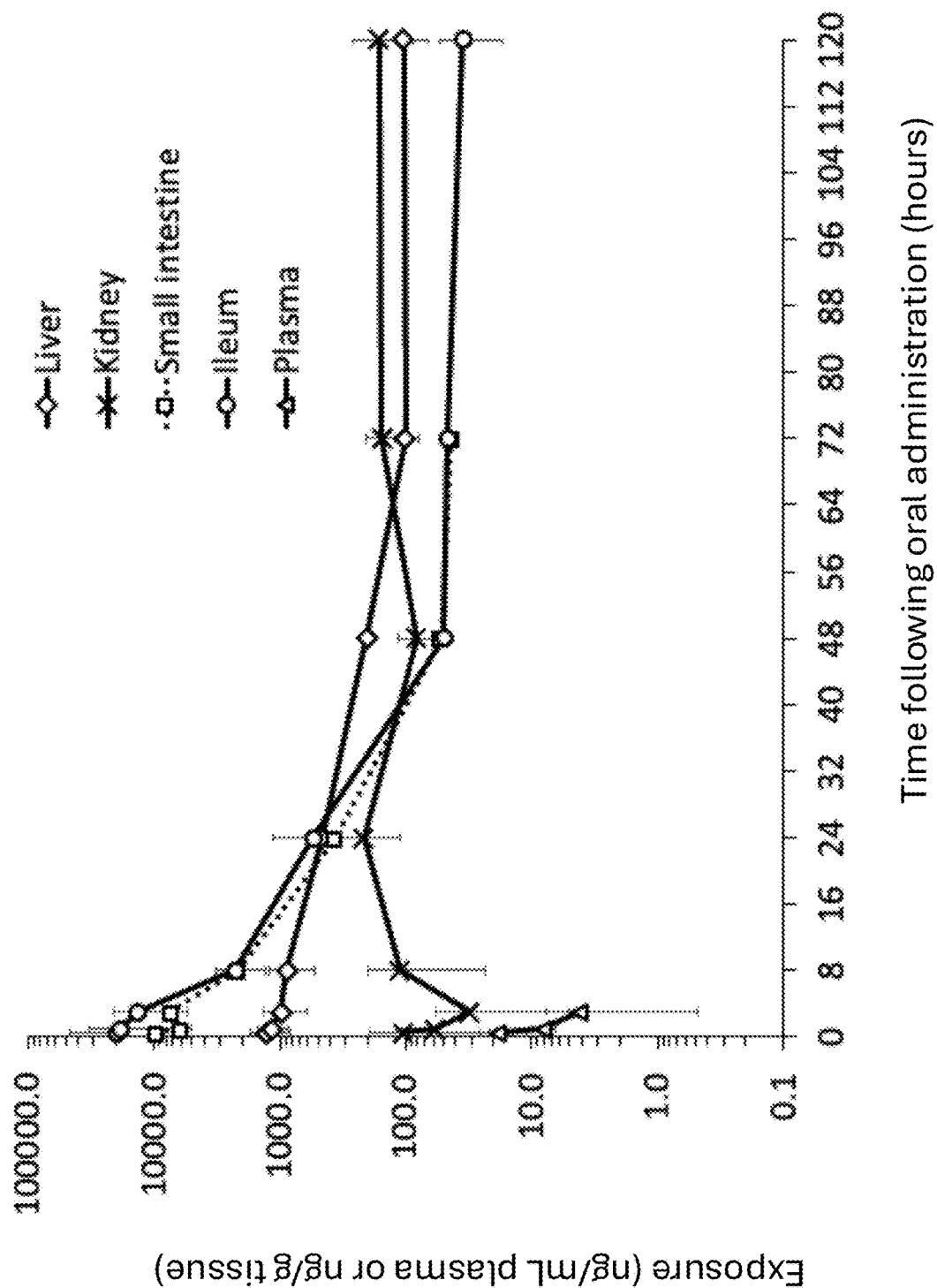
FIG. 8 depicts exposure of Compound 1 in the liver, kidney, small intestine, ileum, and plasma.
Figure 9:
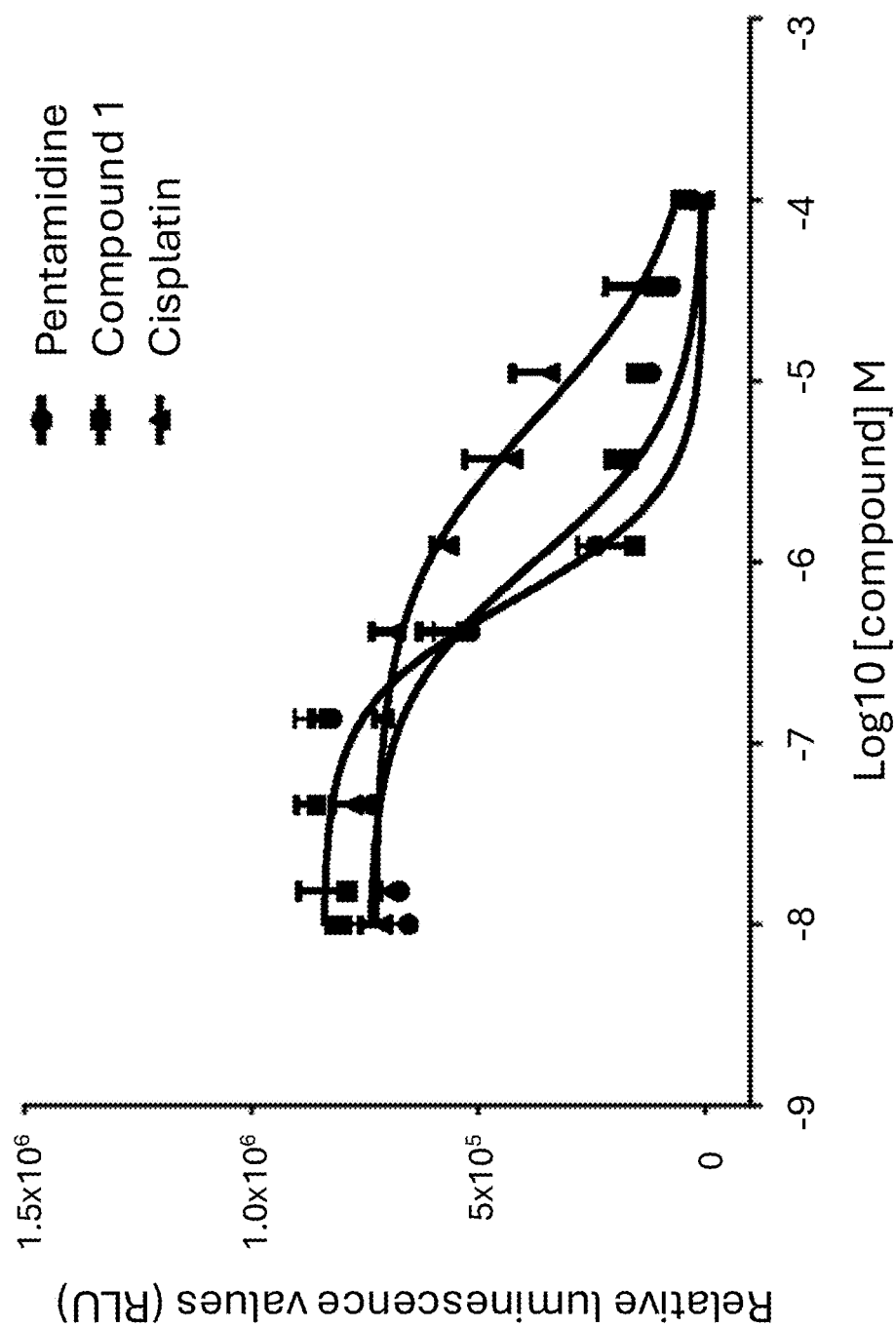
FIG. 9 depicts cytotoxicity of Compound 1 compared to those of pentamidine and cisplatin in Hep3B cell line.

As shown in FIG. 7, Compound 1 (20 mpk) and Compound 5 (10 mpk) demonstrated greater exposure to the liver than pentamidine (20 mpk) following oral administration (p.o.). Upon normalization of $C_{max}$ to dose for Compound 1 (20 mpk, p.o.) was almost 7-folds higher than pentamidine (20 mpk, p.o.). Compound 5 dosed at 10 mpk, p.o showed similar exposure rates to those of Compound 1 dosed at 20 mpk, p.o. Both Compounds 1 and 5 demonstrated higher half-life than pentamidine. Compound 5 exhibited higher half-life (approximately 3-fold) than Compound 1. FIG. 8 depicts exposure rates of Compound 1 in liver/kidney/small intestine/ileum/plasma.

In sum, Compound 1 and Compound 5 exhibited increased exposure in the liver as well as small intestine and ileum, whereas their exposure to the plasma was low in comparison to other tissues.

Example 25. In Vitro Evaluation of Cytotoxicity of Compound 1

The experiment tested pentamidine, Compound 1, and standard of care control, cisplatin, in full growth media for 8 days. Hep-3b cells were initially treated with the test compounds on Day 0, and the cells were then replenished with fresh compound dilutions on Day 3. Compound 1, pentamidine, and cisplatin were tested at 9 concentration points: 100 μM, 33.33 μM, 11.11 μM, 3.70 μM, 1.23 μM, 0.41 μM, 0.14 μM, 0.05 μM, and 0.02 μM (final DMSO concentration=0.5%). The raw data values from the CellTiter-Glo™ cell viability assay expressed in relative luminescence units were normalized to the vehicle for each individual plate, and any reduction in luminescence indicated a decrease in viability (%). The data was analyzed in GraphPad PRISM using a non-linear sigmoidal plot with variable slope (asymmetric four-point linear regression), and an $IC_{50}$ value for each compound was generated. The dose-response curves are shown in FIG. 7. The $IC_{50}$ values were generated based on the normalized dose-response curves. The $IC_{50}$ values of Pentamidine and Compound 1 were 0.8 and 0.6 μM in Help-3b lux, respectively. The $IC_{50}$ value for cisplatin (5.1 μM) was consistent with historical data.

Example 26 Colon Orthotopic In Vivo Study

This example shows the tolerability and effect of Compound 1 on tumor growth in an orthotopic colon cancer study.

Methods

Approximately 2.0× Luciferase stably expressing colon cancer tumor cells (COLO 205-Luc) cells suspended in 30 μl of DPBS were injected into cecum wall of BALB/c nude mice.

Animals were selected for grouping on day 20 after tumor implantation when their bioluminescence intensity increased for 3 consecutive measurements, which indicate the tumors were in a growth phase (the average bioluminescence measurement reached $2.13 \times 10^7$ photons/sec). The animals were assigned into groups using an Excel-based randomization software performing stratified randomization based upon their bioluminescence intensity. Treatment was initiated according to the predetermined regimen as shown in the experimental design table.

Mice were administered compound 1 at 10 mg/k daily, 20 mg/kg daily, 10 mg/kg twice daily, 20 mg/kg twice daily, or 40 mg/kg daily.

TABLE 9

Description of Testing Article Preparation

| Compounds | Package | Preparation | Concentration (mg/mL) | Storage |
|---|---|---|---|---|
| Vehicle | — | ddH$_2$O | — | 4° C. |
| Compound 1 | 1.52 g/vial | Weighed 68.96 mg Compound1 powder in one reagent bottle, added 14.00 mL ddH2O, vortexed and obtained a clear solution. | 4.0 mg/mL | 4° C. |

TABLE 9-continued

Description of Testing Article Preparation

| Compounds | Package | Preparation | Concentration (mg/mL) | Storage |
|---|---|---|---|---|
| Compound 1 | 1.52 g/vial | Weighed 103.43 mg Compound 1 powder in one reagent bottle, added 42.00 mL ddH2O, vortexed and obtained a clear solution. | 2.0 mg/mL | 4° C. |
| Compound 1 | 1.52 g/vial | Weighed 51.72 mg Compound 1 powder in one reagent bottle, added 42.00 mL ddH2O, vortexed and obtained a clear solution. | 1.0 mg/mL | 4° C. |

The major efficacy endpoint was bioluminescence (intensity values and change from baseline). The surgically inoculated mice were weighed and intraperitoneally administered luciferin at a dose of 150 mg/kg. Ten minutes after the luciferin injection, the animals were pre-anesthetized with the mixture gas of oxygen and isoflurane. When the animals were in a complete anesthetic state, the mice were moved into the imaging chamber for bioluminescence measurements with an IVIS (Lumina II) imaging system. The bioluminescence of the whole animal body, including primary and metastatic tumors, was measured and recorded once per week.

Tumor Growth Inhibition (TGI) was calculated for each group using the formula: TGI (%)=[1−(Ti−T0)/(Vi−V0)]×100; Ti is the average tumor bioluminescence value of a treatment group on a given day, T0 is the average tumor bioluminescence value of the treatment group on day 0, Vi is the average tumor bioluminescence value of the vehicle control group on the same day with Ti, and V0 is the average tumor bioluminescence value of the vehicle group on day 0.

Tumor weight was measured at the study termination. $T/C_{weight}$ value (in percent) was calculated using the formula: $T/C_{weight}\% = T_{weight}/C_{weight} \times 100\%$ where $T_{weight}$ and $C_{weight}$ were the mean tumor weights of the treated and vehicle control groups, respectively.

For comparison among three or more groups, a one-way ANOVA was performed. When a non-significant F-statistics (a ratio of treatment variance to the error variance) was obtained, comparisons between groups were carried out with Dunnett t(2-sided). All data were analyzed using SPSS 17.0. $p<0.05$ is considered to be statistically significant.

Results

Figure 10:
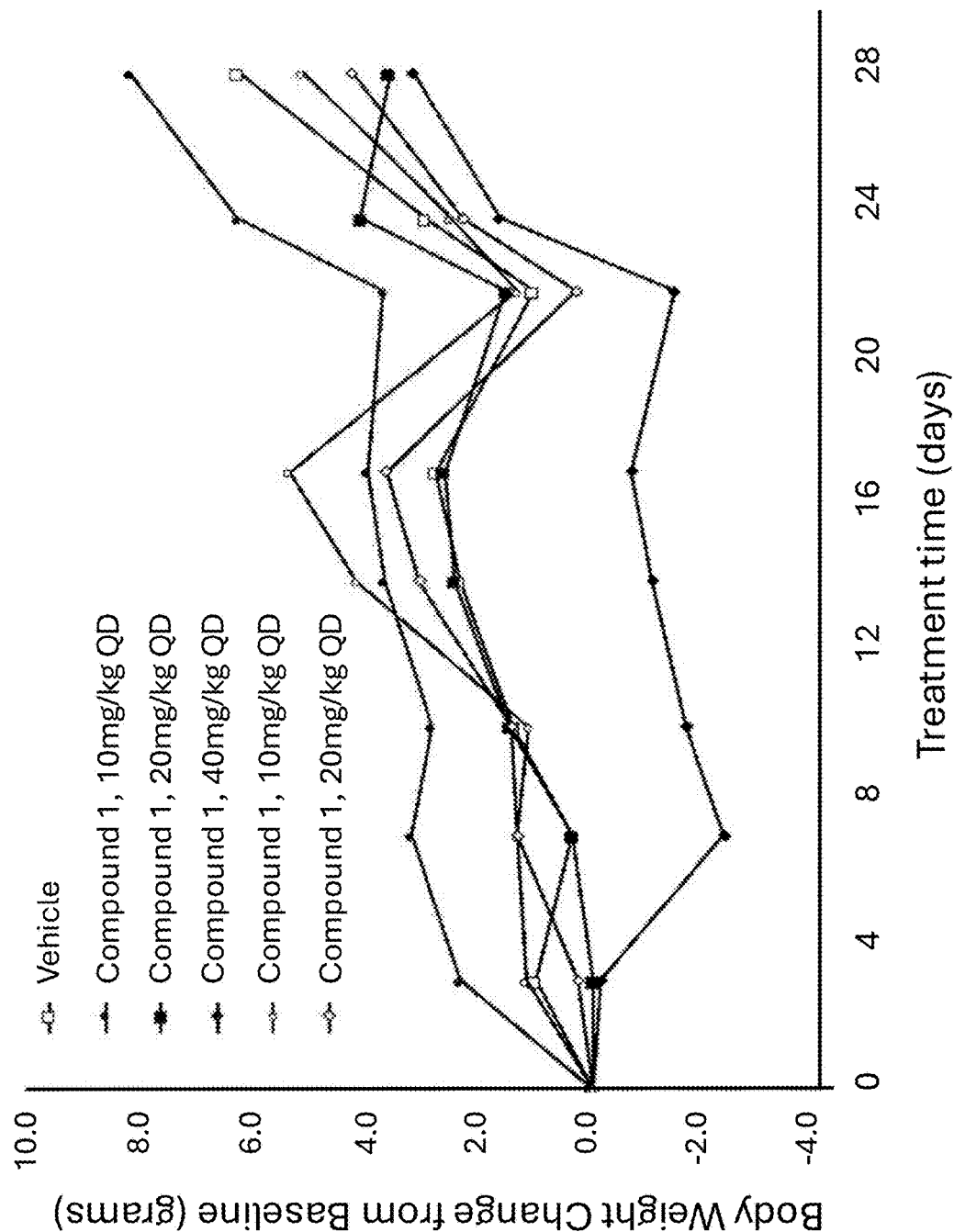
FIG. 10 shows depicts change in body weight over time in BALB/c nude mice treated with Compound 1 at 10 mg/kg QD, 20 mg/kg QD, 40 mg/kg QD, 10 mg/kg BID, and 20 mg/kg BID in an orthotic colon cancer model.

Animal body weight was monitored regularly as an indirect measure of toxicity. No groups lost weight obviously as a result of compound 1 administration (Table 10 and FIG. 10). FIG. 10 shows the relative change of body weights (%) from the first day of dosing. Data points represent percent group mean change in body weight. Error bars represent standard error of the mean (SEM). There were no deaths and no morbidity. Thus, there is no obvious toxicity associated with administration of compound 1 to tumor-bearing BALB/c nude mice.

TABLE 10

Body weight changes of the mice in the different groups

| Days after the start of treatment | Groups | | | | | |
|---|---|---|---|---|---|---|
| | Vehicle | Compound1, 10 mg/kg, QD | Compound1, 20 mg/kg, QD | Compound1, 40 mg/kg, QD | Compound1, 10 mg/kg, BID | Compound1, 20 mg/kg, BID |
| 0 | 21.2 ± 0.5[a] | 20.9 ± 0.5 | 20.8 ± 0.4 | 20.7 ± 0.5 | 21.0 ± 0.4 | 20.9 ± 0.5 |
| 3 | 21.4 ± 0.5 | 21.4 ± 0.5 | 20.8 ± 0.3 | 20.7 ± 0.5 | 21.2 ± 0.4 | 20.9 ± 0.5 |
| 7 | 21.2 ± 0.6 | 21.6 ± 0.5 | 20.8 ± 0.4 | 20.2 ± 0.4 | 21.2 ± 0.4 | 21.1 ± 0.5 |
| 10 | 21.5 ± 0.5 | 21.5 ± 0.4 | 21.0 ± 0.3 | 20.3 ± 0.5 | 21.2 ± 0.3 | 21.1 ± 0.5 |
| 14 | 21.7 ± 0.5 | 21.7 ± 0.4 | 21.2 ± 0.3 | 20.5 ± 0.5 | 21.8 ± 0.4 | 21.5 ± 0.6 |
| 17 | 21.7 ± 0.5 | 21.7 ± 0.4 | 21.3 ± 0.4 | 20.5 ± 0.5 | 22.1 ± 0.4 | 21.6 ± 0.6 |
| 22 | 21.4 ± 0.4 | 21.7 ± 0.5 | 21.1 ± 0.4 | 20.4 ± 0.5 | 21.2 ± 0.4 | 20.9 ± 0.5 |
| 24 | 21.8 ± 0.4 | 22.2 ± 0.6 | 21.6 ± 0.3 | 21.0 ± 0.5 | 21.5 ± 0.3 | 21.3 ± 0.5 |
| 28 | 22.5 ± 0.5 | 22.6 ± 0.5 | 21.5 ± 0.4 | 21.3 ± 0.5 | 22.0 ± 0.3 | 21.7 ± 0.5 |

Mean ± Standard Error of the Mean

Bioluminescence was used to measure tumor size in response to treatment with compound 1.

TABLE 11

Relative bioluminescence (%) over time

| Group | Days after the start of treatment | | | | |
|---|---|---|---|---|---|
| | 0 | 7 | 14 | 22 | 28 |
| Vehicle | 100 ± 0$^a$ | 312 ± 63 | 1162 ± 525 | 1433 ± 451 | 2724 ± 735 |
| COMPOUND 1, 10 mg/kg, QD | 100 ± 0 | 351 ± 88 | 1425 ± 930 | 2819 ± 1388 | 3171 ± 1602 |
| COMPOUND 1, 20 mg/kg, QD | 100 ± 0 | 171 ± 46 | 817 ± 269 | 923 ± 354 | 1613 ± 1022 |
| COMPOUND 1, 40 mg/kg, QD | 100 ± 0 | 210 ± 57 | 357 ± 109 | 525 ± 145 | 512 ± 206 |
| COMPOUND 1, 10 mg/kg, BID | 100 ± 0 | 447 ± 103 | 1033 ± 385 | 2993 ± 1325 | 2715 ± 950 |
| COMPOUND 1, 20 mg/kg, BID | 100 ± 0 | 299 ± 91 | 1108 ± 433 | 2340 ± 1230 | 1877 ± 1076 |

Mean ± Standard Error of the Mean

Figure 11:
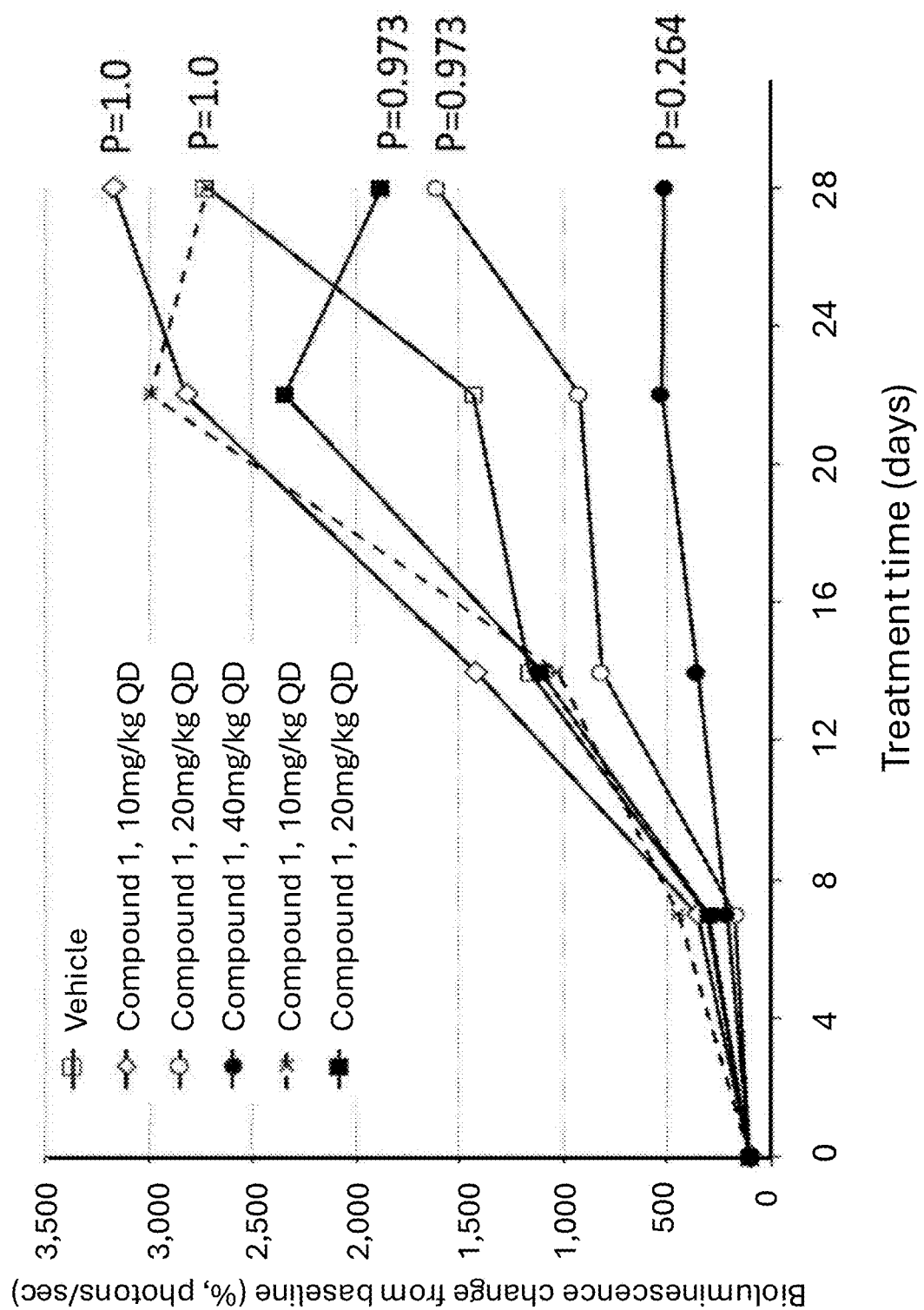
FIG. 11 shows the change in bioluminescence from baseline in BALB/c mice harboring luciferase stably expressing colon cancer tumor cells (COLO 205-Luc) treated with Compound 1 at 10 mg/kg QD, 20 mg/kg QD, 40 mg/kg QD, 10 mg/kg BID, and 20 mg/kg BID. P values reported are for day 28 for each treatment compared to vehicle.

FIG. 11 is a plot of the relative bioluminescence over time, as a measure of tumor growth.

This study shows that compound 1 does not have significant toxicity and is well tolerated. In addition, a non-statistically significant trend indicating that compound 1 administered at a dose of 20 mg/kg or 40 mg/kg daily may be effective for reducing tumor growth was observed. A further study evaluating the 40 mg/kg daily dosing regimen may be conducted in accordance with Example 27.

Example 27 Follow Up Colon Orthotopic In Vivo Study at 40 mg/kg Daily Dosage Methods Approximately $2.0 \times 10^6$ Colo205-luc2 cells suspended in 30 μl of DPBS are injected into the cecum wall of BALB/c nude mice.

Animals are selected for grouping on day 20 after tumor implantation when their bioluminescence intensity increased for 3 consecutive measurements, which indicate the tumors are in a growth phase (the average bioluminescence measurement reached $2.13 \times 10^7$ photons/sec). The animals are assigned into groups using an Excel-based randomization software performing stratified randomization based upon their bioluminescence intensity. Mice are administered compound 1 at 40 mg/kg daily.

The major efficacy endpoint is bioluminescence (intensity values and change from baseline). The surgically inoculated mice are weighed and intraperitoneally administered luciferin at a dose of 150 mg/kg. Ten minutes after the luciferin injection, the animals are pre-anesthetized with the mixture gas of oxygen and isoflurane. When the animals are in a complete anesthetic state, the mice were moved into the imaging chamber for bioluminescence measurements with an IVIS (Lumina II) imaging system. The bioluminescence of the whole animal body, including primary and metastatic tumors, is measured and recorded once per week.

Tumor Growth Inhibition (TGI) is calculated for each group using the formula: TGI (%)=[1−(Ti−T0)/(Vi−V0)]× 100; Ti is the average tumor bioluminescence value of a treatment group on a given day, T0 is the average tumor bioluminescence value of the treatment group on day 0, Vi is the average tumor bioluminescence value of the vehicle control group on the same day with Ti, and V0 is the average tumor bioluminescence value of the vehicle group on day 0.

Tumor weight is measured at the study termination. $T/C_{weight}$ value (in percent) is calculated using the formula: $T/C_{weight}\% = T_{weight}/C_{weight} \times 100\%$ where $T_{weight}$ and $C_{weight}$ are the mean tumor weights of the treated and vehicle control groups, respectively.

For comparison among three or more groups, a one-way ANOVA is performed. If a non-significant F-statistics (a ratio of treatment variance to the error variance) is obtained, comparisons between groups are carried out with Dunnett t(2-sided). All data are analyzed using SPSS 17.0.

Example 28 Kidney Orthotopic In Vivo Study

Balb/c nude mice are given injections of $4 \times 10^{\wedge}6$ Luciferase stably expressing kidney cancer tumor cells (ACHN-Luc) in 40 ul of DPBS.

The bioluminescence of the whole animal body, including primary and metastatic tumors, is measured and images are recorded.

Before commencement of treatment, all animals are weighed and assigned into two groups using an Excel-based randomization software performing stratified randomization based upon their body weights. This ensures that all the groups are comparable at the baseline. Test animals receive 40 mg/kg compound once daily for 21 days.

| Group | n | Treatment | Dose mg/kg | Dosing volume | Dosing Route | Schedule |
|---|---|---|---|---|---|---|
| 1 | 8 | Vehicle | — | 10 uL/g | PO | QD × 21 days |
| 2 | 8 | Compound 1 | 40 mg/kg | 10 uL/g | PO | QD × 21 days |

Bioluminescence and animal body weight is measured over time.

ENUMERATED EMBODIMENTS

1. A compound having Formula (I) or a pharmaceutically acceptable salt thereof:

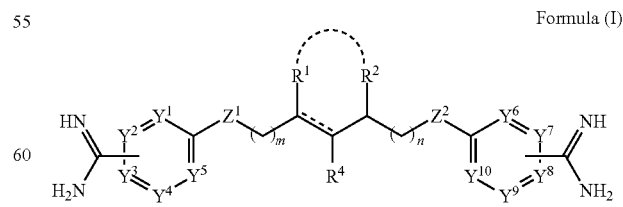

Formula (I)

wherein:
===== represents a single or double bond;
m or n is independently an integer of 0, 1, 2 or 3;
$Z^1$ or $Z^2$ is independently O, S, $SO_2$, $NR^3$, or $CR^5R^6$; and $Y^1$-$Y^{10}$ is independently N or $CR^7$,
wherein:
$R^1$ and $R^2$ are independently hydrogen or halo, or $R^1$ taken together with $R^2$ forms a cyclic group such as saturated, unsaturated or partially unsaturated 3-9 membered ring (e.g., 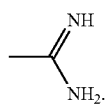);
$R^3$ is hydrogen, alkyl, cycloalkyl, aryl, or heteroaryl;
$R^4$ is hydrogen, halo, cycloalkyl, aryl, or heteroaryl;
$R^5$ or $R^6$ is independently hydrogen, alkyl, cycloalkyl, aryl, heteroaryl, amino, or
$R^5$ taken together with $R^6$ forms a saturated or partially unsaturated 3-9 membered ring; and
$R^7$ is independently hydrogen, halo, or amidine (-Am)

2. A compound having Formula (II) or a pharmaceutically acceptable salt thereof:

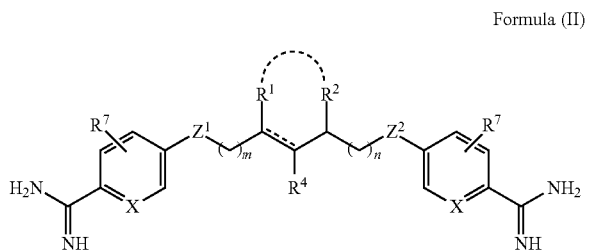

Formula (II)

wherein:
===== represents a single or double bond;
m or n is independently an integer of 0, 1, 2, 3 or 4;
$Z^1$ or $Z^2$ is independently O, S, $SO_2$, $NR^3$, or $CR^5R^6$; and
X is independently N or $CR^7$;
wherein:
$R^1$ and $R^2$ are independently hydrogen or halo, or
$R^1$ taken together with $R^2$ forms a cyclic group such as saturated, unsaturated or partially unsaturated 3-9 membered ring;
$R^3$ is hydrogen, alkyl, cycloalkyl, aryl, or heteroaryl;
$R^4$ is hydrogen, halo, cycloalkyl, aryl, or heteroaryl;
$R^5$ or $R^6$ is independently hydrogen, alkyl, cycloalkyl, aryl, heteroaryl, amino, or
$R^5$ taken together with $R^6$ forms a saturated or partially unsaturated 3-9 membered ring; and
$R^7$ is independently hydrogen or halo.

3. A compound of comprising Formula (III) or a pharmaceutically acceptable salt thereof:

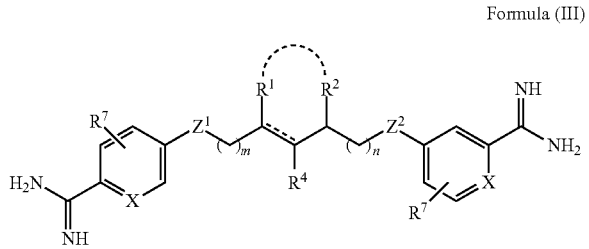

Formula (III)

wherein:
===== represents a single or double bond;
m or n is independently an integer of 0, 1, 2, 3 or 4;
$Z^1$ or $Z^2$ is independently O, S, $SO_2$, $NR^3$, or $CR^5R^6$; and
X is independently N or $CR^7$;
wherein:
$R^1$ and $R^2$ are independently hydrogen or halo, or
$R^1$ taken together with $R^2$ forms a cyclic group such as saturated, unsaturated or partially unsaturated 3-9 membered ring;
$R^3$ is hydrogen, alkyl, cycloalkyl, aryl, or heteroaryl;
$R^4$ is hydrogen, halo, cycloalkyl, aryl, or heteroaryl;
$R^5$ or $R^6$ is independently hydrogen, alkyl, cycloalkyl, aryl, heteroaryl, amino, or
$R^5$ taken together with $R^6$ forms a saturated or partially unsaturated 3-9 membered ring; and
$R^7$ is independently hydrogen or halo.

4. A compound having Formula (IV) or a pharmaceutically acceptable salt thereof:

Formula (IV)

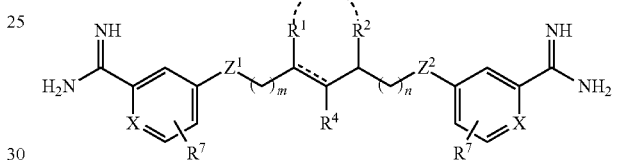

wherein:
===== represents a single or double bond;
m or n is independently an integer of 0, 1, 2, 3 or 4;
$Z^1$ or $Z^2$ is independently O, S, $SO_2$, $NR^3$, or $CR^5R^6$; and
X is independently N or $CR^7$;
wherein:
$R^1$ and $R^2$ are independently hydrogen or halo, or
$R^1$ taken together with $R^2$ forms a cyclic group such as saturated, unsaturated or partially unsaturated 3-9 membered ring;
$R^3$ is hydrogen, alkyl, cycloalkyl, aryl, or heteroaryl;
$R^4$ is hydrogen, halo, cycloalkyl, aryl, or heteroaryl;
$R^5$ or $R^6$ is independently hydrogen, alkyl, cycloalkyl, aryl, heteroaryl, amino, or
$R^5$ taken together with $R^6$ forms a saturated or partially unsaturated 3-9 membered ring; and
$R^7$ is independently hydrogen or halo.

5. A compound having Formula (V) or a pharmaceutically acceptable salt thereof, comprising:

Formula (V)

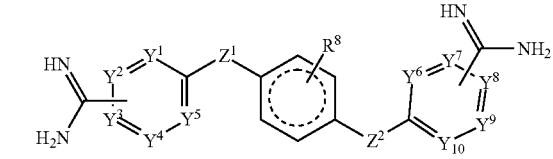

wherein:
===== presents a single or double bond;
$Z^1$ or $Z^2$ is independently O, S, $SO_2$, $NR^3$, or $CR^5R^6$; and
$Y^1$-$Y^{10}$ is independently N or $CR^7$, wherein:
R³ is hydrogen, alkyl, cycloalkyl, aryl, or heteroaryl;
R⁵ or R⁶ is independently hydrogen, alkyl, cycloalkyl, aryl, heteroaryl, amino, or
R⁵ taken together with R⁶ forms a saturated or partially unsaturated 3-9 membered ring; and
R⁷ is independently hydrogen, halo, or amidine (-Am)

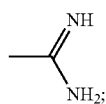

and
R⁸ is independently hydrogen, halo, cyano, alkyl, cycloalkyl, aryl, heteroaryl, or amino, optionally substituted.

6. A compound having Formula (VI) or a pharmaceutically acceptable salt thereof, comprising:

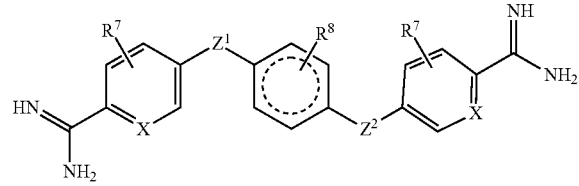

Formula (VI)

wherein:
===== represents a single or double bond;
Z¹ or Z² is independently O, S, SO₂, NR³, or CR⁵R⁶; and
X is independently N or CR⁷,
wherein:
R³ is hydrogen, alkyl, cycloalkyl, aryl, or heteroaryl;
R⁵ or R⁶ is independently hydrogen, alkyl, cycloalkyl, aryl, heteroaryl, amino, or
R⁵ taken together with R⁶ forms a saturated or partially unsaturated 3-9 membered ring;
R⁷ is independently hydrogen, halo, or amidine (-Am)

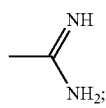

and
R⁸ is independently hydrogen, halo, cyano, alkyl, cycloalkyl, aryl, heteroaryl, or amino, optionally substituted.

7. A compound having Formula (VII) or a pharmaceutically acceptable salt thereof, comprising:

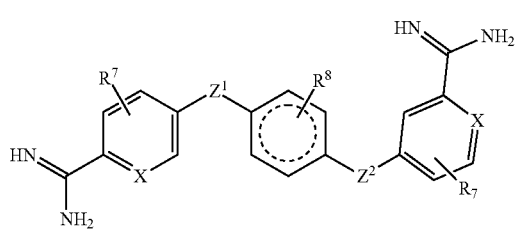

Formula (VII)

wherein:
===== represents a single or double bond;
Z¹ or Z² is independently O, S, SO₂, NR³, or CR⁵R⁶; and
X is independently N or CR⁷,
wherein:
R³ is hydrogen, alkyl, cycloalkyl, aryl, or heteroaryl;
R⁵ or R⁶ is independently hydrogen, alkyl, cycloalkyl, aryl, heteroaryl, amino, or
R⁵ taken together with R⁶ forms a saturated or partially unsaturated 3-9 membered ring; and
R⁷ is independently hydrogen, halo, or amidine (-Am)

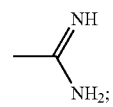

and
R⁸ is independently hydrogen, halo, cyano, alkyl, cycloalkyl, aryl, heteroaryl, or amino, optionally substituted.

8. A compound of Formula (VIII) or a pharmaceutically acceptable salt thereof, comprising:

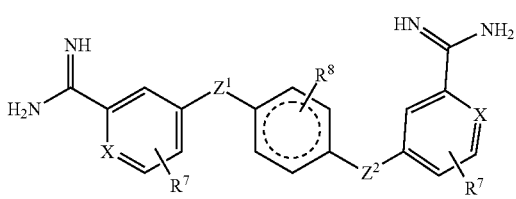

Formula (VIII)

wherein:
===== represents a single or double bond;
Z¹ or Z² is independently O, S, SO₂, NR³, or CR⁵R⁶; and
X is independently N or CR⁷,
wherein:
R³ is hydrogen, alkyl, cycloalkyl, aryl, or heteroaryl;
R⁵ or R⁶ is independently hydrogen, alkyl, cycloalkyl, aryl, heteroaryl, amino, or
R⁵ taken together with R⁶ forms a saturated or partially unsaturated 3-9 membered ring;
R⁷ is independently hydrogen, halo, or amidine (-Am)

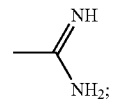

and
R⁸ is independently hydrogen, halo, cyano, alkyl, cycloalkyl, aryl, heteroaryl, or amino, optionally substituted.

9. A compound selected from the group consisting of:
5-(5-(4-carbamimidoylphenoxy)pentyloxy)picolinimidamide;
6-((5-(4-carbamimidoylphenoxy)pentyl)oxy)nicotinimidamide;
5-((5-(4-carbamimidoylphenoxy)pentyl)oxy)pyrimidine-2-carboximidamide;
5-((5-(4-carbamimidoylphenoxy)pentyl)oxy)pyrazine-2-carboximidamide;

5-(4-(4-carbamimidoylphenoxy)butoxy)picolinimidamide;
5-(4-(4-carbamimidoylphenoxy)butoxy)picolinimidamide;
5,5'-(pentane-1,5-diylbis(oxy))bis(pyrazine-2-carboximidamide);
6,6'-(heptane-1,7-diyl)dipicolinimidamide;
5,5'-(heptane-1,7-diyl)dinicotinimidamide;
6,6'-(heptane-1,7-diyl)dinicotinimidamide;
5-(5-(3-carbamimidoylphenoxy)pentyloxy)picolinimidamide;
4-((5-((6-carbamimidoylpyridin-3-yl)oxy)pentyl)oxy)picolinimidamide;
5-(((1r, 4r)-4-(4-carbamimidoylphenoxy)cyclohexyl)oxy)picolinimidamide;
5-(((1s, 4s)-4-(4-carbamimidoylphenoxy)cyclohexyl)oxy)picolinimidamide;
4-(5-(3-carbamimidoylphenoxy)pentyloxy)picolinimidamide;
5,5'-(butane-1,4-diylbis(oxy))dipicolinimidamide;
5-(3-(4-carbamimidoylphenoxy)propoxy)picolinimidamide;
5-{2-[(1R,3S)-3-[2-(4-carbamimidoylphenyl)ethyl]cyclohexyl]ethyl}pyridine-2-carboximidamide;
4-{[5-(4-carbamimidoylphenoxy)pentyl]oxy}pyridine-2-carboximidamide;
5-({5-[(6-carbamimidoylpyridin-3-yl)oxy]pentyl}oxy)pyridine-2-carboximidamide; and
4-({5-[(2-carbamimidoylpyridin-4-yl)oxy]pentyl}oxy)pyridine-2-carboximidamide.

10. A compound having a structure as follows:

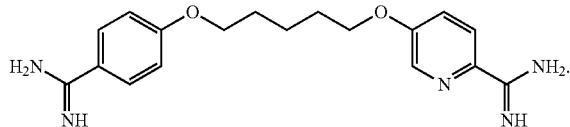 [SMILES: N=C(N)c1ccc(OCCCCCOc2ccc(C(=N)N)nc2)cc1]

11. A compound having a structure as follows:

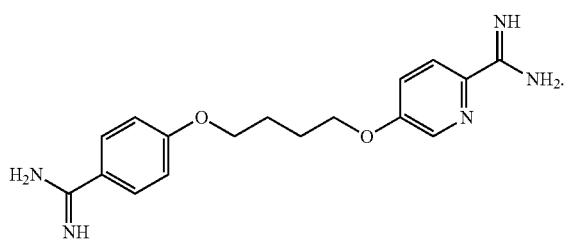 [SMILES: N=C(N)c1ccc(OCCCCOc2ccc(C(=N)N)nc2)cc1]

12. A method of treating cancer, the method comprising administering an effective amount of a compound of Formula (I) or a pharmaceutically acceptable salt thereof to a subject suffering from cancer, wherein said Formula (I) is as follows:

Formula (I)

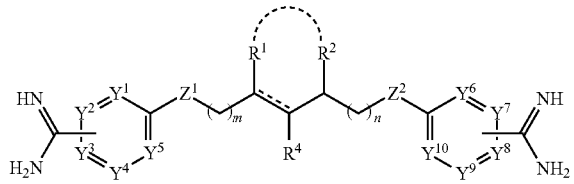

wherein:
===== represents a single or double bond;
m or n is independently an integer of 0, 1, 2 or 3;
$Z^1$ or $Z^2$ is independently O, S, $SO_2$, $NR^3$, or $CR^5R^6$; and
$Y^1$-$Y^{10}$ is independently N or $CR^7$,
wherein:
$R^1$ and $R^2$ are independently hydrogen or halo, or
$R^1$ taken together with $R^2$ forms a cyclic group such as saturated, unsaturated or partially unsaturated 3-9 membered ring (e.g., 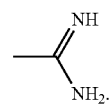);
$R^3$ is hydrogen, alkyl, cycloalkyl, aryl, or heteroaryl;
$R^4$ is hydrogen, halo, cycloalkyl, aryl, or heteroaryl;
$R^5$ or $R^6$ is independently hydrogen, alkyl, cycloalkyl, aryl, heteroaryl, amino, or
$R^5$ taken together with $R^6$ forms a saturated or partially unsaturated 3-9 membered ring; and
$R^7$ is independently hydrogen, halo, or amidine (-Am)

13. The method of Embodiment 12, wherein m is 1, and n is 1.
14. The method of Embodiment 12, wherein m is 1, and n is 0.
15. The method of Embodiment 12, wherein m is 0, and n is 1.
16. The method of Embodiment 12, wherein m is 1, and n is 2.
17. The method of Embodiment 12, wherein m is 2, and n is 1.
18. The method of Embodiment 12, wherein m is 2, and n is 2.
19. The method of Embodiment 12, wherein m is 0, and n is 0.
20. The method of Embodiment 12, wherein $Z^1$ or $Z^2$ is independently selected from the group of N, O, and S, each of which is optionally substituted.
21. The method of Embodiment 12, wherein $Z^1$ or $Z^2$ is independently S, optionally substituted.
22. The method of Embodiment 12, wherein $Z^1$ or $Z^2$ is independently O, optionally substituted.
23. The method of Embodiment 12, wherein $Z^1$ or $Z^2$ is independently N, optionally substituted.
24. The method of Embodiment 12, wherein $Z^1$ or $Z^2$ is independently $NR^3$, wherein $R^3$ is hydrogen.
25. The method of Embodiment 12, wherein $Z^1$ or $Z^2$ is independently $NR^3$, wherein $R^3$ is selected from the group of alkyl, cycloalkyl, aryl, and heteroaryl.
26. The method of Embodiment 12, wherein $Z^1$ or $Z^2$ is independently $NR^3$ or $CR^5R^6$.
27. The method of Embodiment 12, wherein $Z^1$ is $NR^3$, wherein $R^3$ is hydrogen, alkyl, cycloalkyl, aryl, or heteroaryl and $Z^2$ is $CR^5R^6$, wherein $R^5$ or $R^6$ is independently hydrogen, alkyl, cycloalkyl, aryl, heteroaryl, or amino; or $R^5$ taken together with $R^6$ forms a saturated or partially unsaturated 3-9 membered ring.
28. The method of Embodiment 12, wherein $Z^1$ or $Z^2$ is independently $CR^5R^6$, wherein $R^5$ or $R^6$ is independently hydrogen, alkyl, cycloalkyl, aryl, heteroaryl, or amino, or $R^5$ taken together with $R^6$ forms a saturated or partially unsaturated 3-9 membered ring.

29. The method of Embodiment 28, wherein R⁵ or R⁶ is independently hydrogen.
30. The method of Embodiment 12, wherein $Z^1$ or $Z^2$ is independently NR³, wherein R³ is hydrogen, alkyl, cycloalkyl, aryl, or heteroaryl.
31. The method of Embodiment 12, wherein $Z^1$ or $Z^2$ is independently O, S, or $SO_2$.
32. The method of Embodiment 12, wherein $Y^3$ and $Y^8$ are attached to amidine.
33. The method of Embodiment 12, wherein $Y^3$ and $Y^7$ are attached to amidine.
34. The method of Embodiment 12, wherein $Y^2$ and $Y^7$ are attached to amidine.
35. The method of Embodiment 12, wherein $R^1$ and $R^2$ are independently hydrogen.
36. The method of Embodiment 12, wherein $R^1$ taken together with $R^2$ forms a saturated, unsaturated or partially unsaturated 3-9 membered cyclic group (e.g., ).
37. The method of Embodiment 12, wherein $R^1$ taken together with $R^2$ forms 5, 6, or 7 membered cycloalkyl.
38. The method of Embodiment 12, wherein $R^1$ taken together with $R^2$ forms 6 membered cycloalkyl.
39. The method of Embodiment 12, wherein $R^1$ taken together with $R^2$ forms 7 membered cycloalkyl.
40. The method of Embodiment 12, wherein $Y^{1, 2, 4, 5, 6, and\ 8}$ are $CR^7$ (e.g., —CH); $Y^2$ is N; and $Y^3$ and $Y^7$ attached to amidine.
41. The method of Embodiment 12, wherein $Y^{1, 4, 5, 6, and\ 7}$ are —CH; $Y^2$ is N; and $Y^3$ and $Y^8$ are $CR^7$, wherein $R^7$ is amidine.
42. The method of Embodiment 12, wherein $Y^{1, 4, 5, 6, and\ 8}$ are —CH; $Y^3$ is N; and $Y^2$ and $Y^7$ are $CR^7$, wherein $R^7$ is amidine.
43. The method of Embodiment 12, wherein $Y^{1, 4, 5, 6, and\ 8}$ are —CH; $Y^3$ is N; and $Y^2$ and $Y^7$ are $CR^7$, wherein $R^7$ is amidine, wherein m is 1, and n is 0.
44. The method of Embodiment 12, wherein $Y^{1, 4, 5, and\ 6}$ are —CH; $Y^3$ and $Y^8$ are N; and $Y^2$ and $Y^7$ are $CR^7$, wherein $R^7$ is amidine, and wherein m is 1, and n is 0.
45. The method of Embodiment 12, wherein said cancer is selected from the group consisting of liver cancer, cholangiocarcinoma, osteosarcoma, melanoma, breast cancer, renal cancer, prostate cancer, gastric cancer, colorectal cancer, thyroid cancer, head and neck cancer, ovarian cancer, pancreatic cancer, neuronal cancer, lung cancer, uterine cancer, leukemia, and lymphoma.
46. The method of Embodiment 45, wherein said cancer is liver cancer.
47. The method of Embodiment 45, wherein said cancer is cholangiocarcinoma.
48. The method of Embodiment 45, wherein said cancer is prostate cancer.
49. The method of Embodiment 45, wherein said cancer is pancreatic cancer.
50. The method of Embodiment 45, wherein said cancer is lung cancer.
51. The method of Embodiment 45, wherein said cancer is small cell lung cancer.
52. The method of Embodiment 45, wherein said cancer is non-small cell lung cancer.
53. The method of Embodiment 45, wherein said cancer is breast cancer.
54. The method of Embodiment 45, wherein said cancer is colorectal cancer.
55. The method of Embodiment 45, wherein said cancer is renal cancer.
56. The method of Embodiment 12, wherein said compound of Formula (I), or a pharmaceutically acceptable salt thereof, is administered to the subject (e.g., human patient) orally, intravenously or subcutaneously at a dose of about 0.5 mg per kg, 0.6 mg per kg, about 0.7 mg per kg, about 0.8 mg per kg, about 0.9 mg per kg, about 1 mg per kg, about 2 mg per kg, about 3 mg per kg, about 4 mg per kg, about 5 mg per kg, about 6 mg per kg, about 7 mg per kg, about 8 mg per kg, about 9 mg per kg, about 10 mg per kg, about 15 mg per kg, about 20 mg per kg about 30 mg per kg, about 40 mg per kg, about 50 mg per kg, about 60 mg per kg, about 70 mg per kg, about 80 mg per kg, about 90 mg per kg, about 100 mg per kg, about 110 mg per kg, about 120 mg per kg, about 130 mg per kg, about 140 mg per kg, about 150 mg per kg, about 160 mg per kg, about 170 mg per kg, about 180 mg per kg, about 190 mg per kg, about 200 mg per kg, about 210 mg per kg, about 220 mg per kg, about 230 mg per kg, about 240 mg per kg, about 250 mg per kg, about 260 mg per kg, about 270 mg per kg, about 280 mg per kg, about 290 mg per kg, about 300 mg per kg, about 350 mg per kg, about 400 mg per kg, about 450 mg per kg, about 500 mg per kg, or about 600 mg per kg.
57. The method of Embodiment 12, wherein said subject is a human patient.
58. The method of Embodiment 12, wherein said compound of Formula (I), or a pharmaceutically acceptable salt thereof, is administered to the human patient orally.
59. The method of Embodiment 12, wherein said subject is administered about 1 mg per kg to about 200 mg per kg daily.
60. The method of Embodiment 12, wherein said subject is administered about 1 mg per kg to about 100 mg per kg daily.
61. The method of Embodiment 12, wherein said subject is administered about 1 mg per kg to about 50 mg per kg daily.
62. The method of Embodiment 12, wherein said subject is administered about 0.5 mg per kg to about 50 mg per kg daily.
63. The method of Embodiment 12, wherein said subject is administered about 2 mg per kg daily.
64. A method of treating cancer, the method comprising administering an effective amount of a compound of Formula (V) or a pharmaceutically acceptable salt thereof.

Formula (V)

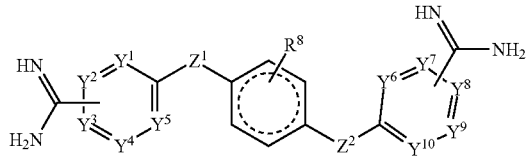

wherein:
===== represents a single or double bond;
$Z^1$ or $Z^2$ is independently O, S, $SO_2$, NR³, or $CR^5R^6$; and
$Y^1$-$Y^{10}$ is independently N or $CR^7$,
wherein:
R³ is hydrogen, alkyl, cycloalkyl, aryl, or heteroaryl;
R⁵ or R⁶ is independently hydrogen, alkyl, cycloalkyl, aryl, heteroaryl, amino, or R⁵ taken together with R⁶ forms a saturated or partially unsaturated 3-9 membered ring; and
R⁷ is independently hydrogen, halo, or amidine (-Am)

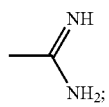

and

R$^8$ is independently hydrogen, halo, cyano, alkyl, cycloalkyl, aryl, heteroaryl, or amino, optionally substituted.

65. The method of Embodiment 64, wherein Z$^1$ or Z$^2$ is independently selected from the group consisting of O, N, and S, optionally substituted.

66. The method of Embodiment 64, wherein Z$^1$ or Z$^2$ is independently O, optionally substituted.

67. The method of Embodiment 64, wherein Z$^1$ or Z$^2$ is independently S, optionally substituted.

68. The method of Embodiment 64, wherein Z$^1$ or Z$^2$ is independently NR$^3$, wherein R$^3$ is hydrogen.

69. The method of Embodiment 64, wherein Z$^1$ or Z$^2$ is independently NR$^3$, wherein R$^3$ is alkyl, cycloalkyl, aryl, or heteroaryl.

70. The method of Embodiment 64, wherein Z$^1$ or Z$^2$ is independently CR$^5$R$^6$.

71. The method of Embodiment 64, wherein Z$^1$ is NR$^3$, wherein R$^3$ is hydrogen, alkyl, cycloalkyl, aryl, or heteroaryl and Z$^2$ is CR$^5$R$^6$, wherein R$^5$ or R$^6$ is independently hydrogen, alkyl, cycloalkyl, aryl, heteroaryl, or amino; or R$^5$ taken together with R$^6$ forms a saturated or partially unsaturated 3-9 membered ring.

72. The method of Embodiment 64, wherein Y$^3$ and Y$^8$ are independently amidine.

73. The method of Embodiment 64, wherein Y$^3$ and Y$^7$ are independently amidine.

74. The method of Embodiment 64, wherein Y$^2$ and Y$^7$ are independently amidine.

75. The method of Embodiment 64, wherein Y$^{1, 2, 4, 5, 6, 8}$ are CR$^7$ (e.g., —CH); Y$^2$ is N; and Y$^3$ and Y$^7$ attached to amidine.

76. The method of Embodiment 64, wherein Y$^{1, 4, 5, 6, and 7}$ are —CH; Y$^2$ is N; and Y$^3$ and Y$^8$ are CR$^7$, wherein R$^7$ is amidine.

77. The method of Embodiment 64, wherein Y$^{1, 4, 5, 6, and 8}$ are —CH; Y$^3$ is N; and Y$^2$ and Y$^7$ are CR$^7$, wherein R$^7$ is amidine.

78. The method of Embodiment 64, wherein Y$^{1, 4, 5, 6, and 8}$ are —CH; Y$^3$ is N; and Y$^2$ and Y$^7$ are CR$^7$, wherein R$^7$ is amidine.

79. The method of Embodiment 64, wherein Y$^{1, 4, 5, and 6}$ are —CH; Y$^3$ and Y$^8$ are N; and Y$^2$ and Y$^7$ are CR$^7$, wherein R$^7$ is amidine.

80. The method of Embodiment 64, wherein R$^3$ is hydrogen.

81. The method of Embodiment 64, wherein R$^3$ is alkyl.

82. The method of Embodiment 64, wherein R$^3$ is methyl.

83. The method of Embodiment 64, wherein R$^3$ is cycloalkyl.

84. The method of Embodiment 64, wherein R$^3$ is aryl.

85. The method of Embodiment 64, wherein R$^3$ is heteroaryl.

86. The method of Embodiment 64, wherein R$^5$ or R$^6$ is independently hydrogen, alkyl, cycloalkyl, aryl, heteroaryl, amino, or R$^5$ taken together with R$^6$ forms a saturated or partially unsaturated 3-9 membered ring.

87. The method of Embodiment 64, wherein R$^5$ and R$^6$ are hydrogen.

88. The method of Embodiment 64, wherein R$^7$ is independently hydrogen or halo.

89. The method of Embodiment 64, wherein R$^8$ is independently hydrogen, halo, cyano, alkyl, cycloalkyl, aryl, heteroaryl, or amino.

90. The method of Embodiment 64, wherein R$^8$ is hydrogen.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entireties and for all purposes to the same extent as if each individual publication or patent or patent application was specifically and individually indicated to be incorporated by reference in its entirety for all purposes.

What is claimed is:

1. A compound of Formula (A):

Formula (A)

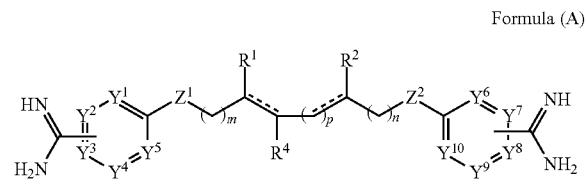

or a pharmaceutically acceptable salt thereof, wherein:
===== represents a single or double bond;
m or n is independently an integer of 0, 1, 2 or 3;
p is 0 or 1;
Z$^1$ or Z$^2$ is independently O, S, SO$_2$, NR$^3$, or CR$^5$R$^6$;
Y$^1$-Y$^{10}$ are each independently N or CR$^7$, wherein at least one of Y$^1$-Y$^{10}$ is N, provided that when the moiety

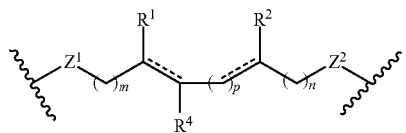

is taken together to form the moiety

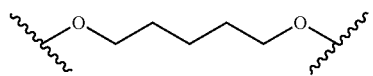 [SMILES: *OCCCCCO*]

wherein one of Y$^1$-Y$^5$ is N and one of Y$^8$-Y$^{10}$ is N and the remaining Y$^1$-Y$^{10}$ are each CH, then Y$^1$-Y$^5$ are taken together with the amidine substituent to form an amidine substituted pyridine ring that is different than the amidine substituted pyridine ring formed by Y$^6$-Y$^{10}$ so that the compound is asymmetrical;
R$^1$ and R$^2$ are each hydrogen,
R$^3$ is hydrogen, alkyl, cycloalkyl, aryl, or heteroaryl;
R$^4$ is hydrogen, halo, cycloalkyl, aryl, or heteroaryl;
R$^5$ or R$^6$ is independently hydrogen, alkyl, cycloalkyl, aryl, heteroaryl, amino,
or R$^5$ taken together with R$^6$ forms a saturated or partially unsaturated 3-9 membered ring; and
R$^7$ is independently hydrogen, or halo.

2. The compound of claim 1, or a pharmaceutically acceptable salt thereof, wherein the compound is of Formula (I):

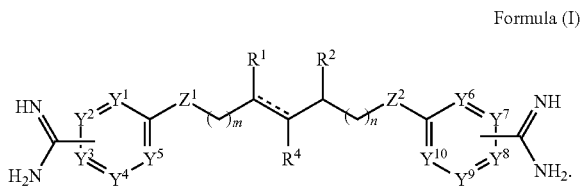

Formula (I)

3. The compound of claim 1, or a pharmaceutically acceptable salt thereof, wherein the compound is of Formula (II):

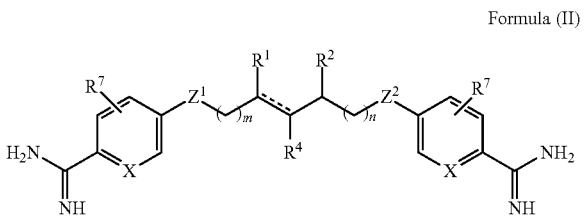

Formula (II)

wherein:
X is independently N or $CR^7$, provided that at least one X is N; and
$R^7$ is independently hydrogen or halo.

4. The compound of claim 1, or a pharmaceutically acceptable salt thereof, wherein the compound is of Formula (III):

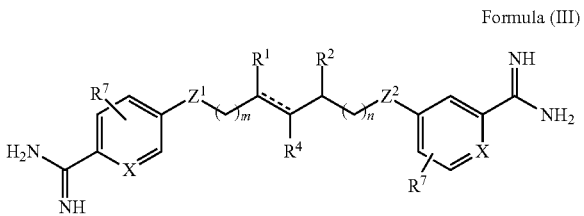

Formula (III)

wherein:
X is independently N or $CR^7$, provided that at least one X is N; and
$R^7$ is independently hydrogen or halo.

5. The compound of claim 1, or a pharmaceutically acceptable salt thereof, wherein the compound is of Formula (IV):

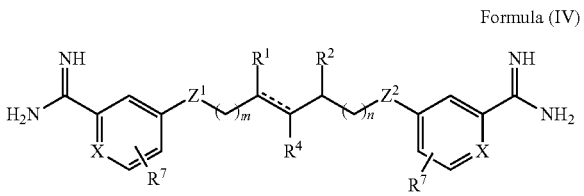

Formula (IV)

wherein:
X is independently N or $CR^7$, provided that at least one X is N; and
$R^7$ is independently hydrogen or halo.

6. The compound of claim 1, or a pharmaceutically acceptable salt thereof, wherein m is 1, and n is 1.

7. The compound of claim 1, or a pharmaceutically acceptable salt thereof, wherein m is 1, and n is 0.

8. The compound of claim 1, or a pharmaceutically acceptable salt thereof, wherein m is 0, and n is 1.

9. The compound of claim 1, or a pharmaceutically acceptable salt thereof, wherein m is 0, and n is 0.

10. The compound of claim 1, or a pharmaceutically acceptable salt thereof, wherein $Z^1$ or $Z^2$ is independently O.

11. The compound of claim 1, or a pharmaceutically acceptable salt thereof, wherein $Z^1$ or $Z^2$ is independently $CR^5R^6$, wherein $R^5$ or $R^6$ is independently hydrogen, alkyl, cycloalkyl, aryl, heteroaryl, or amino, or $R^5$ taken together with $R^6$ forms a saturated or partially unsaturated 3-9 membered ring.

12. The compound of claim 11, or a pharmaceutically acceptable salt thereof, wherein $R^5$ or $R^6$ is independently hydrogen.

13. The compound of claim 1, or a pharmaceutically acceptable salt thereof, wherein $Y^3$ and $Y^8$ are attached to amidine.

14. The compound of claim 1, or a pharmaceutically acceptable salt thereof, wherein $Y^3$ and $Y^7$ are attached to amidine.

15. The compound of claim 1, or a pharmaceutically acceptable salt thereof, wherein $Y^2$ and $Y^7$ are attached to amidine.

16. The compound of claim 1, or a pharmaceutically acceptable salt thereof, wherein $Y^{1, 4, 5, 6, 7, 9\ and\ 10}$ are —CH; $Y^2$ is N; and $Y^3$ and $Y^8$ are $CR^7$.

17. The compound of claim 1, or a pharmaceutically acceptable salt thereof, wherein $Y^{1, 4, 5, 6,\ and\ 8-10}$ are —CH; $Y^3$ is N; and $Y^2$ and $Y^7$ are $CR^7$.

18. The compound of claim 1, or a pharmaceutically acceptable salt thereof, wherein $Y^{1, 4, 5, 6,\ and\ 8-10}$ are —CH; $Y^3$ is N; and $Y^2$ and $Y^7$ are $CR^7$, wherein m is 1, and n is 0.

19. The compound of claim 1, or a pharmaceutically acceptable salt thereof, wherein $Y^{1, 4, 5,\ and\ 6}$ are —CH; $Y^3$ and $Y^8$ are N; and $Y^2$ and $Y^7$ are $CR^7$, and wherein m is 1, and n is 0.

20. The compound of claim 1, or a pharmaceutically acceptable salt thereof, wherein the compound is selected from the group consisting of:
5-(5-(4-carbamimidoylphenoxy)pentyloxy)picolinimidamide;
6-((5-(4-carbamimidoylphenoxy)pentyl)oxy)nicotinimidamide;
5-((5-(4-carbamimidoylphenoxy)pentyl)oxy)pyrimidine-2-carboximidamide;
5-((5-(4-carbamimidoylphenoxy)pentyl)oxy)pyrazine-2-carboximidamide;
5-(4-(4-carbamimidoylphenoxy)butoxy)picolinimidamide;
5,5'-(pentane-1,5-diylbis(oxy))bis(pyrazine-2-carboximidamide);
6,6'-(heptane-1,7-diyl)dipicolinimidamide;
5,5'-(heptane-1,7-diyl)dinicotinimidamide;
6,6'-(heptane-1,7-diyl)dinicotinimidamide;
5-(5-(3-carbamimidoylphenoxy)pentyloxy)picolinimidamide;
4-((5-((6-carbamimidoylpyridin-3-yl)oxy)pentyl)oxy)picolinimidamide;
4-(5-(3-carbamimidoylphenoxy)pentyloxy)picolinimidamide;
5,5'-(butane-1,4-diylbis(oxy))dipicolinimidamide;

5-(3-(4-carbamimidoylphenoxy) propoxy) picolinimidamide;

and

4-{[5-(4-carbamimidoylphenoxy) pentyl]oxy}pyridine-2-carboximidamide.

21. A compound having a structure as follows:

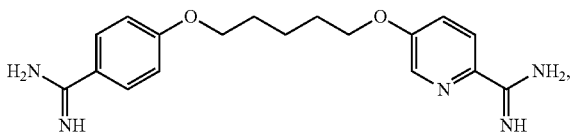 [SMILES: N=C(N)c1ccc(OCCCCCOc2ccc(C(=N)N)nc2)cc1]

or a pharmaceutically acceptable salt thereof.

22. A compound having a structure as follows:

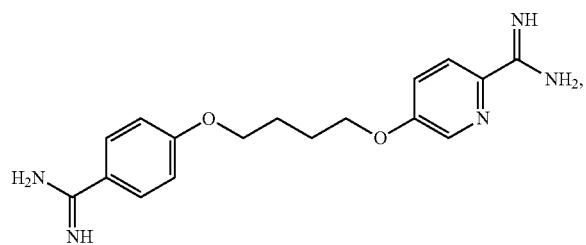 [SMILES: N=C(N)c1ccc(OCCCCOc2ccc(C(=N)N)nc2)cc1]

or a pharmaceutically acceptable salt thereof.

23. A pharmaceutical composition comprising a compound of claim 1, or a pharmaceutically acceptable salt thereof, and a pharmaceutically acceptable carrier.

24. A method of treating cancer, the method comprising administering an effective amount of a compound of claim 1, or a pharmaceutically acceptable salt thereof, to a subject suffering from cancer, wherein the cancer is liver cancer, cholangiocarcinoma, gallbladder cancer, renal cancer, prostate cancer, lung cancer, brain cancer, ovarian cancer, gastric cancer, colon cancer or bone cancer.

25. The method of claim 24, wherein said compound or a pharmaceutically acceptable salt thereof, is administered to the subject orally, intravenously or subcutaneously at a dose of about 0.5 mg per kg, 0.6 mg per kg, about 0.7 mg per kg, about 0.8 mg per kg, about 0.9 mg per kg, about 1 mg per kg, about 2 mg per kg, about 3 mg per kg, about 4 mg per kg, about 5 mg per kg, about 6 mg per kg, about 7 mg per kg, about 8 mg per kg, about 9 mg per kg, about 10 mg per kg, about 15 mg per kg, about 20 mg per kg about 30 mg per kg, about 40 mg per kg, about 50 mg per kg, about 60 mg per kg, about 70 mg per kg, about 80 mg per kg, about 90 mg per kg, about 100 mg per kg, about 110 mg per kg, about 120 mg per kg, about 130 mg per kg, about 140 mg per kg, about 150 mg per kg, about 160 mg per kg, about 170 mg per kg, about 180 mg per kg, about 190 mg per kg, about 200 mg per kg, about 210 mg per kg, about 220 mg per kg, about 230 mg per kg, about 240 mg per kg, about 250 mg per kg, about 260 mg per kg, about 270 mg per kg, about 280 mg per kg, about 290 mg per kg, about 300 mg per kg, about 350 mg per kg, about 400 mg per kg, about 450 mg per kg, about 500 mg per kg, or about 600 mg per kg.

* * * * *